(12) United States Patent
Manson et al.

(10) Patent No.: US 12,318,121 B2
(45) Date of Patent: Jun. 3, 2025

(54) BIPLANAR FORCEPS REDUCERS AND METHODS OF USE

(71) Applicant: Medos International Sarl, Le Locle (CH)

(72) Inventors: Alec Manson, Boston, MA (US); Chris Mickiewicz, Bridgewater, MA (US); Kevin Yeamans, Providence, RI (US); Michael Sorrenti, Middleboro, MA (US); Randy Betz, Jr., Wilmington, DE (US); Eric Biester, Barrington, RI (US)

(73) Assignee: Medos International Sàrl, Le Locle (CH)

( * ) Notice: Subject to any disclaimer, the term of this patent is extended or adjusted under 35 U.S.C. 154(b) by 282 days.

(21) Appl. No.: 17/522,164

(22) Filed: Nov. 9, 2021

(65) Prior Publication Data

US 2022/0142683 A1    May 12, 2022

Related U.S. Application Data

(60) Provisional application No. 63/111,606, filed on Nov. 9, 2020.

(51) Int. Cl.
*A61B 17/70*    (2006.01)

(52) U.S. Cl.
CPC ................ *A61B 17/7086* (2013.01)

(58) Field of Classification Search
CPC ............ A61B 17/7086; A61B 17/7088; A61B 17/7083
See application file for complete search history.

(56) References Cited

U.S. PATENT DOCUMENTS

| 410,780 A | 9/1889 | Cahn |
| 1,470,313 A | 10/1923 | Alfred |
| 1,628,144 A | 5/1927 | William |

(Continued)

FOREIGN PATENT DOCUMENTS

| CN | 102488548 B | 9/2013 |
| DE | 4238339 C2 | 10/1994 |

(Continued)

OTHER PUBLICATIONS

International Search Report and Written Opinion for Application No. PCT/EP2021/081168, mailed May 12, 2022 (11 pages).

(Continued)

*Primary Examiner* — Julianna N Harvey
(74) *Attorney, Agent, or Firm* — Barnes & Thornburg LLP

(57) ABSTRACT

Biplanar forceps reducer instruments and methods are disclosed herein. The instruments disclosed herein can engage an implant, such as a bone anchor receiver head, and reduce or move a spinal fixation element, such as a rod, in two planes to move the rod into a channel formed in the receiver head. Further, the biplanar forceps reducer instruments disclosed herein can allow for introduction and tightening of a set screw using an inserter that can pass through a cannulated tube of the reducer. The low profile and biplanar reduction functionality can allow a single type of reducer instrument to couple with each bone anchor along a spinal fixation construct and remain in position until the construct is secured in position.

23 Claims, 47 Drawing Sheets

(56) References Cited

U.S. PATENT DOCUMENTS

| | | |
|---|---|---|
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Charles |
| 2,248,054 A | 7/1941 | Joseph |
| 2,248,057 A | 7/1941 | Bond |
| 2,291,413 A | 7/1942 | Siebrandt |
| 2,370,407 A | 2/1945 | Ray |
| 2,800,820 A | 7/1957 | Valentin |
| 3,960,147 A | 6/1976 | Murray |
| 4,237,875 A | 12/1980 | Termanini |
| 4,271,836 A | 6/1981 | Bacal et al. |
| 4,411,259 A | 10/1983 | Drummond |
| 4,445,513 A | 5/1984 | Ulrich et al. |
| 4,655,223 A | 4/1987 | Kim |
| 4,809,695 A | 3/1989 | Gwathmey et al. |
| 4,896,661 A | 1/1990 | Bogert et al. |
| 5,014,407 A | 5/1991 | Boughten et al. |
| 5,020,519 A | 6/1991 | Hayes et al. |
| D343,000 S | 1/1994 | Olson |
| D346,217 S | 4/1994 | Sparker et al. |
| 5,306,248 A | 4/1994 | Barrington |
| 5,364,397 A | 11/1994 | Hayes et al. |
| 5,391,170 A | 2/1995 | McGuire et al. |
| 5,429,641 A | 7/1995 | Gotfried |
| 5,431,658 A | 7/1995 | Moskovich |
| 5,484,440 A | 1/1996 | Allard |
| 5,545,165 A | 8/1996 | Biedermann et al. |
| 5,551,320 A | 9/1996 | Horobec et al. |
| 5,616,143 A | 4/1997 | Schlapfer et al. |
| 5,649,931 A | 7/1997 | Bryant et al. |
| 5,672,175 A | 9/1997 | Martin |
| 5,683,399 A | 11/1997 | Jones |
| 5,697,933 A | 12/1997 | Gundlapalli et al. |
| 5,707,371 A | 1/1998 | Metz-Stavenhagen |
| D390,954 S | 2/1998 | Kumar et al. |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,810,878 A | 9/1998 | Burel et al. |
| 5,910,141 A | 6/1999 | Morrison et al. |
| 5,941,885 A | 8/1999 | Jackson |
| 5,951,564 A | 9/1999 | Schroder et al. |
| 5,951,579 A | 9/1999 | Dykes |
| 6,010,509 A | 1/2000 | Delgado et al. |
| 6,036,692 A | 3/2000 | Burel et al. |
| 6,099,528 A | 8/2000 | Saurat |
| 6,123,707 A | 9/2000 | Wagner |
| 6,139,549 A | 10/2000 | Keller |
| 6,183,472 B1 | 2/2001 | Lutz |
| 6,210,330 B1 | 4/2001 | Tepper |
| 6,251,112 B1 | 6/2001 | Jackson |
| 6,258,090 B1 | 7/2001 | Jackson |
| 6,371,973 B1 | 4/2002 | Tepper |
| 6,413,258 B1 | 7/2002 | Bernhardt, Jr. |
| 6,440,133 B1 | 8/2002 | Beale et al. |
| 6,440,142 B1 | 8/2002 | Ralph et al. |
| 6,440,144 B1 | 8/2002 | Bacher |
| 6,511,484 B2 | 1/2003 | Torode et al. |
| 6,530,929 B1 | 3/2003 | Justis et al. |
| 6,554,832 B2 | 4/2003 | Shluzas |
| 6,589,249 B2 | 7/2003 | Sater et al. |
| 6,648,888 B1 | 11/2003 | Shluzas |
| 6,660,006 B2 | 12/2003 | Markworth et al. |
| 6,676,661 B1 | 1/2004 | Martin Benlloch et al. |
| 6,726,692 B2 | 4/2004 | Bette |
| 6,743,231 B1 | 6/2004 | Gray et al. |
| 6,746,449 B2 | 6/2004 | Jones et al. |
| 6,752,832 B2 | 6/2004 | Neumann |
| 6,755,829 B1 | 6/2004 | Bono et al. |
| 6,790,208 B2 | 9/2004 | Oribe et al. |
| 6,790,209 B2 | 9/2004 | Beale et al. |
| 6,827,722 B1 | 12/2004 | Schoenefeld |
| 7,081,117 B2 | 7/2006 | Bono et al. |
| 7,083,621 B2 | 8/2006 | Shaolian et al. |
| 7,090,677 B2 | 8/2006 | Fallin et al. |
| 7,156,849 B2 | 1/2007 | Dunbar et al. |
| 7,179,254 B2 | 2/2007 | Pendekanti et al. |
| 7,179,261 B2 | 2/2007 | Sicvol et al. |
| 7,189,234 B2 | 3/2007 | Zucherman et al. |
| 7,278,995 B2 | 10/2007 | Nichols et al. |
| 7,320,689 B2 | 1/2008 | Keller |
| 7,371,239 B2 | 5/2008 | Dec et al. |
| 7,462,182 B2 | 12/2008 | Lim |
| 7,481,813 B1 | 1/2009 | Purcell |
| 7,485,120 B2 | 2/2009 | Ray |
| 7,491,207 B2 | 2/2009 | Keyer et al. |
| 7,527,638 B2 | 5/2009 | Anderson et al. |
| 7,572,281 B2 | 8/2009 | Runco et al. |
| 7,621,918 B2 | 11/2009 | Jackson |
| 7,651,502 B2 | 1/2010 | Jackson |
| 7,666,188 B2 | 2/2010 | Anderson et al. |
| 7,708,763 B2 | 5/2010 | Selover et al. |
| 7,776,040 B2 | 8/2010 | Markworth et al. |
| 7,806,912 B2 | 10/2010 | Lawton et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,867,237 B2 | 1/2011 | Stad et al. |
| 7,887,539 B2 | 2/2011 | Dunbar, Jr. et al. |
| 7,887,541 B2 | 2/2011 | Runco et al. |
| 7,901,434 B2 | 3/2011 | Drewry et al. |
| 7,922,724 B2 | 4/2011 | Lim |
| 7,931,677 B2 | 4/2011 | Abdelgany |
| 7,988,698 B2 | 8/2011 | Rosenberg et al. |
| 8,109,974 B2 | 2/2012 | Boomer et al. |
| 8,172,847 B2 | 5/2012 | Dziedzic et al. |
| 8,192,438 B2 | 6/2012 | Garamszegi |
| 8,216,241 B2 | 7/2012 | Runco et al. |
| 8,235,997 B2 | 8/2012 | Hoffman et al. |
| 8,246,657 B1 | 8/2012 | Samuel |
| 8,298,269 B2 | 10/2012 | Null et al. |
| 8,303,595 B2 | 11/2012 | Jones |
| 8,308,774 B2 | 11/2012 | Hoffman et al. |
| 8,317,837 B2 | 11/2012 | Rezach et al. |
| 8,337,527 B2 | 12/2012 | Hawkins et al. |
| 8,343,165 B2 | 1/2013 | Berrevoets |
| 8,377,104 B2 | 2/2013 | Jones et al. |
| 8,394,109 B2 | 3/2013 | Hutton et al. |
| 8,430,916 B1 | 4/2013 | Winslow et al. |
| 8,439,922 B1 | 5/2013 | Arnold et al. |
| 8,460,308 B2 | 6/2013 | Marino et al. |
| 8,540,718 B2 | 9/2013 | Dauster et al. |
| 8,556,904 B2 | 10/2013 | Rezach et al. |
| 8,603,145 B2 | 12/2013 | Forton et al. |
| 8,617,165 B2 | 12/2013 | Harper |
| 8,636,742 B2 | 1/2014 | Runco et al. |
| 8,636,776 B2 | 1/2014 | Rosenberg et al. |
| 8,647,347 B2 | 2/2014 | Runco et al. |
| 8,657,857 B2 | 2/2014 | Dall et al. |
| 8,685,029 B2 | 4/2014 | Dziedzic et al. |
| 8,715,323 B2 | 5/2014 | Ballard et al. |
| 8,728,124 B2 | 5/2014 | Miller |
| 8,747,409 B2 | 6/2014 | Ichelmann et al. |
| 8,764,756 B2 | 7/2014 | Jones |
| 8,790,348 B2 | 7/2014 | Stad et al. |
| 8,795,283 B2 | 8/2014 | Petit |
| 8,828,056 B2 | 9/2014 | Buss et al. |
| 8,845,640 B2 | 9/2014 | McLean et al. |
| 8,845,649 B2 | 9/2014 | Jackson |
| 8,870,881 B2 | 10/2014 | Rezach et al. |
| 8,876,869 B1 | 11/2014 | Schafer et al. |
| 8,900,240 B2 | 12/2014 | White et al. |
| 8,906,062 B2 | 12/2014 | Nichols et al. |
| 8,932,296 B2 | 1/2015 | Neary et al. |
| 8,951,289 B2 | 2/2015 | Matityahu |
| 8,956,362 B2 | 2/2015 | Landry et al. |
| 8,979,848 B2 | 3/2015 | Butters et al. |
| 8,986,349 B1 | 3/2015 | German et al. |
| 9,044,272 B2 | 6/2015 | Shaffrey et al. |
| 9,044,274 B2 | 6/2015 | Gunn et al. |
| 9,078,705 B2 | 7/2015 | Matthis et al. |
| 9,078,709 B2 | 7/2015 | McBride |

(56) References Cited

U.S. PATENT DOCUMENTS

| | | |
|---|---|---|
| 9,084,634 B1 | 7/2015 | Lab et al. |
| 9,119,674 B2 | 9/2015 | Matthis et al. |
| 9,125,694 B2 | 9/2015 | Butler et al. |
| 9,149,307 B2 | 10/2015 | Sandstrom et al. |
| 9,155,567 B2 | 10/2015 | Auerbach et al. |
| 9,186,188 B2 | 11/2015 | Gleason et al. |
| 9,204,901 B2 | 12/2015 | Black et al. |
| 9,204,909 B2 | 12/2015 | Rezach et al. |
| 9,220,543 B2 | 12/2015 | Walker et al. |
| 9,247,969 B2 | 2/2016 | Nunley et al. |
| 9,254,150 B2 | 2/2016 | Biedermann et al. |
| 9,265,533 B2 | 2/2016 | Nelson et al. |
| 9,265,538 B2 | 2/2016 | Stad et al. |
| 9,271,768 B2 | 3/2016 | Artaki et al. |
| 9,283,002 B2 | 3/2016 | Larroque-Lahitette et al. |
| 9,308,030 B2 | 4/2016 | Manninen |
| 9,451,994 B1 | 9/2016 | Whipple et al. |
| 9,486,256 B1 | 11/2016 | Lish et al. |
| 9,492,205 B2 | 11/2016 | Alsup et al. |
| 9,498,261 B2 | 11/2016 | McClintock |
| 9,795,417 B2 | 10/2017 | Beger et al. |
| 10,039,578 B2 | 8/2018 | Anderson et al. |
| 10,238,432 B2 | 3/2019 | Carruth et al. |
| 10,299,839 B2 | 5/2019 | Sicvol et al. |
| 10,398,476 B2 | 9/2019 | Lee et al. |
| D914,210 S | 3/2021 | Koros |
| 10,966,762 B2 | 4/2021 | Lee et al. |
| 11,291,481 B2 | 4/2022 | Schmura et al. |
| 11,291,482 B2 | 4/2022 | Schmura et al. |
| D1,004,774 S | 11/2023 | Schmura et al. |
| 11,832,855 B2 | 12/2023 | Lee et al. |
| 2001/0029376 A1 | 10/2001 | Sater et al. |
| 2002/0072752 A1 | 6/2002 | Zucherman et al. |
| 2002/0095153 A1 | 7/2002 | Jones et al. |
| 2003/0009168 A1 | 1/2003 | Beale et al. |
| 2003/0028195 A1 | 2/2003 | Bette |
| 2003/0083747 A1 | 5/2003 | Winterbottom et al. |
| 2003/0125750 A1 | 7/2003 | Zwirnmann et al. |
| 2003/0149438 A1 | 8/2003 | Nichols et al. |
| 2003/0171756 A1 | 9/2003 | Fallin et al. |
| 2003/0191370 A1 | 10/2003 | Phillips |
| 2003/0199872 A1 | 10/2003 | Markworth et al. |
| 2003/0208203 A1 | 11/2003 | Lim et al. |
| 2003/0225408 A1 | 12/2003 | Nichols et al. |
| 2004/0049191 A1 | 3/2004 | Markworth et al. |
| 2004/0147936 A1 | 7/2004 | Rosenberg et al. |
| 2004/0147937 A1 | 7/2004 | Dunbar, Jr. et al. |
| 2004/0172057 A1 | 9/2004 | Guillebon et al. |
| 2004/0176779 A1 | 9/2004 | Casutt et al. |
| 2004/0220567 A1 | 11/2004 | Eisermann et al. |
| 2004/0254576 A1 | 12/2004 | Dunbar, Jr. et al. |
| 2004/0267275 A1* | 12/2004 | Cournoyer ......... A61B 17/7086 623/908 |
| 2005/0015094 A1 | 1/2005 | Keller |
| 2005/0015095 A1 | 1/2005 | Keller |
| 2005/0033299 A1 | 2/2005 | Shluzas |
| 2005/0051648 A1 | 3/2005 | Mercier |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0143749 A1 | 6/2005 | Zalenski et al. |
| 2005/0149036 A1 | 7/2005 | Varieur et al. |
| 2005/0149048 A1 | 7/2005 | LePort et al. |
| 2005/0149053 A1 | 7/2005 | Varieur et al. |
| 2005/0192570 A1 | 9/2005 | Jackson |
| 2005/0192579 A1 | 9/2005 | Jackson |
| 2005/0228392 A1 | 10/2005 | Keyer et al. |
| 2005/0261702 A1 | 11/2005 | Oribe et al. |
| 2006/0009775 A1 | 1/2006 | Dec et al. |
| 2006/0025768 A1 | 2/2006 | Lott et al. |
| 2006/0036254 A1 | 2/2006 | Lim |
| 2006/0036260 A1 | 2/2006 | Runco et al. |
| 2006/0069391 A1 | 3/2006 | Jackson |
| 2006/0074418 A1 | 4/2006 | Jackson |
| 2006/0079892 A1 | 4/2006 | Roychowdhury et al. |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0166534 A1 | 7/2006 | Brumfield et al. |
| 2006/0166535 A1 | 7/2006 | Brumfield et al. |
| 2006/0229611 A1 | 10/2006 | Avery et al. |
| 2006/0233597 A1 | 10/2006 | Ensign et al. |
| 2006/0293692 A1* | 12/2006 | Whipple ............ A61B 17/7088 606/104 |
| 2007/0093849 A1 | 4/2007 | Jones et al. |
| 2007/0100347 A1 | 5/2007 | Stad et al. |
| 2007/0129731 A1 | 6/2007 | Sicvol et al. |
| 2007/0161998 A1 | 7/2007 | Whipple |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0213722 A1 | 9/2007 | Jones et al. |
| 2007/0233097 A1 | 10/2007 | Anderson et al. |
| 2007/0260261 A1 | 11/2007 | Runco et al. |
| 2007/0270817 A1 | 11/2007 | Rezach |
| 2007/0270880 A1 | 11/2007 | Lindemann et al. |
| 2007/0282337 A1 | 12/2007 | Garamszegi |
| 2008/0015601 A1 | 1/2008 | Castro et al. |
| 2008/0058805 A1 | 3/2008 | Stuart |
| 2008/0077134 A1 | 3/2008 | Dziedzic et al. |
| 2008/0077135 A1 | 3/2008 | Stad et al. |
| 2008/0154271 A1 | 6/2008 | Machalk et al. |
| 2008/0195155 A1 | 8/2008 | Hoffman et al. |
| 2008/0228233 A1 | 9/2008 | Hoffman et al. |
| 2008/0243190 A1 | 10/2008 | Dziedzic et al. |
| 2008/0255574 A1 | 10/2008 | Dye |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0082811 A1 | 3/2009 | Stad et al. |
| 2009/0088764 A1 | 4/2009 | Stad et al. |
| 2009/0105712 A1 | 4/2009 | Dauster et al. |
| 2009/0138056 A1 | 5/2009 | Anderson et al. |
| 2009/0143828 A1 | 6/2009 | Stad et al. |
| 2009/0312804 A1 | 12/2009 | Gamache et al. |
| 2010/0121385 A1* | 5/2010 | Blain ................ A61B 17/7086 606/86 A |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0093022 A1 | 4/2011 | Runco et al. |
| 2011/0144695 A1 | 6/2011 | Rosenberg et al. |
| 2011/0208254 A1 | 8/2011 | Villa et al. |
| 2012/0029571 A1 | 2/2012 | Schwab et al. |
| 2012/0053643 A1 | 3/2012 | Harper |
| 2012/0143265 A1 | 6/2012 | Biedermann et al. |
| 2012/0179214 A1 | 7/2012 | Geist et al. |
| 2012/0191144 A1 | 7/2012 | Peultier et al. |
| 2012/0203291 A1 | 8/2012 | Boulaine |
| 2012/0253413 A1* | 10/2012 | Runco ................ A61B 17/7088 606/86 A |
| 2013/0018419 A1 | 1/2013 | Rezach et al. |
| 2013/0066385 A1* | 3/2013 | Benoist ............. A61B 17/7086 606/86 A |
| 2013/0079826 A1 | 3/2013 | Simonson |
| 2013/0085534 A1 | 4/2013 | Hainard et al. |
| 2013/0123854 A1 | 5/2013 | Kondrashov et al. |
| 2013/0245702 A1 | 9/2013 | McBride |
| 2014/0012337 A1 | 1/2014 | Biedermann et al. |
| 2014/0018858 A1 | 1/2014 | Laeng et al. |
| 2014/0058464 A1* | 2/2014 | Hutchens ........... A61B 17/7086 606/86 A |
| 2014/0074106 A1 | 3/2014 | Shin |
| 2014/0094858 A1 | 4/2014 | Picetti et al. |
| 2014/0114363 A1 | 4/2014 | Stevenson et al. |
| 2014/0148865 A1 | 5/2014 | Hennard et al. |

(56) References Cited

U.S. PATENT DOCUMENTS

| | | |
|---|---|---|
| 2014/0163625 A1 | 6/2014 | Meyer et al. |
| 2014/0180298 A1 | 6/2014 | Stevenson et al. |
| 2014/0276896 A1 | 9/2014 | Harper |
| 2014/0277160 A1 | 9/2014 | Ziolo |
| 2014/0277170 A1 | 9/2014 | Barrett et al. |
| 2014/0277206 A1 | 9/2014 | Reitblat et al. |
| 2014/0296862 A1 | 10/2014 | Stad et al. |
| 2014/0311264 A1 | 10/2014 | Black et al. |
| 2014/0316475 A1 | 10/2014 | Parikh et al. |
| 2015/0057707 A1 | 2/2015 | Barrus et al. |
| 2015/0066042 A1 | 3/2015 | Cummins et al. |
| 2015/0100097 A1 | 4/2015 | Barrus |
| 2015/0100098 A1 | 4/2015 | Moore |
| 2015/0105832 A1 | 4/2015 | Gleason et al. |
| 2015/0112397 A1 | 4/2015 | Petit |
| 2015/0173803 A1 | 6/2015 | Droulout |
| 2015/0182265 A1 | 7/2015 | Biedermann et al. |
| 2015/0196328 A1 | 7/2015 | Hirschl et al. |
| 2015/0201971 A1 | 7/2015 | Gaines et al. |
| 2015/0257798 A1 | 9/2015 | Biedermann et al. |
| 2015/0359568 A1 | 12/2015 | Rezach |
| 2016/0022317 A1 | 1/2016 | Kraus |
| 2016/0066967 A1 | 3/2016 | Jackson et al. |
| 2016/0151093 A1 | 6/2016 | Barry et al. |
| 2016/0242825 A1 | 8/2016 | Simpson et al. |
| 2017/0265901 A1 | 9/2017 | Hawkins et al. |
| 2017/0333087 A1 | 11/2017 | Lee et al. |
| 2017/0333088 A1 | 11/2017 | Lee et al. |
| 2018/0014858 A1 | 1/2018 | Biester et al. |
| 2018/0161073 A1 | 6/2018 | Lee et al. |
| 2018/0185072 A1 | 7/2018 | Rubin et al. |
| 2018/0228518 A1 | 8/2018 | Carruth et al. |
| 2018/0280062 A1 | 10/2018 | Lee et al. |
| 2019/0117280 A1 | 4/2019 | Avidano et al. |
| 2019/0193541 A1 | 6/2019 | Takeda |
| 2020/0297395 A1 | 9/2020 | Schmura et al. |
| 2020/0297396 A1 | 9/2020 | Schmura et al. |
| 2021/0059725 A1 | 3/2021 | Avidano et al. |
| 2021/0177469 A1 | 6/2021 | Lee et al. |
| 2023/0157736 A1 | 5/2023 | Cromer et al. |
| 2024/0065736 A1 | 2/2024 | Lee et al. |

FOREIGN PATENT DOCUMENTS

| | | |
|---|---|---|
| DE | 29806563 U1 | 6/1998 |
| EP | 0948939 B1 | 5/2004 |
| EP | 1648320 A2 | 4/2006 |
| EP | 1796564 A1 | 6/2007 |
| EP | 2004079 B1 | 7/2013 |
| EP | 1574175 B1 | 5/2015 |
| FR | 2677242 A1 | 12/1992 |
| FR | 2680314 B1 | 11/1993 |
| FR | 2729291 B1 | 9/1997 |
| WO | 1996021396 A1 | 7/1996 |
| WO | 2002080787 A2 | 10/2002 |
| WO | 2003028566 A1 | 4/2003 |
| WO | 2005006948 A2 | 1/2005 |
| WO | 2005058173 A1 | 6/2005 |
| WO | 2006020443 A1 | 2/2006 |
| WO | 2010045301 A1 | 4/2010 |
| WO | 2023089096 A1 | 5/2023 |

OTHER PUBLICATIONS

International Preliminary Report on Patentability for Application No. PCT/EP2021/081168, mailed May 9, 2023 (8 pages).

International Search Report and Written Opinion for Application No. PCT/EP2021/081168, mailed May 12, 2022 (14 pages).

International Search Report and Written Opinion for PCT/US2018/065497, mailed Jul. 8, 2019.

Written Opinion and IPRP for PCT/EP2022/084215, mailed Mar. 23, 2023.

* cited by examiner

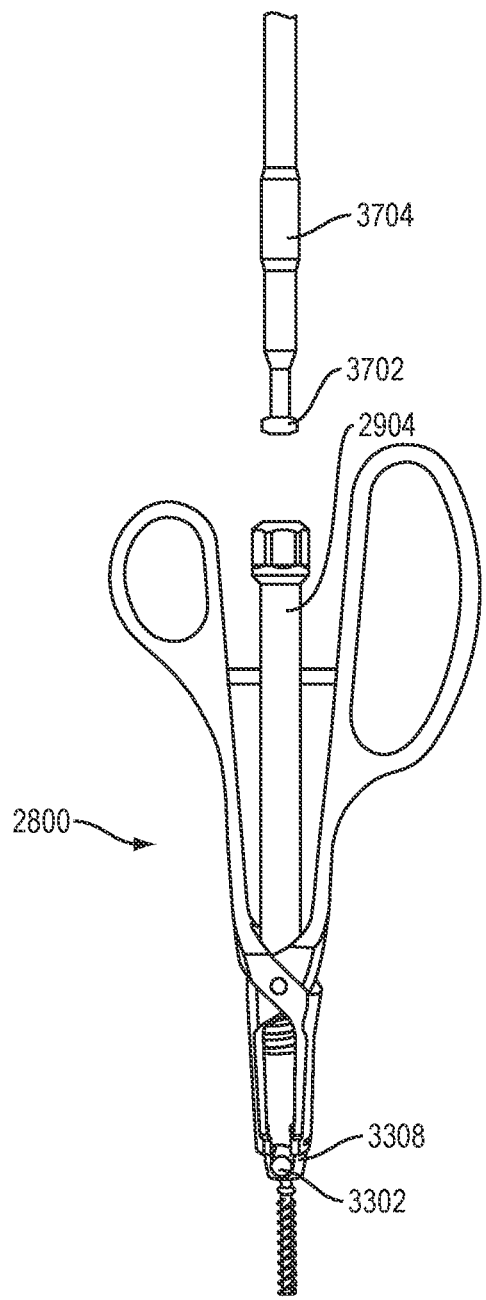
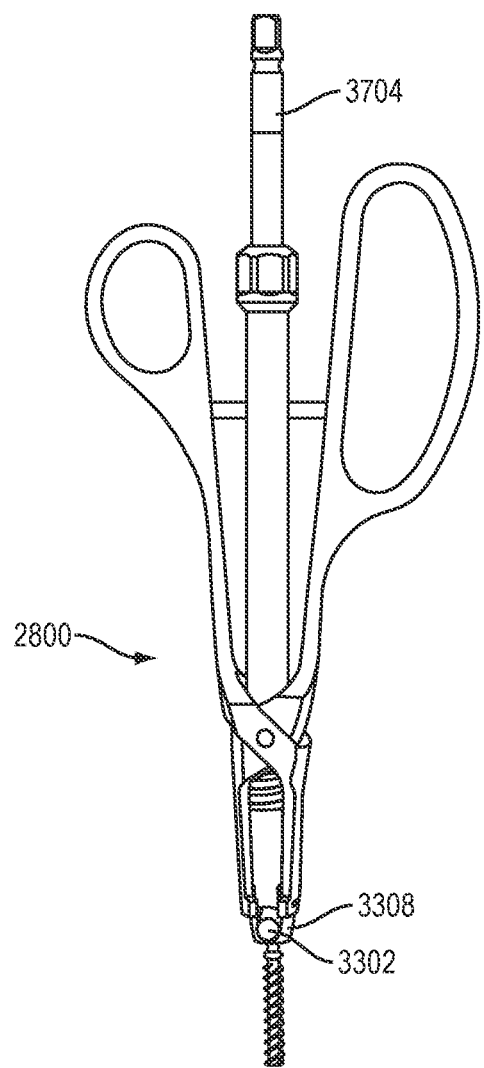
FIG. 37
FIG. 38

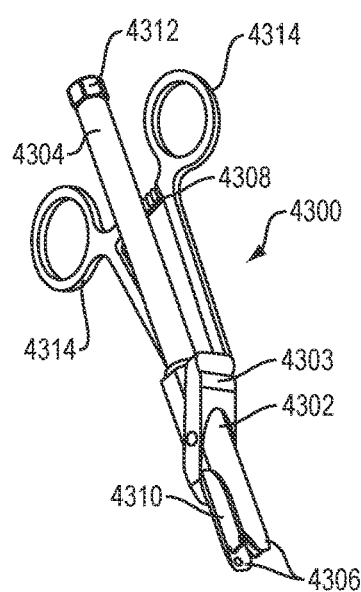
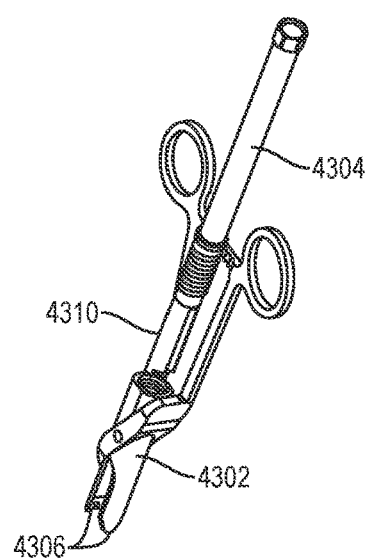
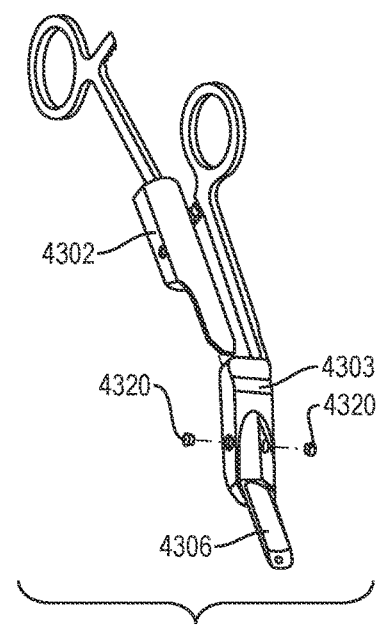
FIG. 43A    FIG. 45    FIG. 46
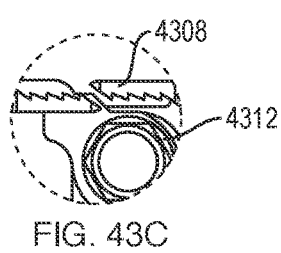
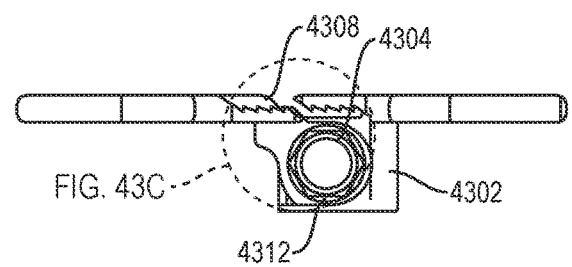
FIG. 43C    FIG. 43B
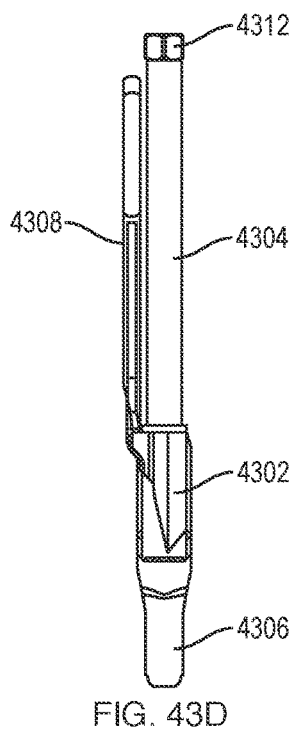
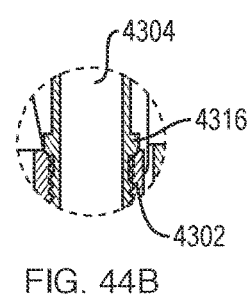
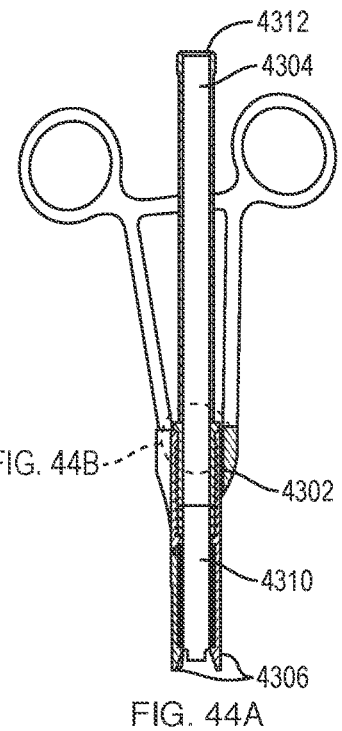
FIG. 43D    FIG. 44B    FIG. 44A

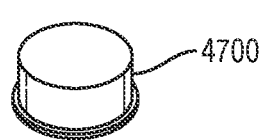
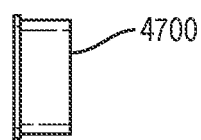
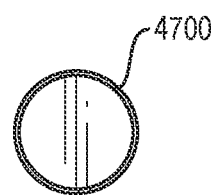
FIG. 47A　　　　FIG. 47B　　　　FIG. 47C
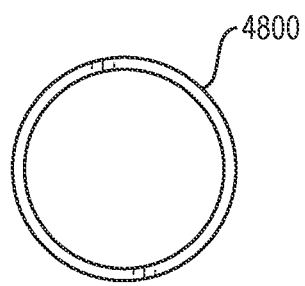
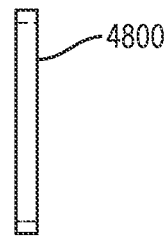
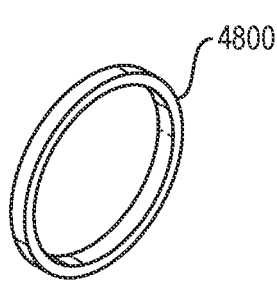
FIG. 48A　　　　FIG. 48B　　　　FIG. 48C
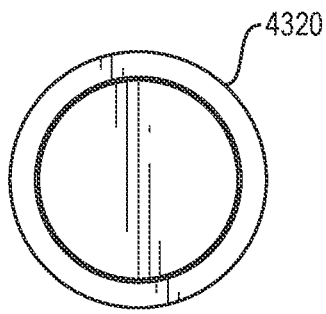
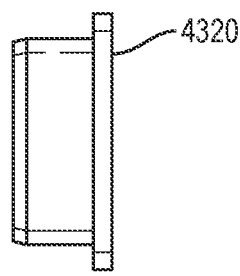
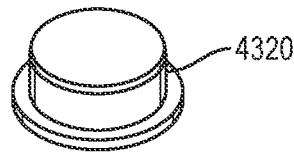
FIG. 49A　　　　FIG. 49B　　　　FIG. 49C

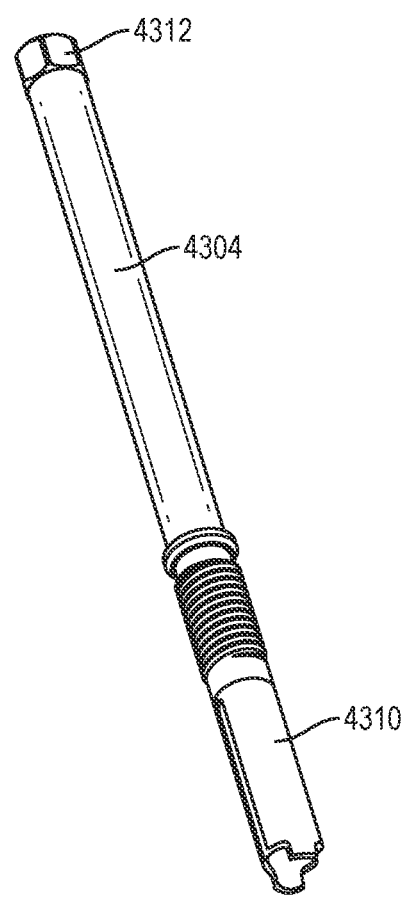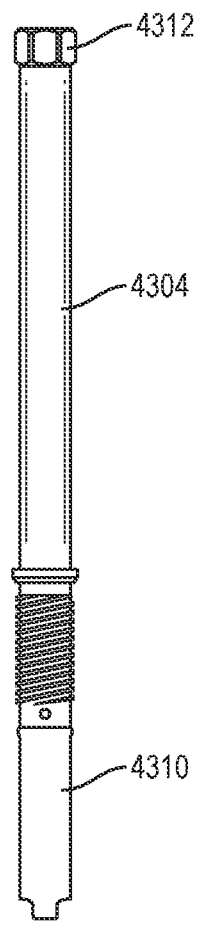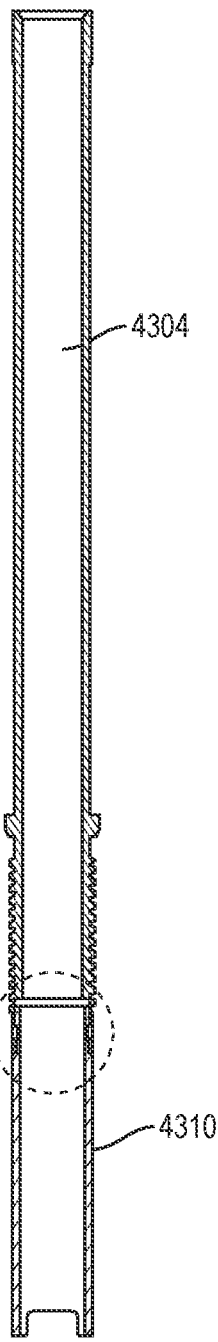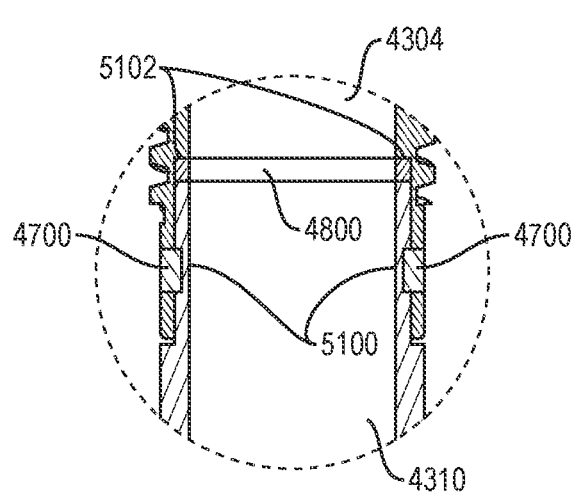
FIG. 50A
FIG. 50B
FIG. 51B
FIG. 51A

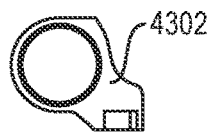
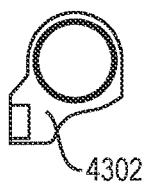
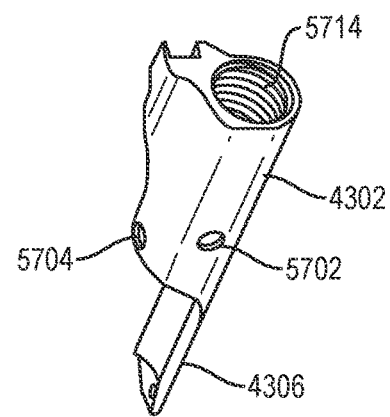
FIG. 57B    FIG. 57C    FIG. 57A
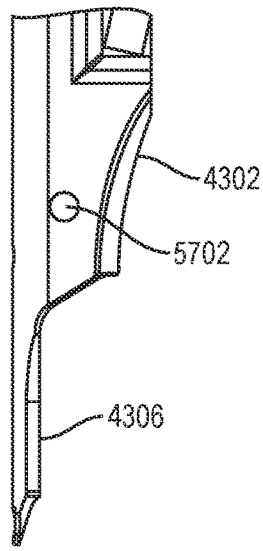
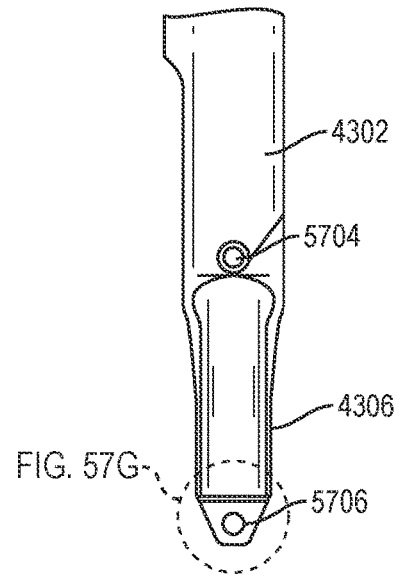
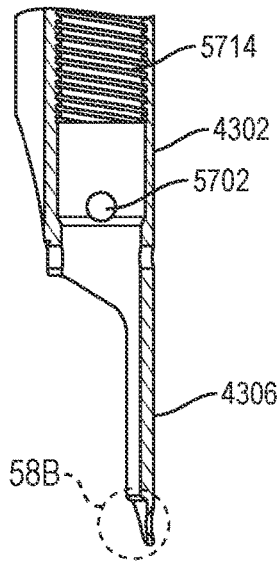
FIG. 57D    FIG. 57E    FIG. 58A
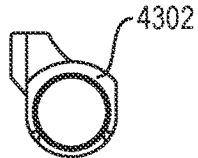
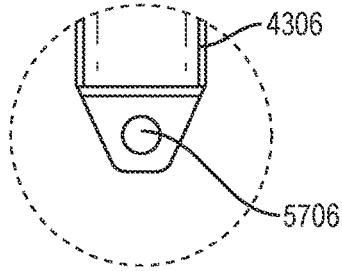
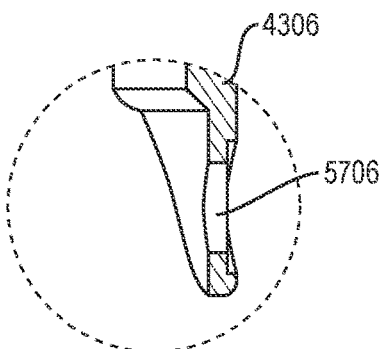
FIG. 57F    FIG. 57G    FIG. 58B

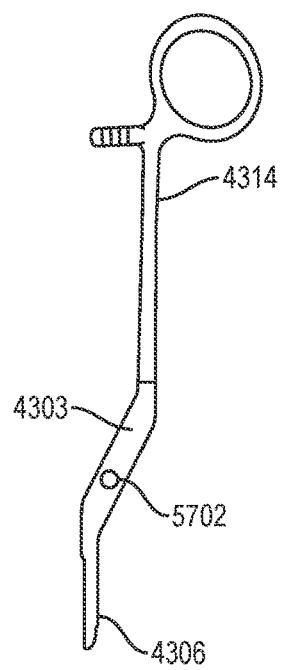 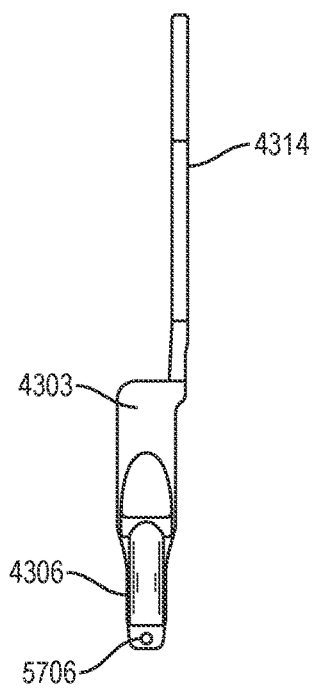 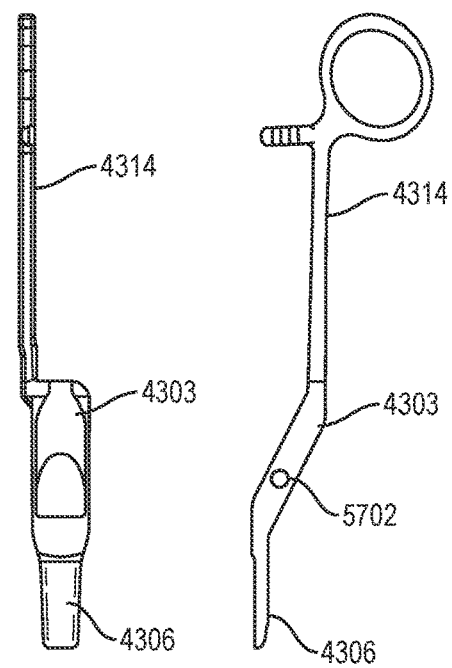
FIG. 63A  FIG. 63B  FIG. 63C  FIG. 63D
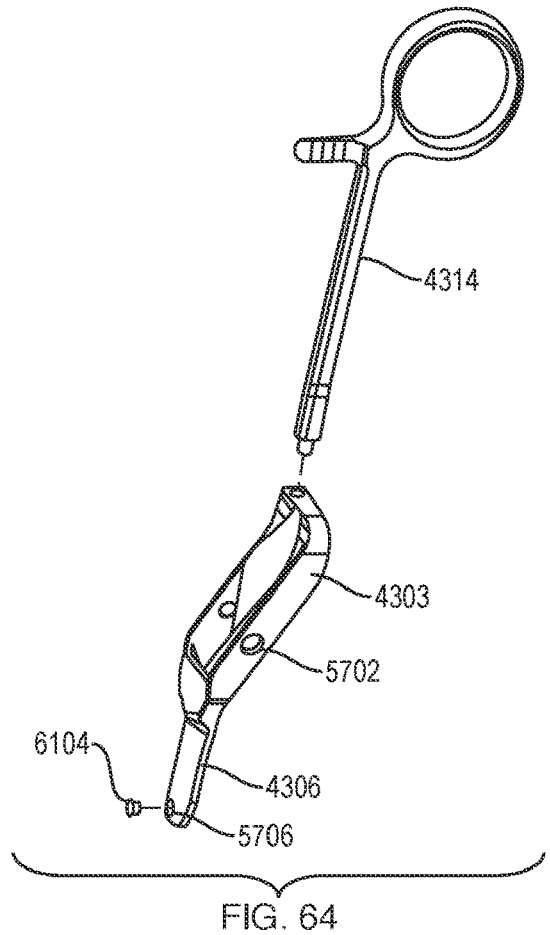
FIG. 63E
FIG. 64

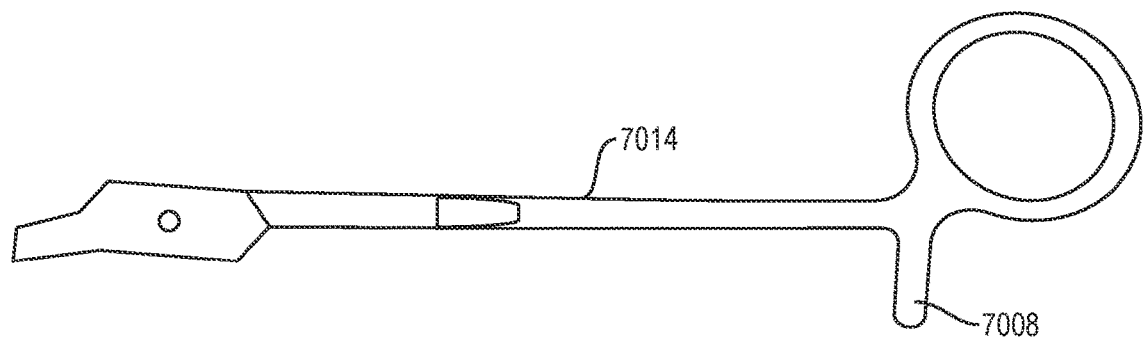
FIG. 70
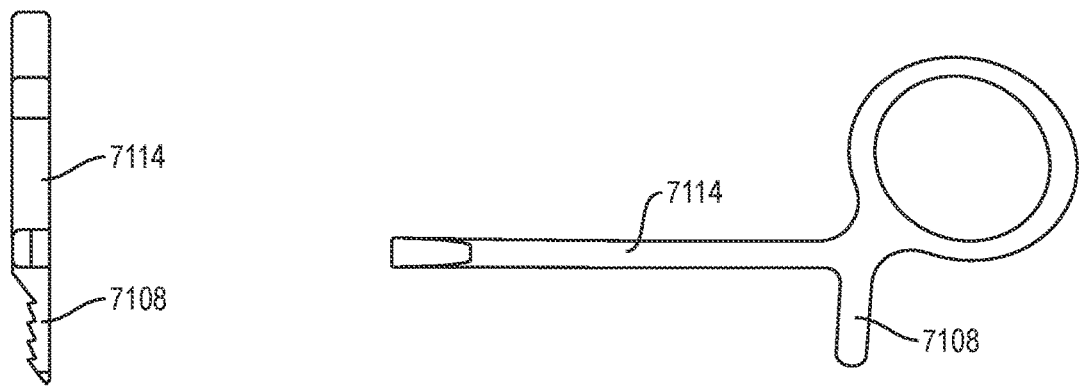
FIG. 71A
FIG. 71B
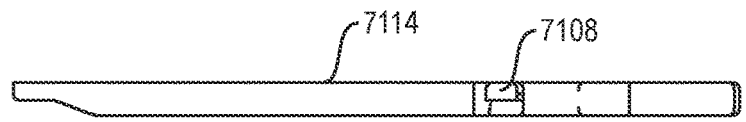
FIG. 71C

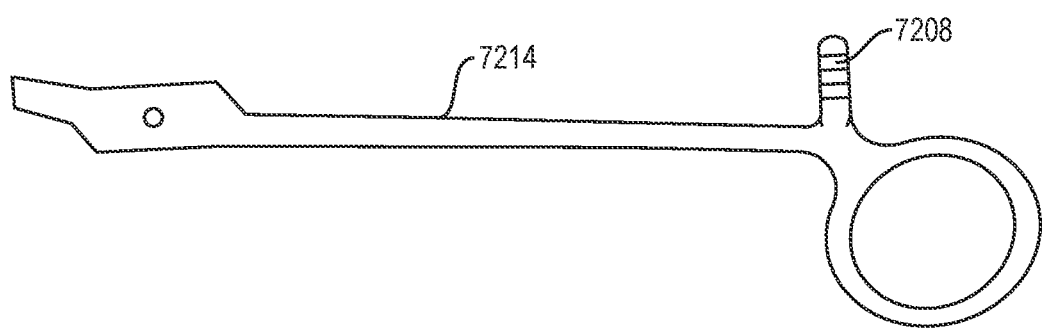
FIG. 72
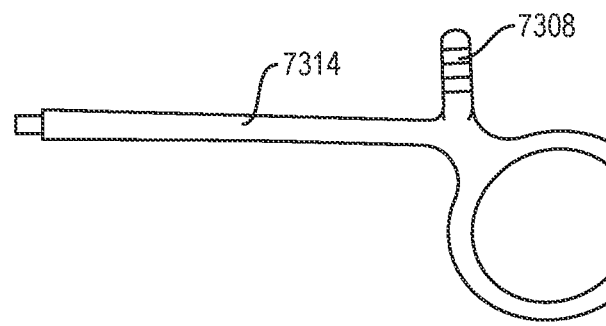
FIG. 73A
FIG. 73B

BIPLANAR FORCEPS REDUCERS AND METHODS OF USE

CROSS-REFERENCE TO RELATED APPLICATIONS

This application claims the benefit of U.S. Provisional Application No. 63/111,606, entitled "Biplanar Forceps Reducer," filed on Nov. 9, 2020. The entire contents of this application are hereby incorporated by reference in their entirety.

FIELD

This disclosure relates generally to surgical instruments and methods of use and, more particularly, to surgical instruments utilized to move one object relative to another, e.g., move a rod or spinal fixation element relative to an implanted bone anchor or other spinal fixation construct component during spine surgery.

BACKGROUND

During spine surgery, such as procedures to correct deformities in the spine, fixation constructs are often assembled to hold the spine in a desired shape. Such constructs often include a plurality of implanted bone anchors along multiple vertebrae and a connecting spinal fixation element, such as a rod, that is received within a head of each of the bone anchors and secured using a set screw. In many cases, the bone anchors are first implanted in the vertebrae, a rod is then positioned relative to the bone anchor heads, and set screws applied to secure the rod relative to each bone anchor.

It can be challenging to position the rod to be received in the head of each bone anchor. In some cases, a rod can be positioned offset from a bone anchor head both dorsally and medially-laterally such that the rod must be translated in both the sagittal plane and the coronal plane to capture it with the bone anchor head. This challenge can be particularly prevalent in procedures to correct deformities, as longer fixation constructs are often used along with uniplanar bone anchor heads that pivot in only one direction, though similar challenges can be faced when using bone anchor heads that move polyaxially as well.

Prior approaches to overcoming such challenges involve the use of multiple instruments. For example, a first instrument can be utilized to laterally translate a rod over a bone anchor head, and axial reduction of the rod into the bone anchor head can be performed with a second instrument. Often this is accomplished by attaching a lateral reducing instrument to a first bone anchor to move the rod over one or more bone anchors along a portion of a spinal fixation construct. An axial reducer can then be attached to an adjacent bone anchor and used to translate the rod axially into the bone anchor head.

Such prior approaches can have drawbacks. For example, use of instruments that can reduce, or translate, a rod in only one plane requires the use of additional instrumentation to complete a procedure. Further, since different reducing instruments are attached to different vertebral levels, load sharing among reducers is not possible. Still further, in some cases reducing instruments must be removed prior to set screw insertion due to interference with set screw insertion devices, or such devices must be loaded in a reducer instrument prior to loading a set screw. Both of these requirements can reduce flexibility and complicate a procedure. Finally, some prior instruments are too bulky to fit alongside adjacent instrumentation or around anatomy, especially when bone anchor heads are close together.

Accordingly, there is a need for improved instruments and methods for reducing or moving one component, such as a spinal fixation rod, relative to another component, such as a bone anchor, including improved instruments and methods for reducing or moving a component in multiple planes.

SUMMARY

Disclosed herein are biplanar forceps reducer instruments and methods of use that address these and other challenges of prior approaches. The biplanar forceps reducer instruments disclosed herein can engage an implant, such as a bone anchor receiver head, and reduce or move a spinal fixation element, such as a rod, in two planes to move the rod into a channel formed in the receiver head. Further, the biplanar forceps reducer instruments disclosed herein can allow for introduction and tightening of a set screw using an inserter that can pass through a cannulated tube of the reducer. The low profile and biplanar reduction functionality can allow a single type of reducer instrument to couple with each bone anchor along a spinal fixation construct and remain in position until the construct is secured in position.

In one aspect, a surgical instrument can include a first arm having a proximal end, a distal end, and a housing disposed therebetween, the housing including a threaded lumen defining a longitudinal axis. The instrument can also include a second arm having a proximal end and a distal end, the second arm pivotably coupled to the first arm. The instrument can further include a tube having a threaded outer surface portion disposed within the threaded lumen, a depth stop formed proximal to the threaded portion, and a drive feature at a proximal end of the tube configured to removably couple with a driver to impart torque to the tube. The instrument can also include a rod-engaging tip rotatably coupled to a distal end of the tube. Further, the first and second arms can be configured to translate a spinal fixation element laterally toward the longitudinal axis when pivoted toward one another and the rod-engaging tip can be configured to translate the spinal fixation element axially along the longitudinal axis when the tube is rotated relative to the housing.

Any of a variety of alternative or additional features can be included and are considered within the scope of the present disclosure. For example, in some embodiments, the depth stop can define a maximum outer diameter of the tube. In certain embodiments, the depth stop can be a shoulder formed around at least a portion of the circumference of the tube.

In some embodiments, the lumen can include continuous threads formed around a circumference thereof. Further, in certain embodiments an inner lumen of the tube can be accessible from a proximal end of the tube through the drive feature. Moreover, in some embodiments the rod-engaging tip can include an inner lumen coaxially disposed with the inner lumen of the tube.

In some embodiments, the rod-engaging tip can include an opening formed in a distal portion of a sidewall to facilitate viewing contents of an inner lumen of the rod-engaging tip.

In certain embodiments, a distal end of at least one of the first and second arms can include a protrusion configured to extend into a recess of a bone anchor receiver member. Further, the protrusion can be a pin disposed in a bore formed in the distal end of at least one of the first and second arms. In some embodiments, the protrusion can be a ridge extending across a width of the arm. The ridge or other protrusion can extend across an entire width of the arm or, in some embodiments, can extend across only a portion of a width of the arm or include one or more breaks along its length. In certain embodiments, the protrusion can be disposed proximal to a distal-most end of the arm and an inner surface of the arm distal to the protrusion can have a conical tapering profile. In some embodiments, the inner surface of the arm can include sidewalls extending outward from the inner surface at lateral ends of the arm, and opposed, inward-facing surfaces of each sidewall can have a planar tapering profile.

In certain embodiments, the instrument can further include a lock configured to selectively maintain a position of the first and second arms relative to one another. In some embodiments, the lock can be coupled to a proximal portion of one or more of the first and second arms, and a proximal end of the tube can be disposed distal to the lock.

In another aspect, a surgical method can include positioning a first arm of a reducer instrument against a bone anchor receiver member, as well as positioning a second arm of the reducer instrument against a spinal fixation element. The method can further include positioning a threaded outer surface portion of a tube of the reducer instrument within a threaded lumen formed in a housing of the first arm of the reducer instrument. The method can also include pivoting the first and second arms of the reducer instrument toward one another to translate the spinal fixation element laterally toward a longitudinal axis defined by the threaded lumen. The method can further include coupling a driver to a drive feature formed at a proximal end of the tube, and rotating the tube of the reducer instrument to translate the spinal fixation element axially along the longitudinal axis until a depth stop formed on the tube proximal to the threaded outer surface portion contacts the housing.

As with the instruments described above, the methods disclosed herein can include any of a variety of additional or alternative steps that are considered within the scope of the present disclosure. For example, in some embodiments the method can further include engaging a lock to maintain a position of the first and second arms relative to one another after pivoting the first and second arms toward one another.

In certain embodiments, the method can also include separating the driver from the proximal end of the tube after rotating the tube to translate the spinal fixation element axially. Further, the method can include inserting a set screw through an inner lumen of the tube and coupling the set screw with the receiver member. Still further, the method can include visually inspecting the set screw while coupled to the receiver member using an opening formed in a distal portion of a sidewall of rod-engaging tip coupled to the tube.

In another aspect, a surgical instrument can include a first arm having a proximal end, a distal end, and a housing disposed therebetween, the housing including a lumen defining a longitudinal axis, the lumen having continuous threads formed around a circumference thereof. The instrument can further include a second arm having a proximal end and a distal end, the second arm pivotably coupled to the first arm, and a tube having a threaded outer surface portion disposed within the lumen. The instrument can further include a rod-engaging tip rotatably coupled to a distal end of the tube, the rod-engaging tip being constrained against rotation relative to the housing by a protrusion coupled to the housing that is received in a recess of the rod-engaging tip. Further, the first and second arms can be configured to translate a spinal fixation element laterally toward the longitudinal axis when pivoted toward one another and the rod-engaging tip can be configured to translate the spinal fixation element axially along the longitudinal axis when the tube is rotated relative to the housing.

A number of additional or alternative features can be included. For example, in some embodiments, the threads on the outer surface portion of the tube can have a plurality of starts. In some embodiments, the threads on the outer portion of the tube can have three starts. Further, in certain embodiments an outer diameter of the threaded outer surface portion of the tube can be less than or equal to about 45% larger than a diameter of an inner lumen of the tube. In certain embodiments, an outer diameter of the threaded outer surface portion of the tube can be less than or equal to about 40%, about 35%, about 30%, about 25%, or about 20% larger than a diameter of an inner lumen of the tube. Utilizing such a configuration can minimize an outer diameter of the threads of the tube and provide a lower profile instrument to access a surgical site through a smaller opening or with less interference for adjacent anatomy or instrumentation.

In another aspect, a surgical instrument can include opposed arms pivotably coupled to one another, a tube threadably coupled to the opposed arms, and a rod-engaging tip rotatably coupled to the tube. Further, the opposed arms can be configured to laterally translate a spinal fixation element when pivoted toward one another and the rod-engagement tip can be configured to axially translate the spinal fixation element when the tube is rotated relative to the opposed arms and the rod-engagement tip.

As with the aspects and embodiments described above, a number of additional or alternative features are possible. For example, in some embodiments one of the opposed arms can include a housing having a threaded lumen formed therein. Further, in some embodiments the tube can include external threads formed thereon that interface with the threaded lumen of the body. The external threads formed on the tube can include a plurality of starts. In some embodiments, the external threads formed on the tube can include three starts. Further, in some embodiments an outer diameter of the external threads of the tube can be less than or equal to about 45% larger than a diameter of an inner lumen of the tube. In certain embodiments, an outer diameter of the threaded outer surface portion of the tube can be less than or equal to about 40%, about 35%, about 30%, about 25%, or about 20% larger than a diameter of an inner lumen of the tube. Utilizing such a configuration can minimize an outer diameter of the threads of the tube and provide a lower profile instrument to access a surgical site through a smaller opening or with less interference for adjacent anatomy or instrumentation.

In certain embodiments, the tube can include a depth stop formed proximal to the external threads. The depth stop can defines a maximum outer diameter of the tube in certain embodiments. The depth stop can have a variety of forms, and can be a shoulder formed around at least a portion of the circumference of the tube in some embodiments.

In some embodiments, the threaded lumen can include continuous threads formed around a circumference thereof. In certain embodiments the housing can include a protrusion received within a recess of the rod-engaging tip to constrain the rod-engaging tip against rotation relative to the housing.

In certain embodiments, the opposed arms can include opposed proximally-extending handles for user actuation. In some embodiments, the opposed arms can include a lock to maintain their relative position. The lock can include a ratchet in certain embodiments. In some such embodiments, the ratchet can be offset from a longitudinal axis of the tube. In certain embodiments, the lock can be coupled to a proximal portion of one or more of the opposed arms, and a proximal end of the tube can be disposed distal to the lock.

In some embodiments, the tube can include a drive feature formed at a proximal end thereof to facilitate rotation of the tube. In certain embodiments, an inner lumen of the tube can be accessible from a proximal end of the tube through the drive feature. In some embodiments, the rod-engaging tip can include an inner lumen that is coaxial with the inner lumen of the tube. In certain embodiments, the rod-engaging tip can include an opening formed in a distal portion of a sidewall to facilitate viewing contents of the inner lumen of the rod-engaging tip.

In certain embodiments, a distal end of at least one of the opposed arms can include an engagement feature configured to interface with a complementary feature of a bone anchor receiver member. In some embodiments, the engagement feature can include a protrusion configured to extend into a recess of a bone anchor receiver member. For example, the protrusion can be a pin disposed in a bore formed in the distal end of the arm, or a ridge extending across a width of the arm. The ridge or other protrusion can extend across an entire width of the arm or, in some embodiments, can extend across only a portion of a width of the arm or include one or more breaks along its length. In some embodiments, the engagement feature can be disposed proximal to a distal-most end of the arm and an inner surface of the arm distal to the protrusion can have a conical tapering profile. Further, in certain embodiments the inner surface of the arm can include sidewalls extending outward from the inner surface at lateral ends of the arm, and opposed, inward-facing surfaces of each sidewall can have a planar tapering profile.

In another aspect, a surgical method can include positioning a first arm of a reducer instrument against a bone anchor receiver member, and positioning a second arm of the reducer instrument against a spinal fixation element. The method can further include pivoting the first and second arms of the reducer instrument toward one another to laterally translate the rod toward the receiver member, and rotating a tube of the reducer instrument to axially translate the spinal fixation element toward the receiver member.

A number of additional or alternative steps can be included. For example, in some embodiments, the method can further include inserting a set screw through a lumen formed in the tube and coupling the set screw to the receiver member. Further, the method can include visually inspecting the set screw while coupled to the receiver member using an opening formed in a distal portion of a sidewall of a rod-engaging tip coupled to the tube.

In certain embodiments, the method can also include locking a position of the first and second arms relative to one another.

In some embodiments, the method can include positioning a threaded outer surface portion of the tube within a threaded lumen formed in a housing coupled to one or more of the first arm and the second arm. In certain embodiments, rotating the tube can be continued until a depth stop formed on the tube proximal to the threaded outer surface portion contacts the housing.

In some embodiments, the method can further include coupling a driver to a drive feature formed at a proximal end of the tube prior to rotating the tube to axially translate the spinal fixation element. The method can also include separating the driver from the proximal end of the tube after rotating the tube to axially translate the spinal fixation element.

In certain embodiments, the method can also include engaging a lock to maintain a position of the first and second arms relative to one another after pivoting the first and second arms toward one another.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which:

FIG. 37 is a perspective view of a set screw being inserted through the instrument of FIG. 28;

FIG. 38 is another perspective view of a set screw being inserted through the instrument of FIG. 28;

FIG. 43A is a perspective view of one embodiment of a biplanar forceps reducer according to the present disclosure;

FIG. 43B is an end view of the instrument of FIG. 43A;

FIG. 43C is a detail view of the instrument of FIG. 43B;

FIG. 43D is a top view of the instrument of FIG. 43A;

FIG. 44A is a longitudinal cross-sectional view of the instrument of FIG. 43A;

FIG. 44B is a detail view of a middle portion of FIG. 44A;

FIG. 45 is a partial-exploded view of the instrument of FIG. 43A;

FIG. 46 is another partial-exploded view of the instrument of FIG. 43A;

FIG. 47A is a perspective view of one embodiment of a pin used to couple a reducer tube and rod-engaging reducer tip according to the present disclosure;

FIG. 47B is a side view of the pin of FIG. 47A;

FIG. 47C is an end view of the pin of FIG. 47A;

FIG. 48A is an end view of one embodiment of a thrust washer according to the present disclosure;

FIG. 48B is a side view of the thrust washer of FIG. 48A;

FIG. 48C is a perspective view of the thrust washer of FIG. 48A;

FIG. 49A is an end view of one embodiment of a pin used to couple opposing forceps arms according to the present disclosure;

FIG. 49B is a side view of the pin of FIG. 49A;

FIG. 49C is a perspective view of the pin of FIG. 49A;

FIG. 50A is a perspective view of a reducer tube and rod-engaging reducer tip of the instrument of FIG. 43A;

FIG. 50B is a side view of a reducer tube and rod-engaging reducer tip of the instrument of FIG. 43A;

FIG. 51A is a longitudinal cross-sectional view of a reducer tube and rod-engaging reducer tip of the instrument of FIG. 43A;

FIG. 51B is a detail view of a middle portion of FIG. 51A;

FIG. 57A is a perspective view of a forceps body of the instrument of FIG. 43A;

FIG. 57B is a first end view of a forceps body of the instrument of FIG. 43A;

FIG. 57C is a second end view of a forceps body of the instrument of FIG. 43A;

FIG. 57D is a side view of a forceps body of the instrument of FIG. 43A;

FIG. 57E is top view of a forceps body of the instrument of FIG. 43A;

FIG. 57F is a third end view of a forceps body of the instrument of FIG. 43A;

FIG. 57G is a detail view of a distal portion of FIG. 57E;

FIG. 58A is a longitudinal cross-sectional view of a forceps body of the instrument of FIG. 43A;

FIG. 58B is a detail view of a distal portion of FIG. 58A;

FIG. 62D is an end view of a first forceps arm of the instrument of FIG. 43A;

FIG. 63A is a side view of a second forceps arm of the instrument of FIG. 43A;

FIG. 63B is a bottom view of a second forceps arm of the instrument of FIG. 43A;

FIG. 63C is a top view of a second forceps arm of the instrument of FIG. 43A;

FIG. 63D is another side view of a second forceps arm of the instrument of FIG. 43A;

FIG. 63E is a perspective view of a second forceps arm of the instrument of FIG. 43A;

FIG. 64 is an exploded view of a second forceps arm of the instrument of FIG. 43A;

FIG. 65D is a side view of a pivot arm of the instrument of FIG. 43A;

FIG. 65E is a second end view of a pivot arm of the instrument of FIG. 43A;

FIG. 66A is a transverse cross-sectional view of a pivot arm of the instrument of FIG. 43A;

FIG. 66B is a detail view of an end of FIG. 66A;

FIG. 67A is a longitudinal cross-sectional view of a pivot arm of the instrument of FIG. 43A;

FIG. 67B is a detail view of a distal portion of FIG. 66A;

FIG. 68A is a side view of a pin used to aid coupling a forceps arm with a bone screw according to the present disclosure;

FIG. 68B is an end view of the pin of FIG. 68A;

FIG. 68C is a top view of the pin of FIG. 68A;

FIG. 69A is an end view of pin used to prevent rotation of a rod-engaging reducer tip according to the present disclosure;

FIG. 69B is a side view of the pin of FIG. 69A;

FIG. 69C is a top view of the pin of FIG. 69A;

FIG. 70 is a side view of a forceps handle according to the present disclosure;

FIG. 71A is an end view of a forceps handle according to the present disclosure;

FIG. 71B is a side view of a forceps handle of FIG. 71A;

FIG. 71C is a top view of a forceps handle of FIG. 71A;

FIG. 72 is a side view of a forceps handle according to the present disclosure;

FIG. 73A is an end view of a forceps handle according to the present disclosure; and FIG. 73B is a side view of a forceps handle of FIG. 73A.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Disclosed herein are biplanar forceps reducer instruments and methods of use that can facilitate engaging an implant, such as a bone anchor receiver head, and reducing or moving a spinal fixation element, such as a rod, in two planes to move the rod into a channel formed in the receiver head. Further, the biplanar forceps reducer instruments disclosed herein can allow for introduction and tightening of a set screw using an inserter that can pass through a cannulated tube of the reducer. The low profile and biplanar reduction functionality can allow a single type of reducer instrument to couple with each bone anchor along a spinal fixation construct and remain in position until the construct is secured in position.

Figure 1A:
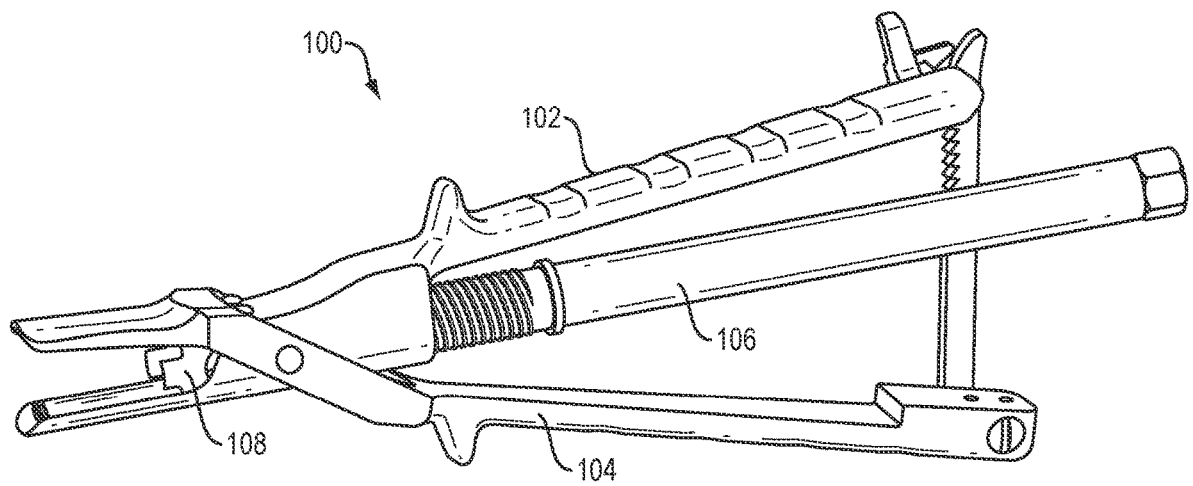
FIG. 1A is a perspective view of one embodiment of a biplanar forceps reducer instrument of the present disclosure.
Figure 1B:
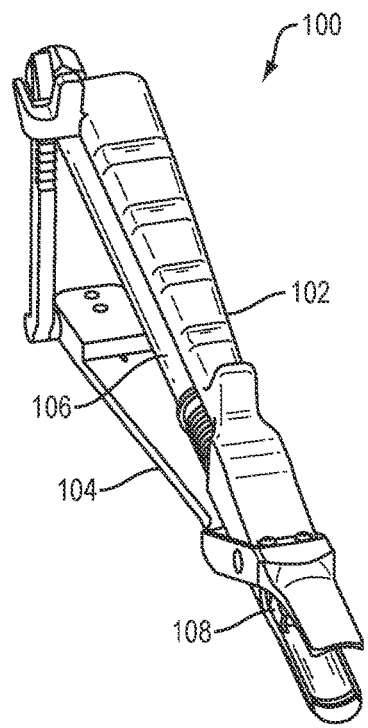
FIG. 1B is another perspective view of the instrument of FIG. 1A.

FIGS. 1A and 1B illustrate one embodiment of a biplanar forceps reducer instrument 100 according to the present disclosure. The instrument 100 includes a first arm 102 and a second arm 104 that are pivotably coupled to one another, as well as a reducer tube 106 threadably coupled to the opposed first and second arms and a rod-engaging tip 108 that is rotatably coupled to the reducer tube. As explained in more detail below, the instrument 100 operates by using the opposed first and second arms 102, 104 to capture a spinal fixation element, such as a rod, and a bone anchor, such as a proximal receiver member of a bone anchor assembly. The instrument 100 can reduce, or translate, the rod in multiple dimensions, e.g., laterally and axially. By way of example, a user can squeeze the proximal portions of the first and second arms 102, 104 toward one another to cause the distal portions thereof to also move toward one another. Contacting one arm to a spinal fixation element and the other to a bone anchor can allow the lateral reduction or translation of the rod into alignment over the bone anchor. Subsequently, the tube 106 can be rotated, which can result in distal translation of the rod-engaging tip 108 rotatably coupled thereto. The rod-engaging tip 108 can contact the rod and reduce or translate it distally into, e.g., a rod-receiving seat of the bone anchor. Finally, a rod locking element, such as a set screw, can be introduced to the bone anchor through a lumen formed in the reducer tube 106 and rod-engaging tip 108.

Figure 2:
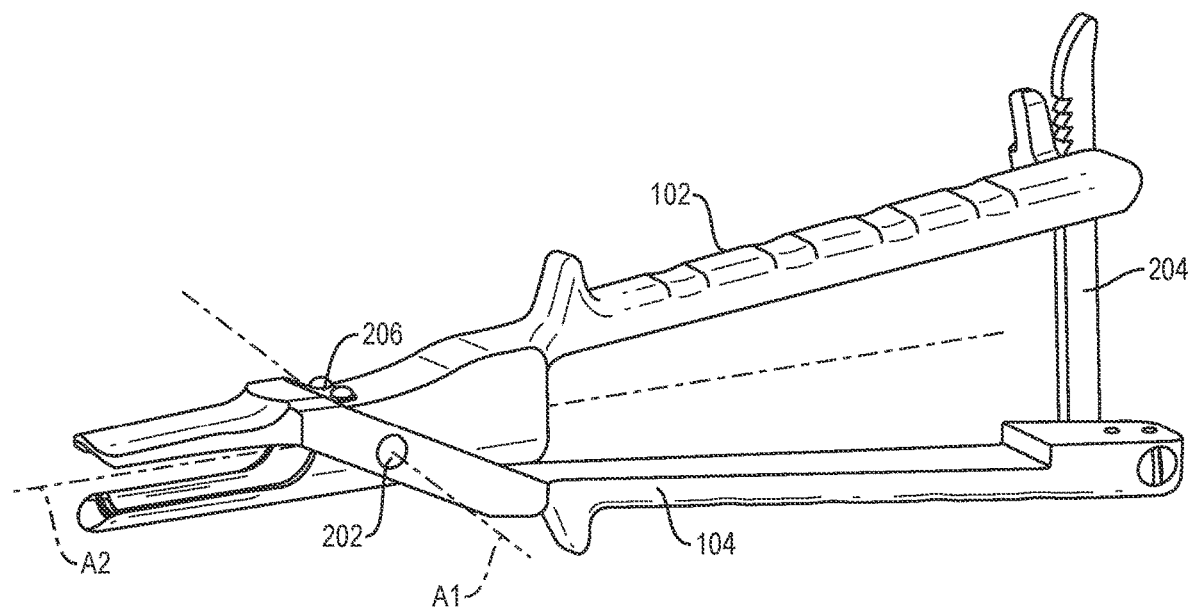
FIG. 2 is a perspective view of opposed forceps arms of the instrument of FIG. 1A.
Figure 3:
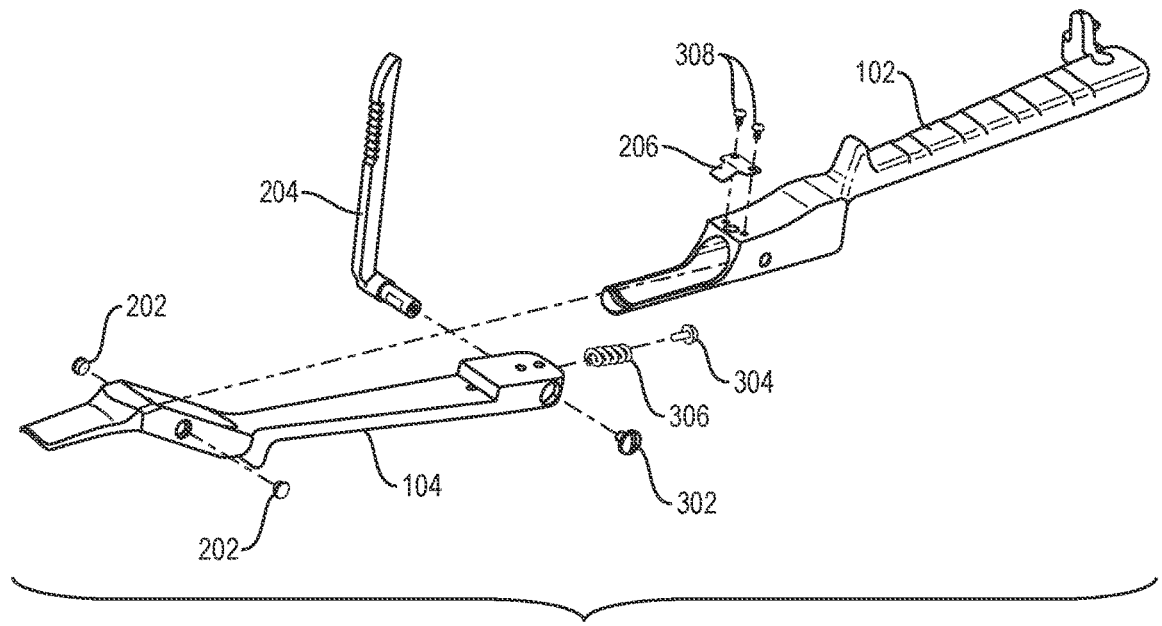
FIG. 3 is an exploded view of the opposed forceps arms of FIG. 2.

FIG. 2 illustrates the opposed first and second arms 102, 104 in isolation, and FIG. 3 shows an exploded view of the assembly. The first and second arms 102, 104 are pivotably coupled with one another by pins 202 that allow the arms to pivot relative to one another about an axis A1 that is transverse to a longitudinal axis A2 of the instrument. The opposed outer handles of the instrument can also include a lock 204 configured to maintain a relative position of the handles or arms, and a biasing element 206 that can be configured to bias the arms in a desired direction. For example, in the illustrated embodiment a portion of the lock 204 can be coupled to a proximal end of the second arm 104 using a screw 302. A leaf spring 206 can be utilized as a biasing element and secured to the first arm 102 using screws 308. The leaf spring 206 can contact a portion of the second arm 104 to urge the first and second arms into an open configuration relative to one another. FIG. 3 also illustrates a mechanism that can be utilized to provide friction and maintain a position of a portion of the lock 204 until, e.g., positively moved by a user. The mechanism can include a pin 304 disposed in a bore formed in the second arm 104 such that one end of the pin is in contact with a portion of the lock 204. A coil spring 306 or other biasing element can urge the pin 304 against the portion of the lock 204 to provide a friction or drag force against movement of the lock relative to the second arm 104. This mechanism is illustrated in greater detail in FIG. 5.

FIGS. 4A-4E illustrate the second arm 104 in greater detail. The second arm 104 can include a distal portion 402 configured to contact a spinal fixation element and/or bone anchor, a pivot arm 404, a proximal handle 406, and a proximal end portion 408 that can include the lock 204. Also shown in these figures is the ratchet bar 410 of the lock 204.

The proximal handle 406 of the second arm 104 can include a number of different features to facilitate a user grasping and manipulating the handle. For example, the proximal handle 406 can include one or more depressions 411 configured to seat a user's fingers. In some embodiments, the proximal handle 406 of the second arm 104 can include one or more finger loops configured to receive a user's fingers, as shown, for example, in FIGS. 28, 39, 42, and 43. In still other embodiments, the proximal handle 406 can include grip or comfort-enhancing features, such as a silicone or other material overmolded portion to facilitate grasping. In some embodiments, the proximal handle 406 can also include one or more protrusions configured to assist user's in maintaining their grip when imparting axial forces to the instrument 100. For example, the second arm 104 includes a protrusion 413 formed at a distal position along the handle 406 to prevent a user's hand from slipping off the handle when, e.g., urging the instrument distally to couple with a bone anchor receiver member.

The pivot arm 404 can extend at an oblique angle relative to longitudinal axes defined by the distal portion 402 and the proximal handle 406. The pivot arm 404 can also define a recess 415 between opposed struts 417 that can receive the first arm 102 therethrough during assembly and operation. The opposed struts 417 can include bores to receive the pins 202 that pivotably couple the first and second arms 102, 104.

The distal portion 402 can have a curved profile to accommodate passage of the reducer tube 106 and/or rod-engaging tip 108, as well as to facilitate coupling with a bone anchor receiver member that can have a generally curved shape at the interface between the two components. The distal portion 402 can also include an engagement feature 412 formed along a distal portion thereof that can be configured to interface with a complementary feature on a bone anchor receiver member to facilitate coupling between the two components.

Figure 4A:
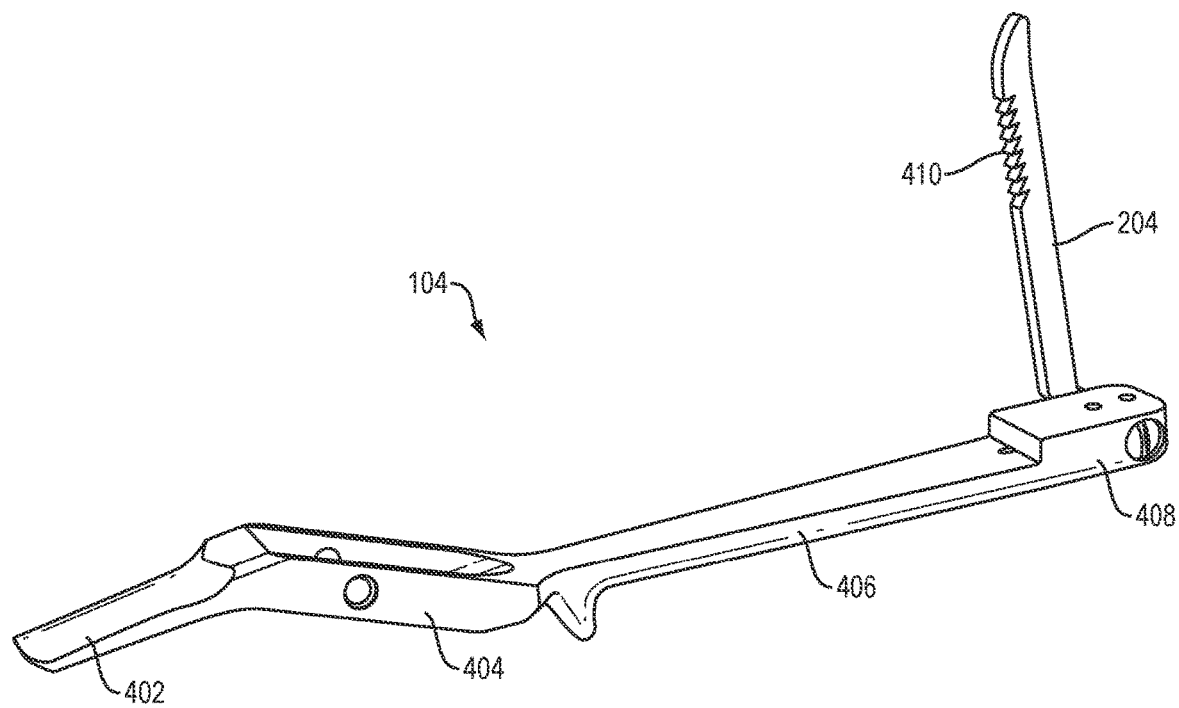
FIG. 4A is a top perspective view of a first forceps arm of the instrument of FIG. 1A.
Figure 4B:
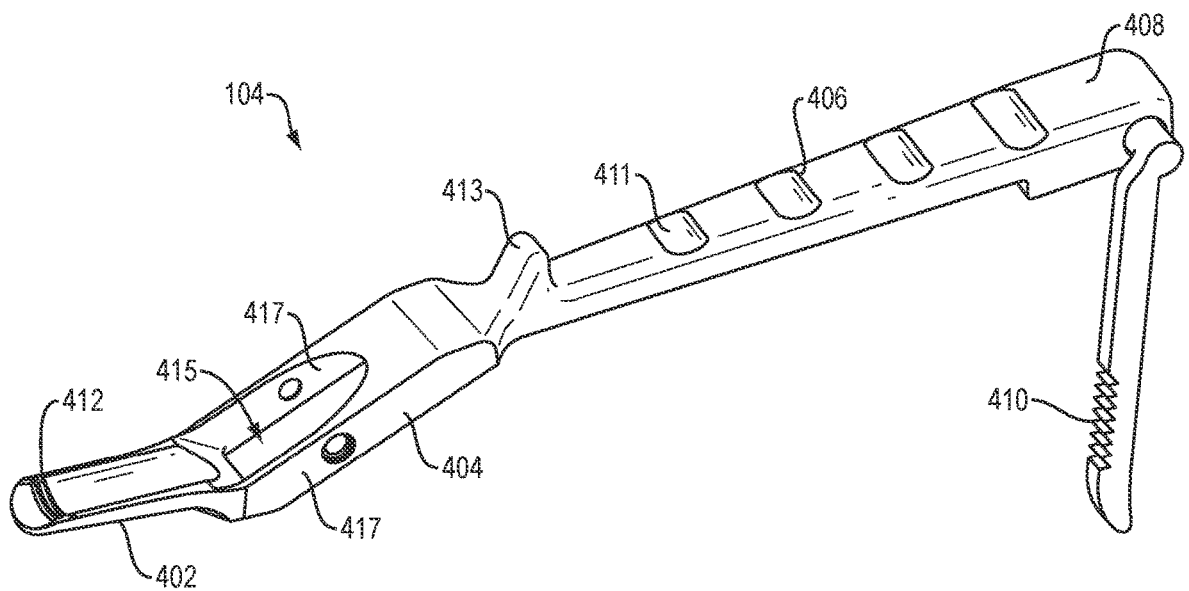
FIG. 4B is a bottom perspective view of a first forceps arm of FIG. 4A.
Figure 4C:
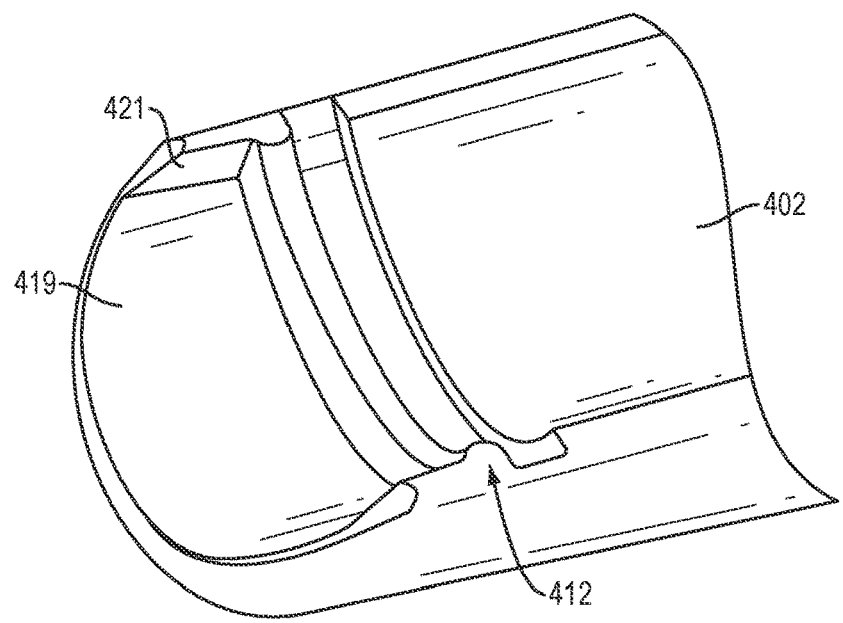
FIG. 4C is a detail perspective view of a distal portion of FIG. 4B.
Figure 4D:
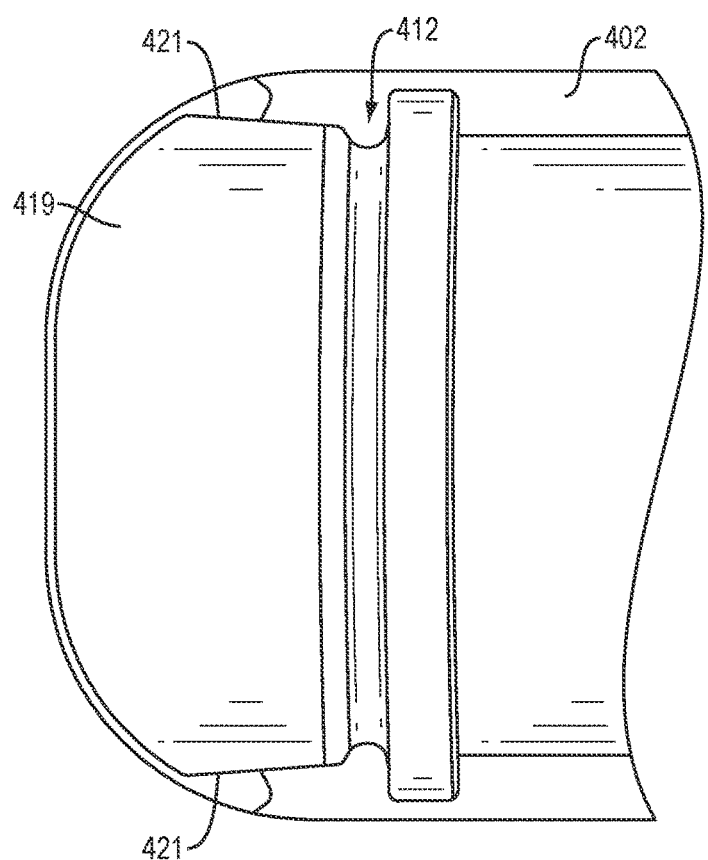
FIG. 4D is a detail top view of a distal portion of FIG. 4B.
Figure 4E:
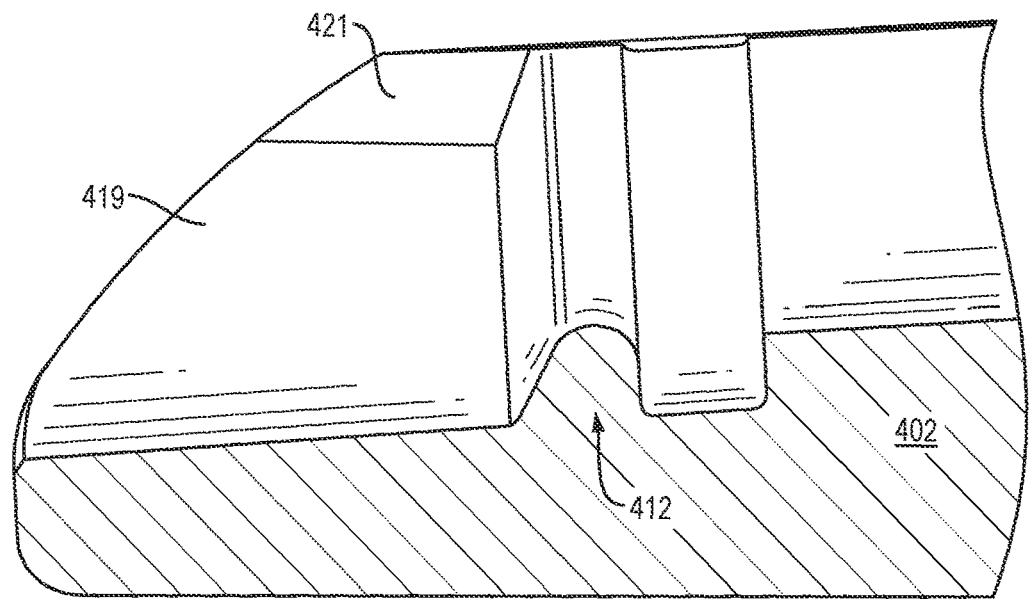
FIG. 4E is a detail longitudinal cross-sectional view of a distal portion of FIG. 4B.

FIGS. 4C-4E illustrate the distal end of the distal portion 402 in greater detail. As shown in the figures, the engagement feature 412 can be a protrusion 412, such as a ridge extending across a width of the arm, that can be configured to be received within a slot or other recess formed in a proximal outer surface portion of a bone anchor receiver member to facilitate coupling between the components. The ridge or other protrusion can extend across an entire width of the arm or, in some embodiments, can extend across only a portion of a width of the arm or include one or more breaks along its length. Example bone anchors having such features are described in U.S. Pat. No. 7,179,261, the entire contents of which are incorporated by reference herein. Other engagement feature configurations are possible as well, including reversing the above-described configuration such that a protrusion formed on a bone anchor is received in a recess formed in the distal portion 402. It is also possible to utilize other geometries, e.g., a pin extending from the inner surface of the distal portion 402 that can be received within a bore formed in a receiver member of a bone anchor. An example of a pin disposed in a bore formed in the distal portion 402 can be seen in the embodiment of FIG. 43.

In some embodiments, the engagement feature 412 can be disposed proximal to a distal-most end of the arm's distal portion 402 and an inner surface of the arm distal to the engagement feature can be configured to facilitate alignment and coupling of the instrument with a bone anchor receiver member. For example, an internal surface 419 of the arm can have a shape or profile that is complementary to an outer surface of the bone anchor in order to facilitate coupling even in the event there is some amount of misalignment, whether that be, e.g., lateral or rotational misalignment along an axis of a rod, rotational misalignment along a longitudinal axis of the instrument 100, etc. In some embodiments, for example, the inner surface 419 can include a tapered profile complementary to an outer surface of opposed arms of a polyaxial bone anchor receiver head. In some instances, the inner surface 419 can include a conical tapering profile that is complementary to the conical tapering profile of a receiver member. Such an arrangement can allow for some pivoting misalignment between the receiver head and the instrument 100 that can be corrected as the instrument is advanced distally relative to the receiver head. In other embodiments, however, the profile can be flat without any tapering. Even in such a configuration, the additional extension of the distal portion of the arm beyond the engagement feature 412 can facilitate alignment and coupling between the instrument 100 and a bone anchor receiver member.

Figure 5:
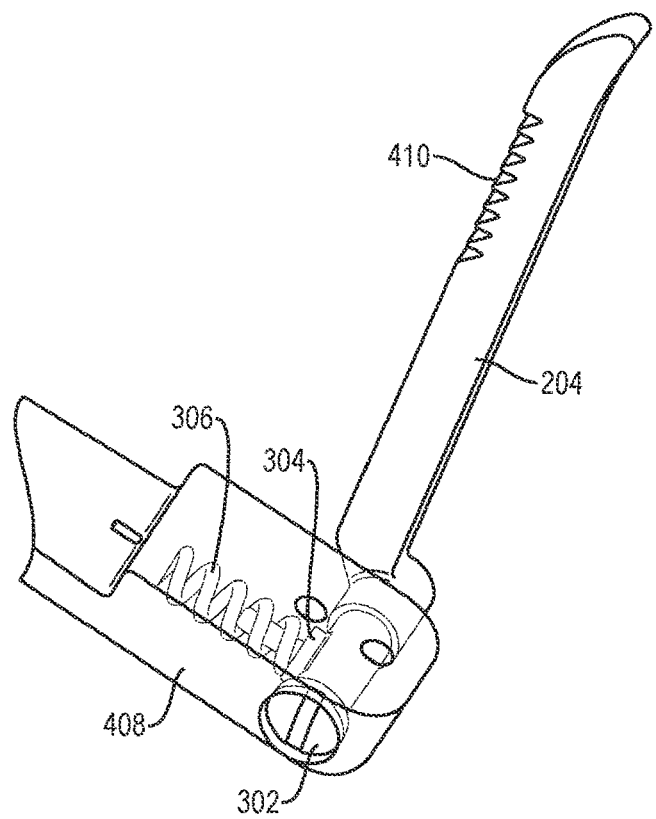
FIG. 5 is a partially-transparent detail view of a proximal portion of the forceps arm of FIG. 4A.
Figure 6A:
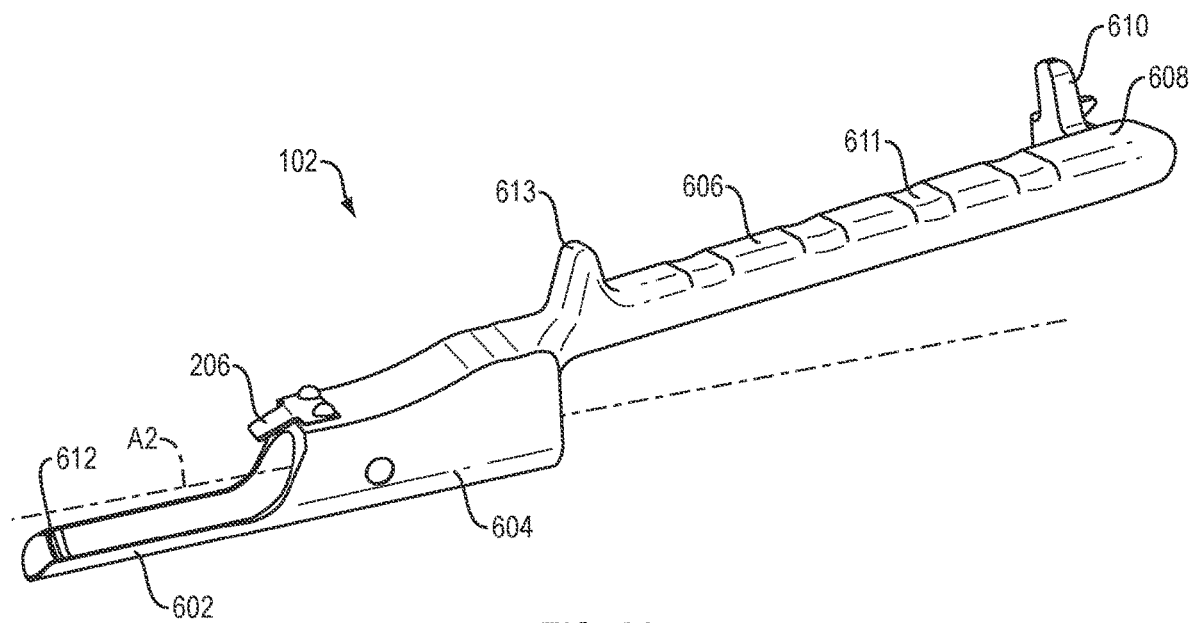
FIG. 6A is a top perspective view of a second forceps arm of the instrument of FIG. 1A.
Figure 6B:
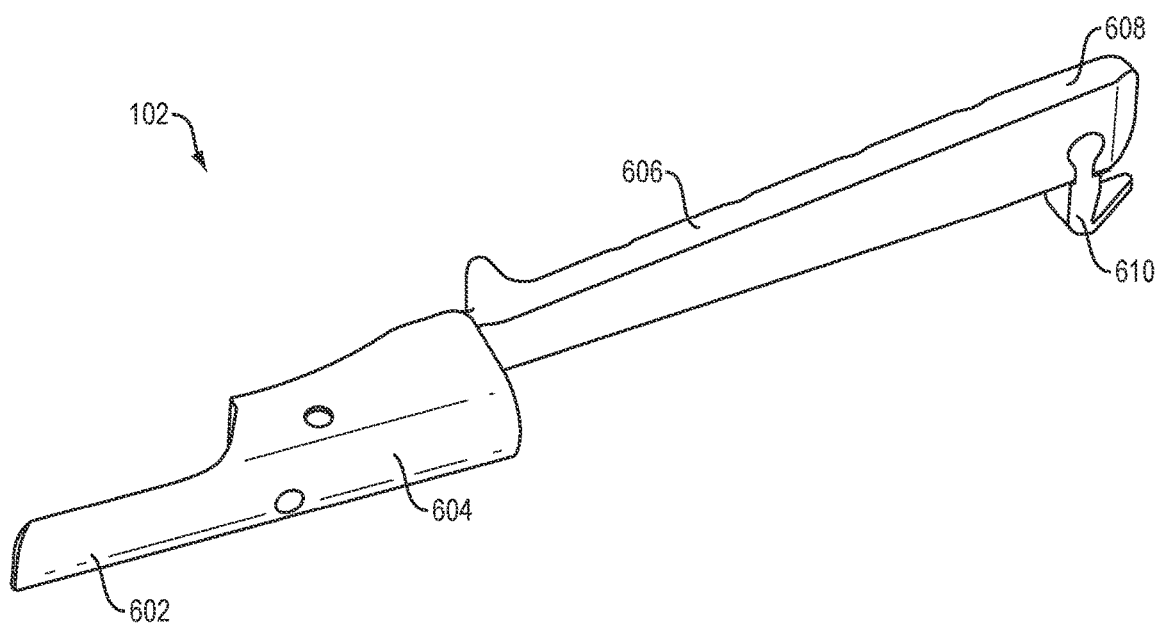
FIG. 6B is a bottom perspective view of a second forceps arm of FIG. 6A.
Figure 6C:
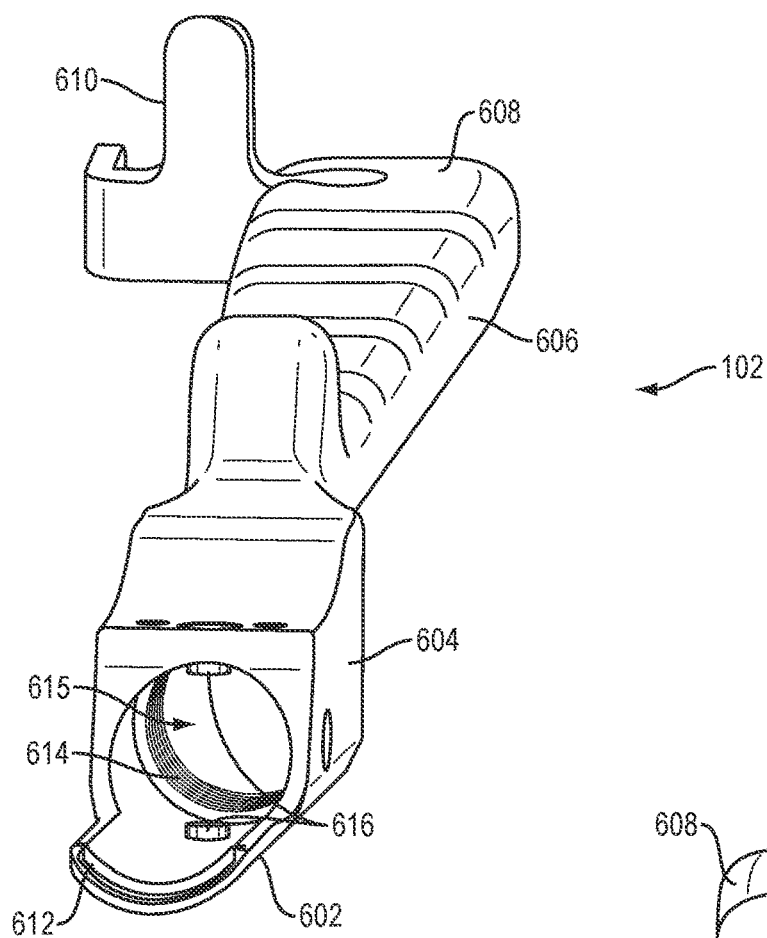
FIG. 6C is a front perspective view of a second forceps arm of FIG. 6A.
Figure 6D:
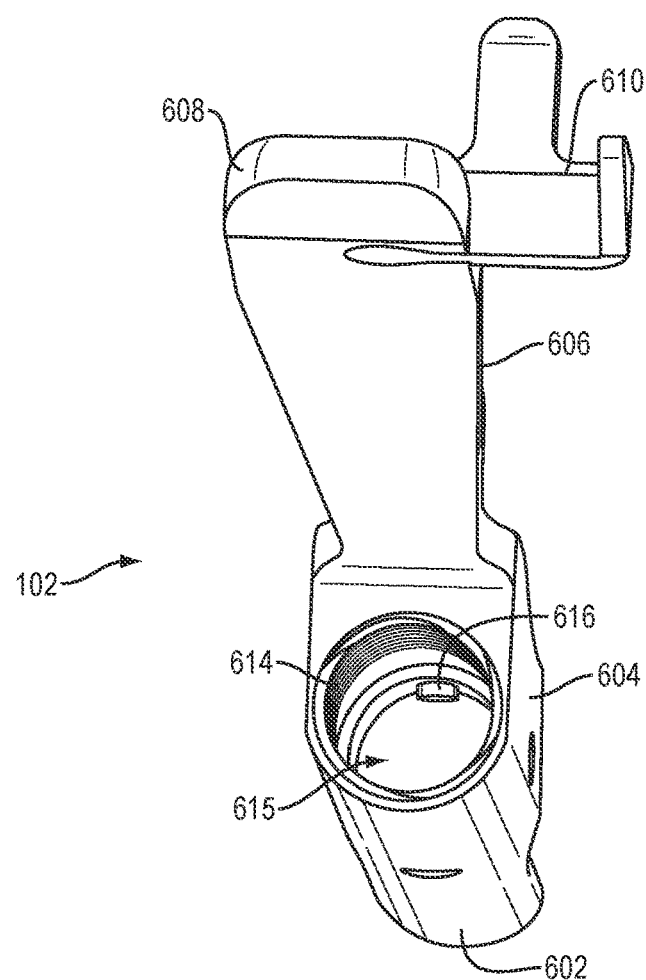
FIG. 6D is a rear perspective view of a second forceps arm of FIG. 6A.
Figure 6E:
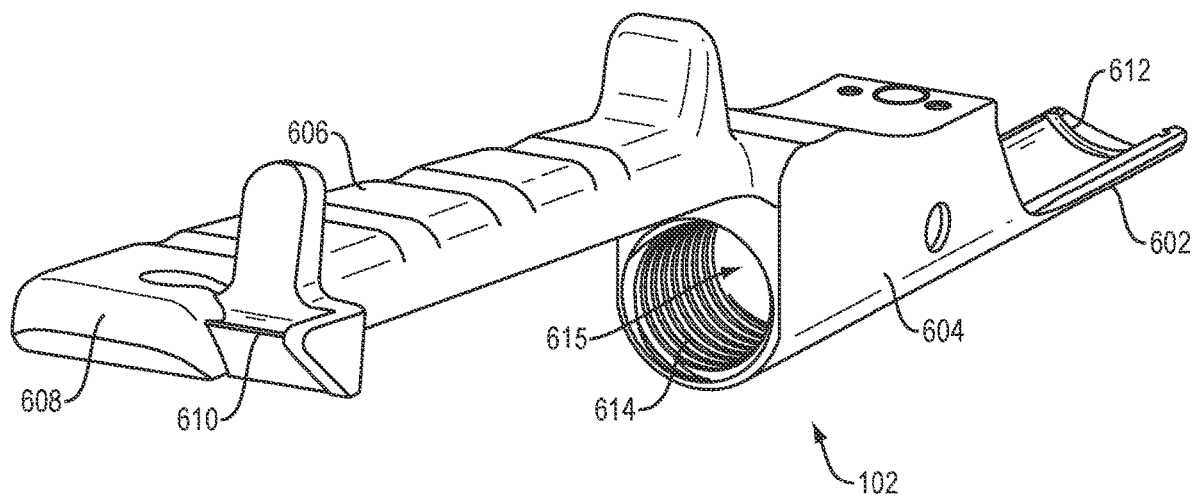
FIG. 6E is another rear perspective view of a second forceps arm of FIG. 6A.
Figure 6F:
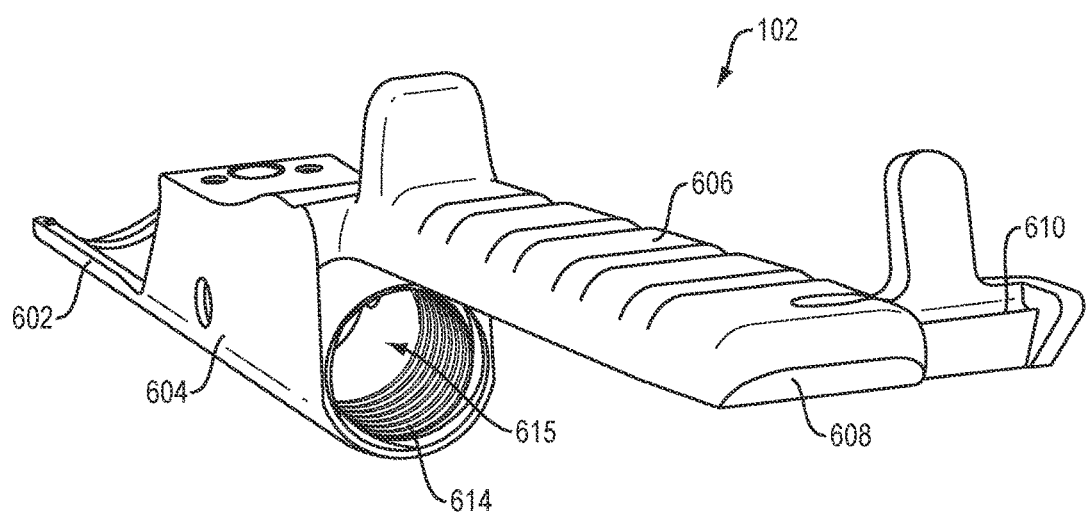
FIG. 6F is another rear perspective view of a second forceps arm of FIG. 6A.

FIG. 5 illustrates the portion of the lock 204 coupled to the second arm 104 in greater detail. As noted above, the lock 204 can include a ratchet bar 410 rotatably coupled to the proximal portion 408 of the second arm 104 by being disposed in a bore formed in the proximal portion of the second arm and secured with screw 302. In addition, a drag or friction force can be applied to the ratchet bar 410 using a pin 304 disposed in a transversely-oriented bore formed in the proximal portion 408 of the second arm 104. The pin 304 can be urged against a portion of the ratchet bar 410 using a coil spring 306 or other biasing element.

FIGS. 6A-6F illustrate the first arm 102 in greater detail. The first arm 102 can include a distal portion 602, a housing 604, a proximal handle 606, and a proximal end 608 that include a catch 610 that forms a complementary portion of the lock 204 and interfaces with the ratchet bar 410. The distal portion 602 can be similar to the distal portion 402 of the second arm 104 described above, including an engagement feature 612 and similarly configured surface profiles to facilitate coupling with a bone anchor receiver member. Similarly, the proximal handle 606 can be a mirror or similarly configured as the proximal handle 406 of the second arm 104 described above, including the use of features like finger-recesses 611 and a protrusion 613 to assist during application of axial forces to the first arm 102.

The housing 604 can include a lumen 615 having threads 614 formed along at least a portion of a surface thereof. The lumen 615 can define the longitudinal axis A2 of the instrument 100, or at least the longitudinal axis A2 along which the reducer tube 106 and rod-engaging tip 108 translate during reduction maneuvers. The threads 614 formed on the surface of the lumen 615 can be continuous and extend around a circumference thereof, i.e., around an entire perimeter of the lumen 615. This can be in contrast to partial-circumference thread forms interrupted by longitudinal slots, etc. In some embodiments, however, such a configuration could be utilized in connection with a biplanar forceps reducer according to the present disclosure, e.g., to prevent rotation of a rod-engaging tip without using protrusions formed on the housing 604. More details on such a configuration and other features can be found in U.S. Pat. No. 8,647,347, the entire contents of which are incorporated by reference herein.

The lumen 615 of the housing 604 can also include one or more protrusions 616 extending from a surface thereof at a position distal to the threads 614. As explained in more detail below, the one or more protrusions 616 can be received within a recess of the rod-engaging tip 108 to prevent relative rotation between the tip and the first arm 102. Other configurations are also possible, however, including, for example, a feature formed along the distal portion 602 rather than in the housing 604, any of a variety of cooperating shapes, protrusions, and recesses that can prevent relative rotation, etc.

Figure 7:
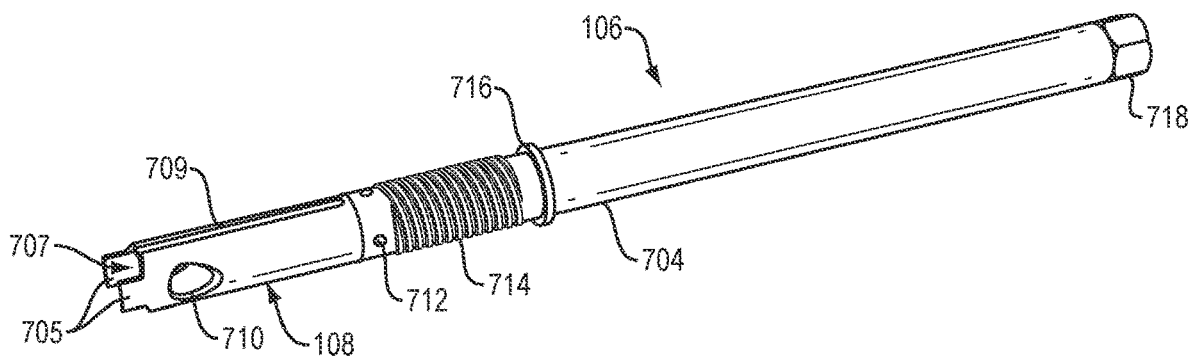
FIG. 7 is a perspective view of a reducer tube and rod-engaging reduction tip of the instrument of FIG. 1A.
Figure 8:
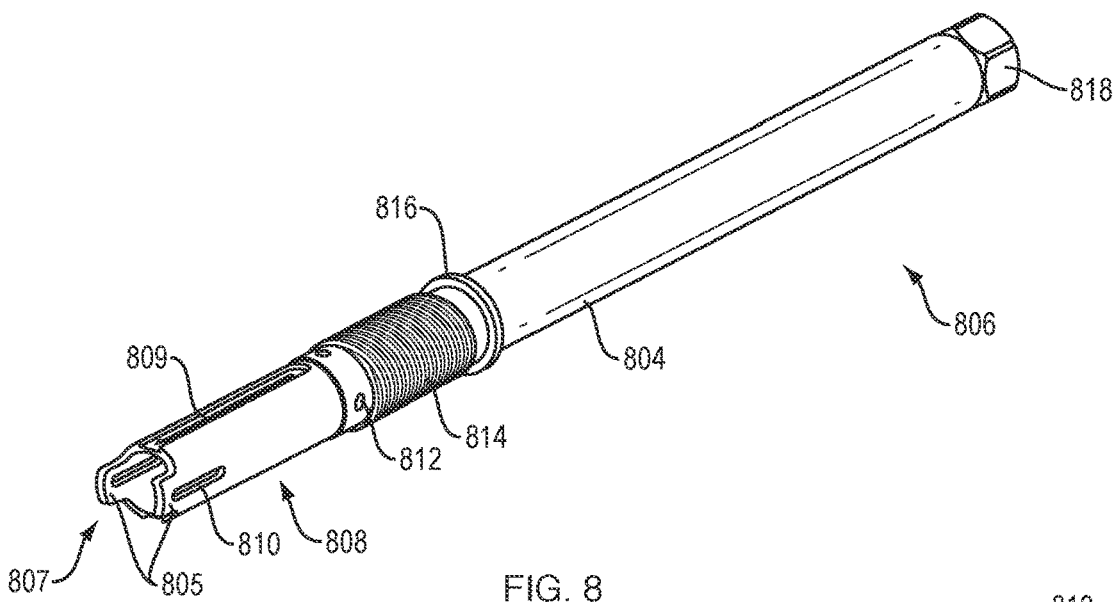
FIG. 8 is a perspective view of another embodiment of a reducer tube and rod-engaging reduction tip according to the present disclosure.

FIG. 7 illustrates the reducer tube 106 and rod-engaging tip 108 in greater detail. The reducer tube 106 is rotatably coupled to the rod-engaging tip 108, i.e., the two components can rotate relative to one another but are prevented from axially translating relative to one another. The rod-engaging tip 108 can include opposed extensions 705 formed at a distal end thereof that can be sized and shaped to contact a spinal fixation element, such as a rod, during an axial reduction maneuver. The extensions 705 can also be configured to extend into a U-shaped gaps formed between opposed arms of a bone anchor receiver member, such that the rod-engaging tip 108 can axially reduce a rod into the receiver member without interfering with delivery of a set screw or other locking element, as described below. Also to facilitate delivery of a set screw or other locking element, the rod-engaging tip 108 and reducer tube 106 can define an inner lumen 707, and the portions thereof extending through each component 106, 108 can be coaxially aligned.

The rod-engaging tip 108 can also include one or more openings 710 formed in a sidewall to facilitate viewing into the lumen 707. This can be useful to facilitate visualizing placement of a set screw or locking element delivered through the lumen 707, as described in more detail below.

The rod-engaging tip 108 can also include a groove 709 or other recess formed in an outer surface thereof and extending at least partially along a length thereof. The groove 709 can receive the protrusion 616 formed on the surface of the lumen 615 of the housing 604 in order to prevent relative rotation between the tip 108 and the first arm 102.

As noted above, the reducer tube 106 and rod-engaging tip 108 can be rotatably coupled in a manner that permits relative rotation while preventing relative axial translation between the components. This can be accomplished using pins 712 disposed through bores formed in the reducer tube 106 and extending into an interior of the reducer tube. The pins can be received within a groove formed in a proximal end of the rod-engaging tip 108, as described in more detail below.

The reducer tube 106 can include a threaded outer surface portion 714 configured to interface with the threads 614 formed on the surface of the lumen 615 of the housing 604. A depth stop 716 can be formed on the reducer tube 106 at a position proximal to the threads 714. The depth stop 716 can be configured to contact a proximal portion of the housing 604 in order to limit the distal advancement of the reducer tube 106 and rod-engaging tip 108 relative to the first and second arms 102, 104. This depth can be configured to allow for the reduction of multiple diameter spinal fixation rods, e.g., 5.5 mm and 6 mm diameter rods, while providing sufficient reduction to allow a set screw or other locking element to engage a receiver member (e.g., threads of a set screw to engage with threads formed on a proximal surface of a receiver member) and prevent excessive reduction that can create tension and inhibit easy decoupling of the instrument from the receiver member after the set screw or other locking element is installed. For example, in some embodiments the depth stop can be positioned to provide about 6.5 mm of clearance between a distal end of the rod-engaging tip 108 and the base of a bone anchor receiver member rod slot at maximum axial reduction when the depth stop 716 contacts the housing 604. Such a configuration can allow using the device with both 5.5 mm and 6 mm rods with the benefits noted above. The depth stop 716 can have a variety of forms, including any of a variety of protrusions formed on an outer surface of the reducer tube 106 around part of or an entirety of its circumference. In the illustrated embodiment, the depth stop 716 is a shoulder formed around a circumference (i.e., an entire perimeter) of the reducer tube 106.

Figure 11A:
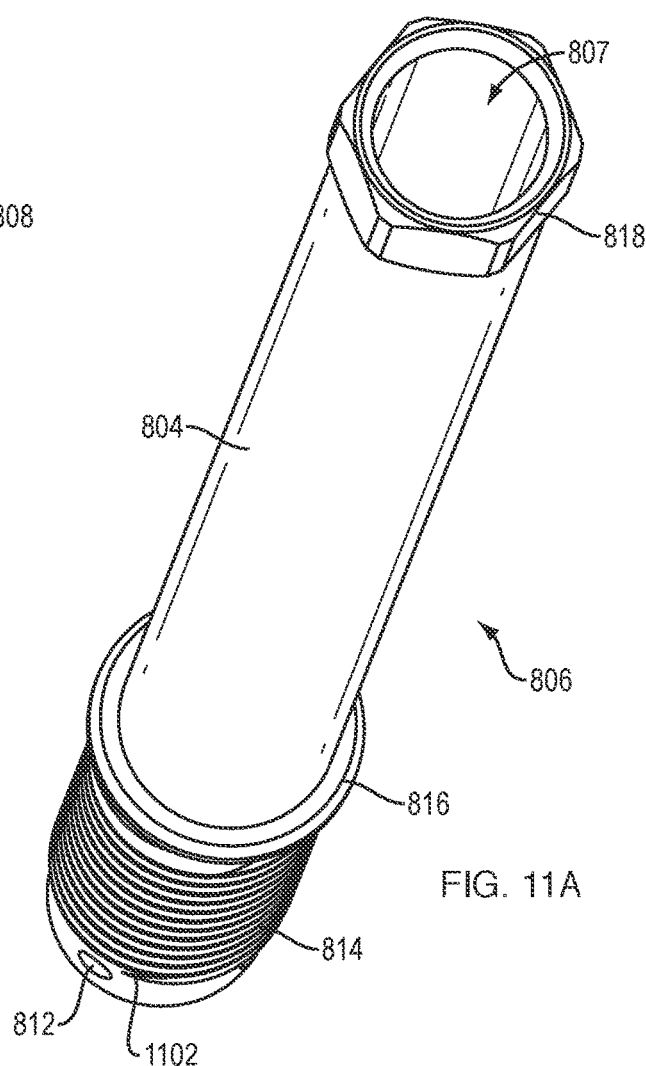
FIG. 11A is a perspective view of the reducer tube of FIG. 8.

An intermediate portion 704 can extend proximally from the depth stop to a drive feature 718 formed on a proximal end of the reducer tube 106. The intermediate portion 704 can have a variety of shapes, diameters, and lengths. In the illustrated embodiment, the intermediate portion 704 has a generally cylindrical shape. The drive feature 718 formed at a proximal end of the reducer tube 106 can allow for modular coupling of a driver handle, powered driver, or other torque application implement to the reducer tube 106 in order to effect rotation of the tube and axial reduction of a spinal fixation element. The drive feature 718 can also permit access to the lumen 707 therethrough, e.g., as shown in FIG. 11A described below. The drive feature 718 can have a variety of forms and sizes. In some embodiments, the drive feature 718 can include one or more flats to facilitate the application of torque thereto. In the illustrated embodiment, the drive feature 718 is a hex feature having six flat portions disposed around a circumference of the reducer tube 106. Further, in the illustrated embodiment an outer diameter of the depth stop 716 can be greater than an outer diameter of any other portion of the reducer tube 106 (e.g., greater than the outer diameter of the threaded portion 714 or the drive feature 718). Utilizing a lower profile drive feature 718 can reduce the footprint of the instrument 100 while still allowing a larger driver handle (e.g., a T-handle, powered driver, etc.) to be coupled to the instrument when needed.

FIGS. 8-12B illustrate another embodiment of a reducer tube 806 and a rod-engaging tip 808 in greater detail. The reducer tube 806 and rod-engaging tip 808 are similar to the embodiments described above, including the use of distal extensions 805 formed on the rod-engaging tip 808, a lumen 807 extending through the two components, and a groove 809 to receive a protrusion formed on the housing 604. The rod-engaging tip 808 includes a differently-shaped opening 810 or window formed in a sidewall thereof. In particular, the opening is extended along a longitudinal axis of the tip 808 but compressed in the radial dimension. The reducer tube 806 includes similar pins 812 or other protrusions (e.g., integrally-formed protrusions, protrusions of different shape, etc.) that can be used to couple the reducer tube to the rod-engaging tip, as well as threads 814, depth stop 816, intermediate portion 804, and drive feature 818.

Figure 9:
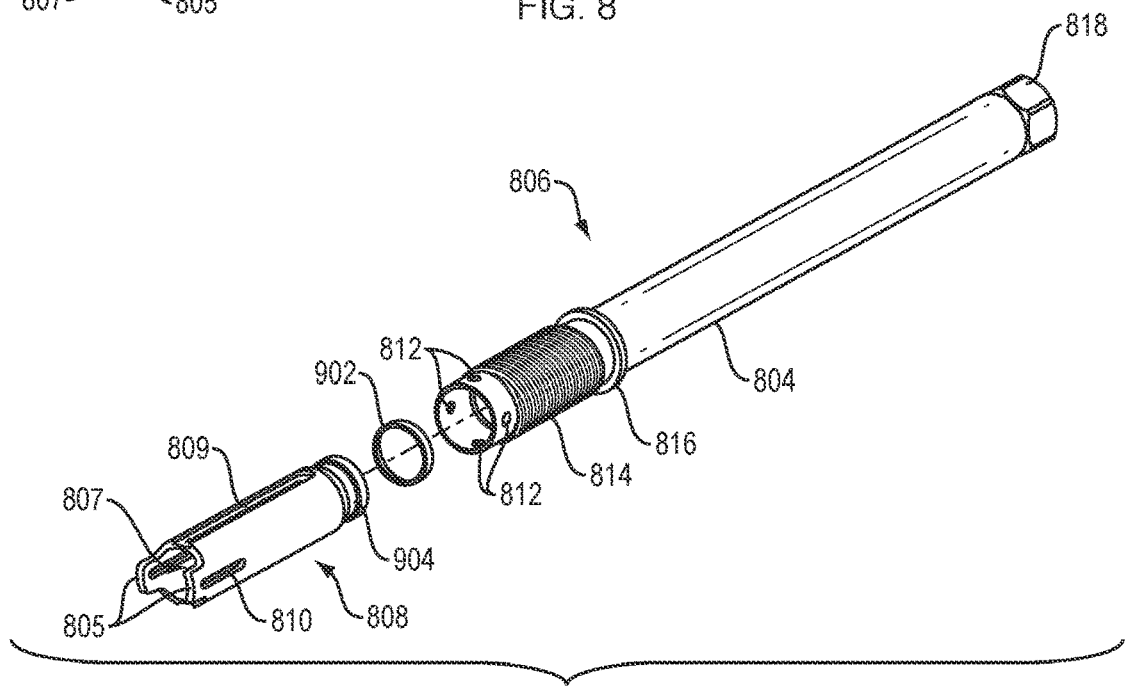
FIG. 9 is an exploded view of the reducer tube and rod-engaging reduction tip of FIG. 8.
Figure 12A:
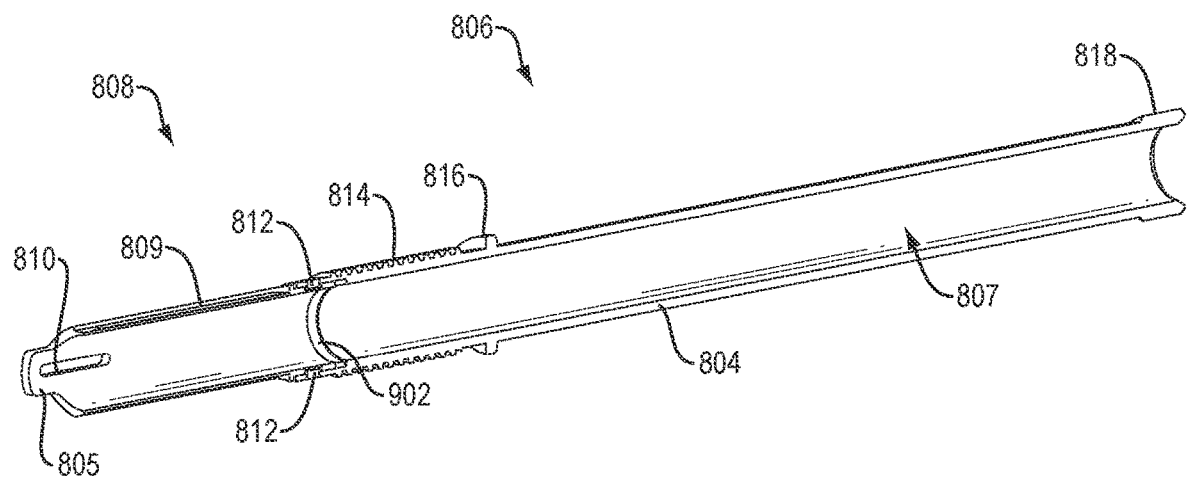
FIG. 12A is a longitudinal cross-sectional view of the reducer tube and rod-engaging reducer tip of FIG. 8.
Figure 12B:
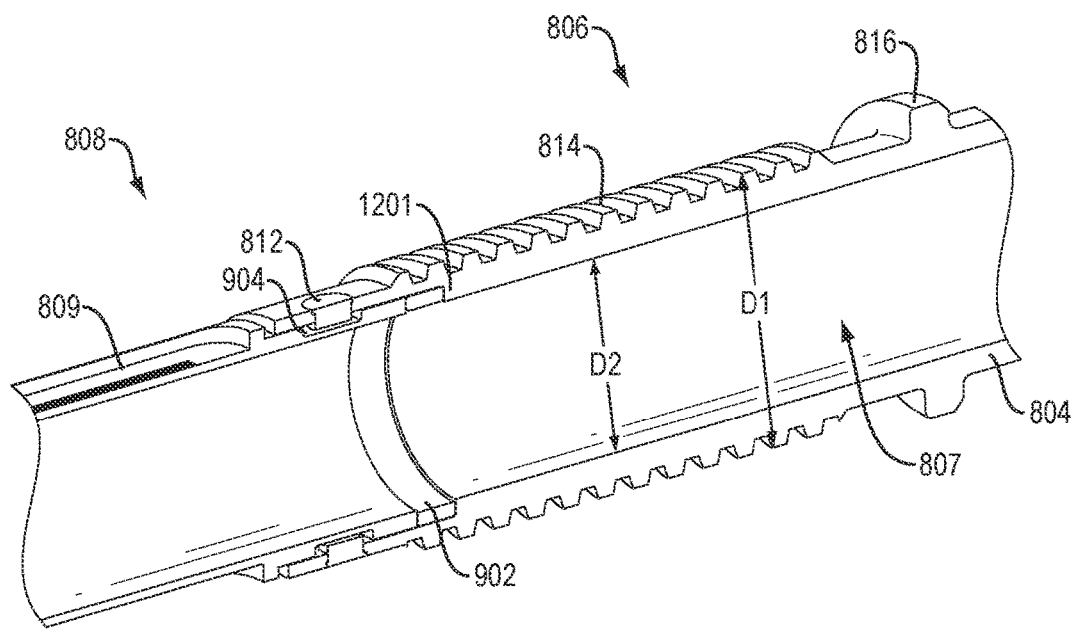
FIG. 12B is a detail view of a distal portion of the reducer tube and a proximal portion of the rod-engaging reducer tip of FIG. 12A.

The exploded view of FIG. 9 and the cross-sectional views of FIGS. 12A and 12B illustrate the rotatable coupling of the reducer tube 806 and rod-engaging tip 808 in greater detail. For example, the pins 812 or other protrusions extending into an interior of the reducer tube 806 are visible, as well as the groove 904 formed in the rod-engaging tip 808 where the pins ride to allow for relative rotation while preventing relative translation. Also shown is a thrust washer 902 disposed between a proximal end of the rod-engaging tip 808 and an interior shoulder 1201 (see FIG. 12B) formed along a distal portion of the reducer tube 806.

Figure 10:
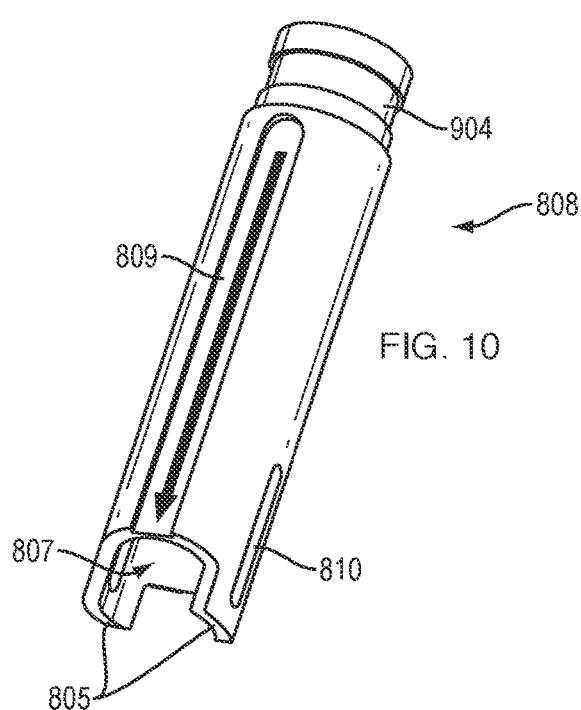
FIG. 10 is a perspective view of the rod-engaging reduction tip of FIG. 8.
Figure 11B:
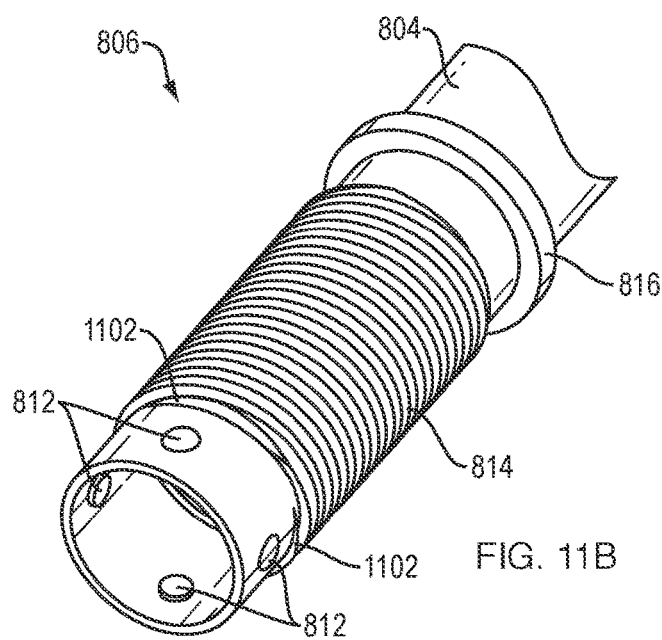
FIG. 11B is a detail view of a distal portion of the reducer tube of FIG. 11A.

FIGS. 10-11B show the rod-engaging tip 808 and reducer tube 806 in isolation to better illustrate their features. Of note in FIG. 11B is the detail view of the threads 814 formed on the outer surface of the reducer tube 806. Any of a variety of thread forms can be utilized with the instruments of the present disclosure. In some embodiments, it can be desirable to utilize a thread form that is low profile in order to minimize an outer diameter of the threaded portion 814, which can allow minimization of a size of the housing 604 and resulting instrument 100. For example and with reference to the detail cross-sectional view of FIG. 12B, in some embodiments an outer diameter D1 of the threaded outer surface portion of the tube can be less than or equal to about 45% larger than a diameter D2 of an inner lumen 807 of the tube 806. In certain embodiments, the outer diameter D1 of the threaded outer surface portion of the tube can be less than or equal to about 40%, about 35%, about 30%, about 25%, or about 20% larger than the diameter D2 of the inner lumen 807 of the tube 806. For example, in one embodiment the diameter D1 can be about 13 mm and the diameter D2 can be about 9 mm. Utilizing such a configuration can minimize an outer diameter of the threads of the tube and provide a lower profile instrument to access a surgical site through a smaller opening or with less interference for adjacent anatomy or instrumentation.

In some embodiments it can also be desirable to provide thread forms with lower mechanical advantage, which can provide better tactile feedback to a user during a reduction maneuver. In some embodiments, thread forms with one or more starts can be utilized and, in some embodiments, a thread forms with a plurality of starts can be utilized. In the illustrated embodiment, a thread form with three starts 1102 (the third start is not visible) is illustrated, as shown in FIG. 11B.

Figure 13:
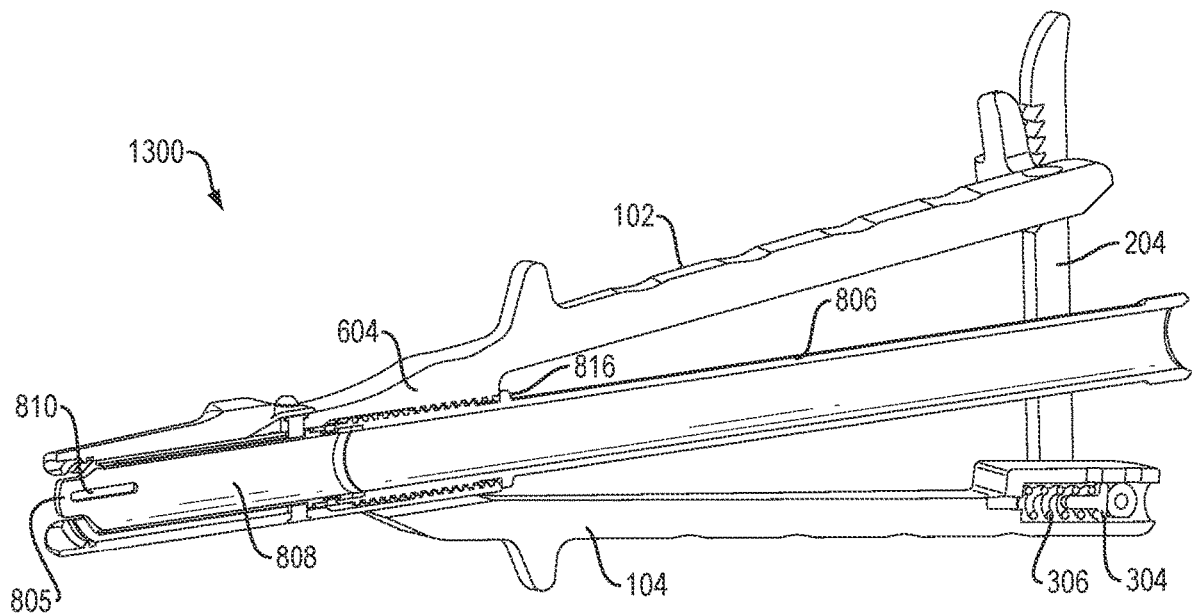
FIG. 13 is a longitudinal cross-sectional view of one embodiment of a biplanar forceps reducer instrument of the present disclosure.
Figure 14:
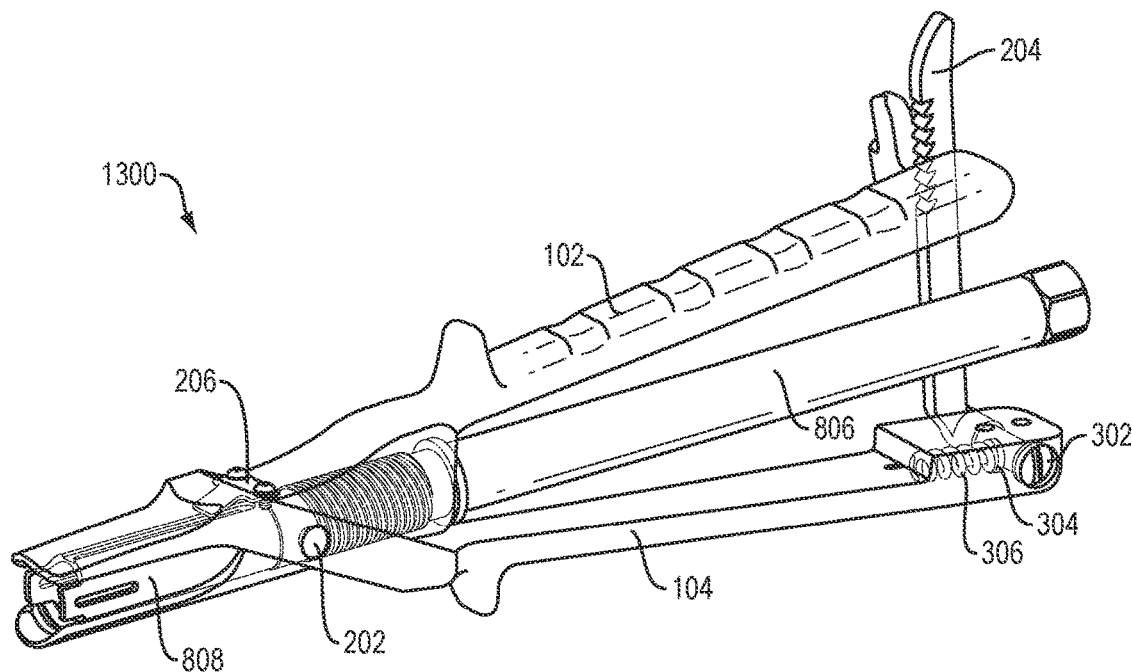
FIG. 14 is a partially-transparent perspective view of the instrument of FIG. 13.

FIGS. 13 and 14 illustrate one embodiment of a biplanar reducer instrument 1300 according to the present disclosure that incorporates the first and second arms 102, 104 discussed above with the reducer tube 806 and rod-engaging tip 808. These figures also illustrate in greater detail the placement and operation of the biasing element 206 that can bias the arms 102, 104 toward an open configuration and the lock 204 with drag force mechanism.

Figure 15:
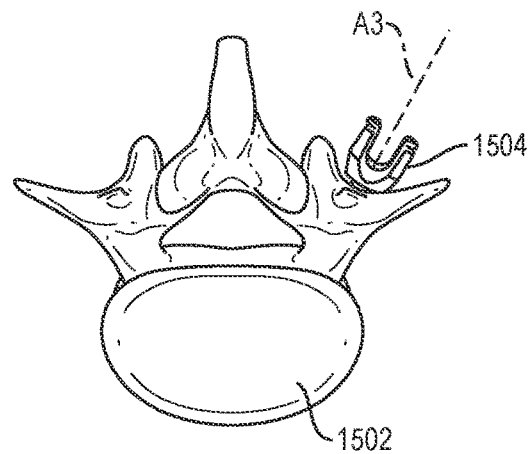
FIG. 15 is a perspective view of one embodiment of a bone screw implanted in a vertebra.
Figure 16:
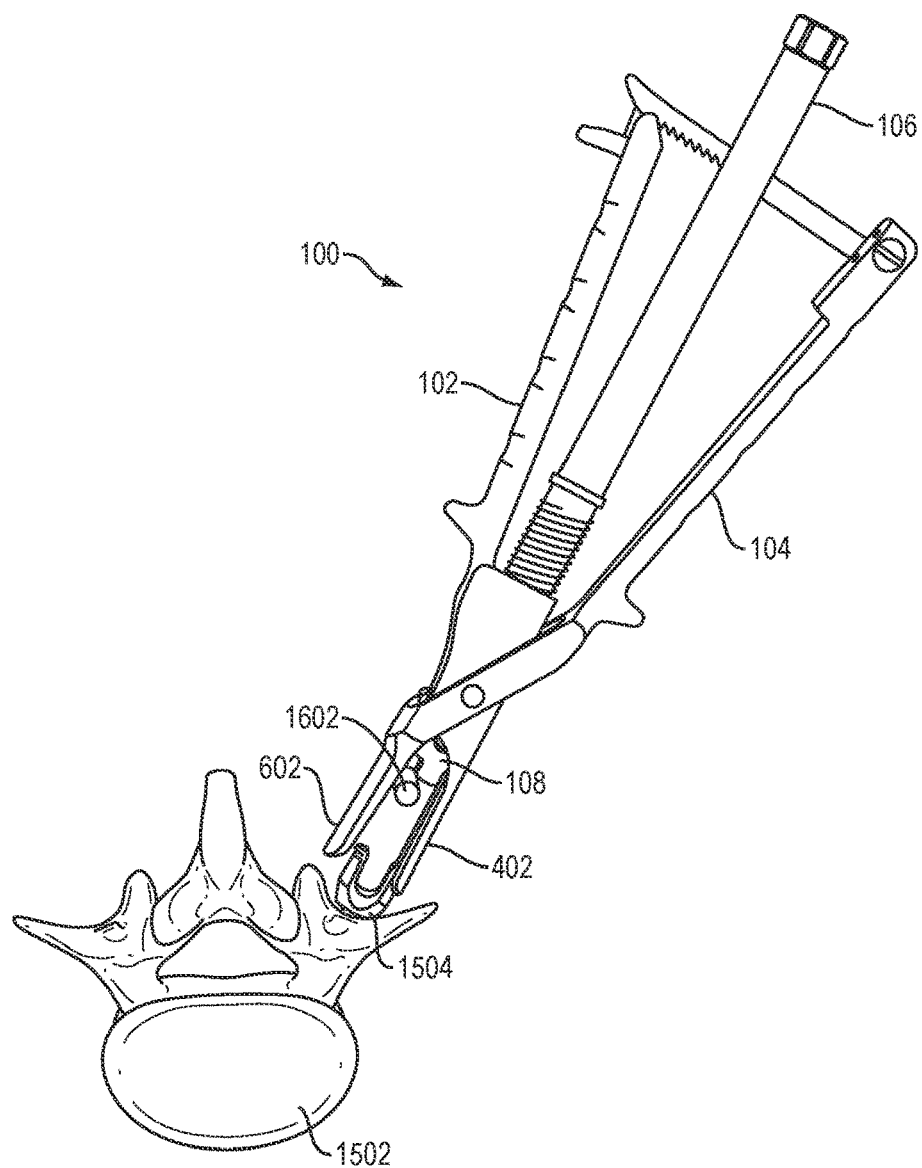
FIG. 16 is a perspective view of the instrument of FIG. 1 capturing a bone screw and spinal fixation rod.

FIGS. 15-26 illustrate a method of operation of a biplanar forceps reducer instrument according to the present disclosure. FIG. 15 illustrates one embodiment of a vertebral body 1502 and a bone anchor or implant 1504 (also shown is a longitudinal axis A3 of the implanted bone anchor). FIG. 16 shows the vertebral body 1502 and implant 1504 with a spinal fixation element 1602, e.g., a rod, disposed in a position that is both laterally (e.g., transverse to the longitudinal axis A3 of the implanted bone anchor) and axially (e.g., parallel to the longitudinal axis A3 of the implanted bone anchor) offset relative to the bone anchor. FIG. 16 also shows the introduction of the biplanar forceps reducer instrument 100, in particular a first positioning of the instrument in which a distal portion 402 of the first arm 102 is docked against one side of the bone anchor 1504 and the distal portion 602 of the second arm 104 is used to capture the laterally offset rod 1602.

Figure 17:
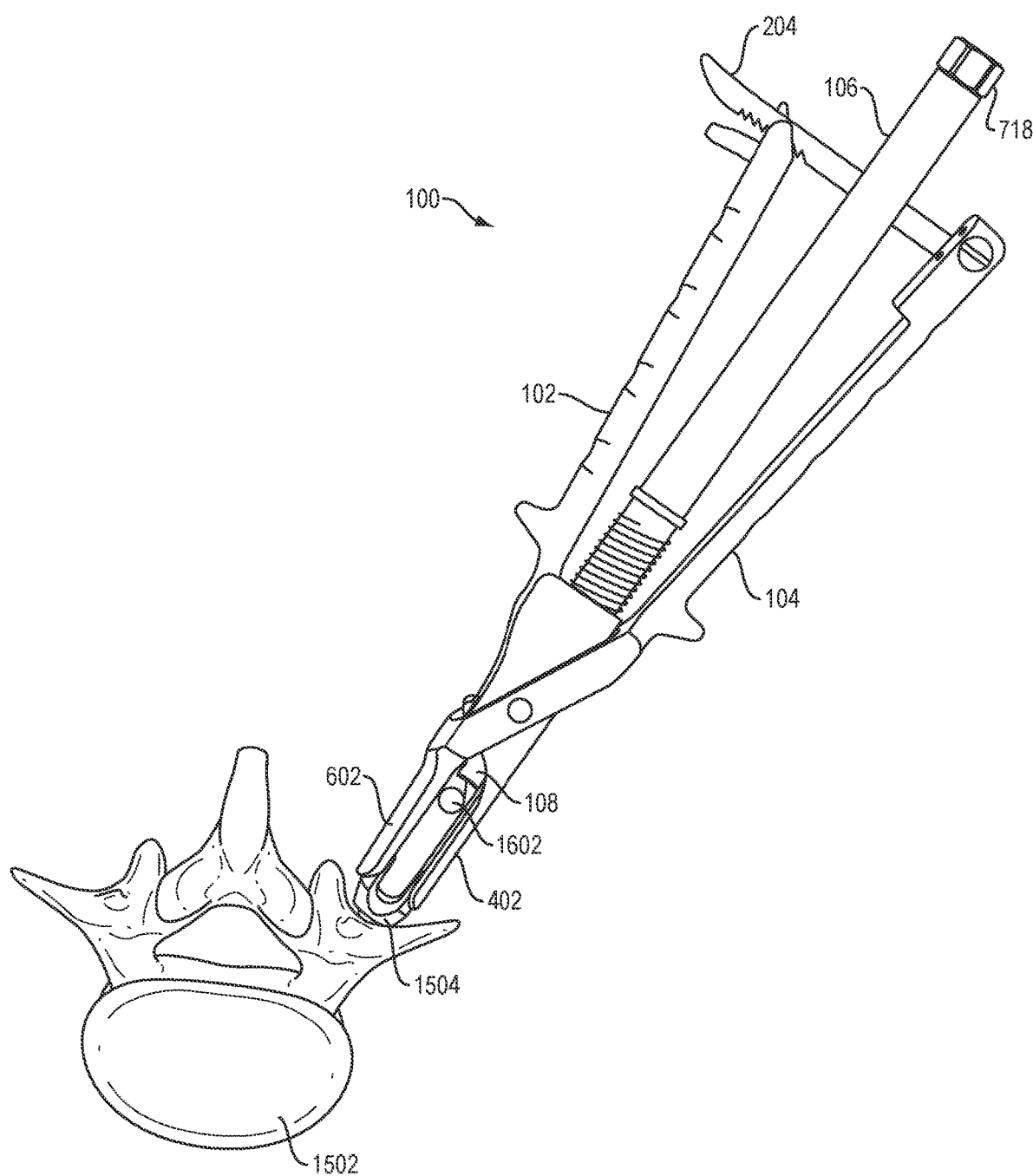
FIG. 17 is a perspective view of the instrument of FIG. 1 laterally reducing a spinal fixation rod.

FIG. 17 illustrates a lateral reduction step that can be achieved by actuating the first and second arms 102, 104. In particular, a user can bring proximal handle portions of the arms 102, 104 toward one another to cause the distal portions 402, 602 to pivot toward one another. This movement will urge the rod 1602 and the implant 1504 toward one another in a lateral direction (e.g., a direction transverse to the longitudinal axis of the instrument or the implant), ultimately bringing the rod into lateral alignment with the implant along a longitudinal axis, as shown in FIG. 17. Actuation of the arms 102, 104 can also result in the distal portions 402, 602 of both arms being docked to the implant 1504 (e.g., such that engagement features formed thereon interface with complementary features formed on opposed outer surfaces of the implant). Still further, FIG. 17 shows the lock 204 maintaining a relative position of the first and second arms 102, 104 such that a user need not maintain force applied to the arms to pivot them toward one another.

Figure 18:
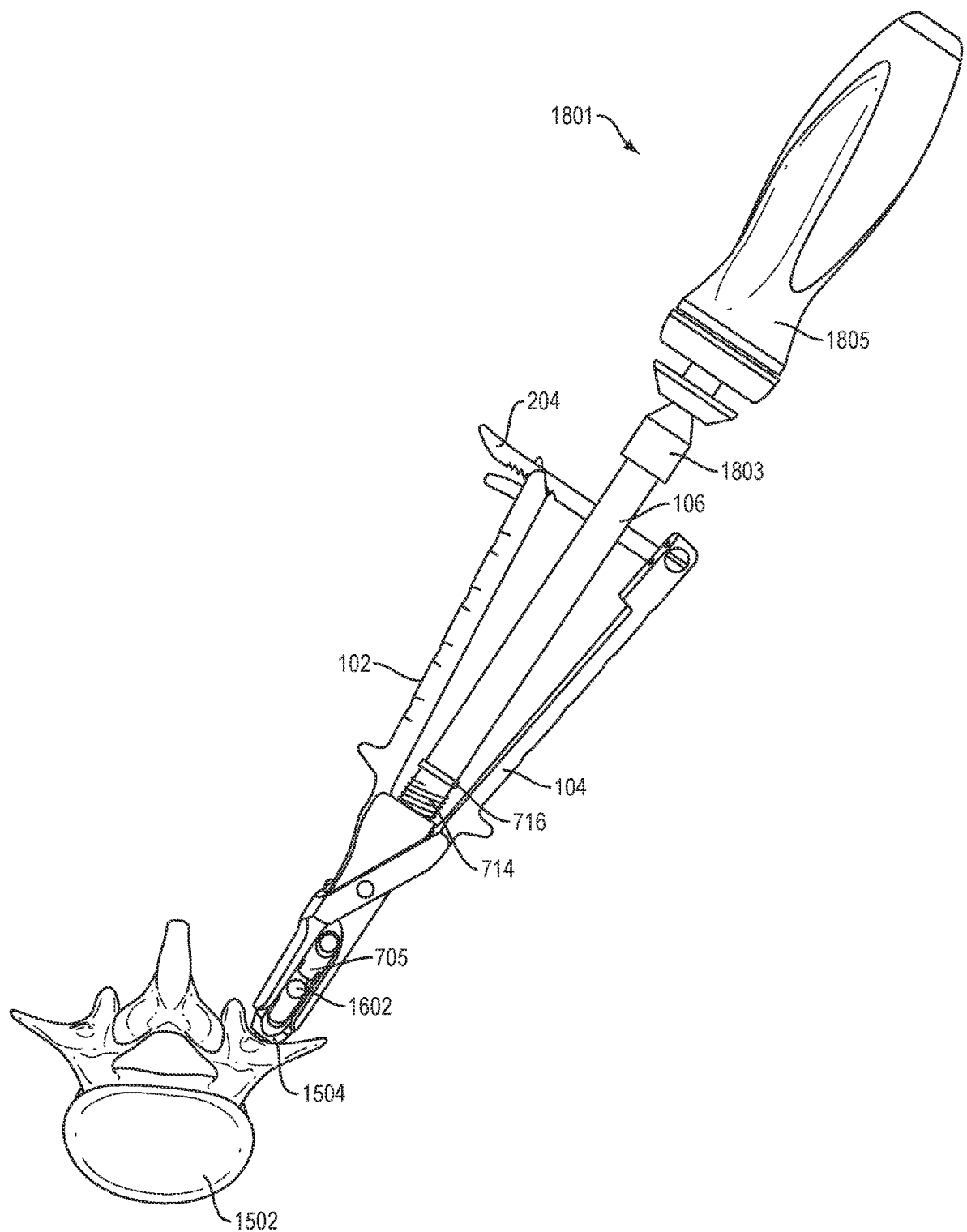
FIG. 18 is a perspective view of the instrument of FIG. 1 axially reducing a spinal fixation rod using a driver.

FIG. 18 illustrates the introduction of a modular driver 1801 that can be coupled to a proximal drive feature 718 of the reducer tube 106 to effect rotation thereof. The driver 1801 can include a coupling feature 1803 at a distal end thereof and a proximal handle 1805. The coupling feature can be configured to interface with the drive feature 718 in a manner that permits application of torque to the reducer tube 106. In the illustrated embodiment, the coupling feature can be a hex socket 1803 configured to receive the hex drive feature 718 formed on the reducer tube 106. As noted above, an of a variety of alternative drive and coupling feature geometries can be utilized. Further, while a hand-actuated driver 1801 is illustrated, in other embodiments a differently-configured hand-powered (e.g., a T-handle, etc.) or powered (e.g., electric, pneumatic, hydraulic, etc.) actuator can be utilized.

Once the driver 1801 is assembled to the reducer tube 106, a user can rotate the reducer tube to effect axial translation or reduction of the rod 1602 toward the implant 1504. In particular, and as described above, rotation of the reducer tube 106 can cause distal advancement thereof relative to the arms 102, 104 and implant coupled thereto due to the threaded coupling between the reducer tube and the housing 604 of the first arm 102. Distal advancement of the reducer tube 106 can cause distal advancement of the rod-engaging tip 108 since these components are coupled in a manner that allows for relative rotation but prevents relative translation. The rod-engaging tip 108 can be prevented from rotating relative to the arms 102, 104 by the protrusion formed on the housing 604 of the first arm 104 riding within the longitudinal groove 709 of the rod-engaging tip. As the rod-engaging tip 108 advances distally, the distal-most extensions 705 formed thereon can contact the rod 1602 and urge it distally toward the implant 1504. Lateral movement of the rod 1602 can be prevented by the distal portions 402, 602 of the arms 102, 104.

Figure 19:
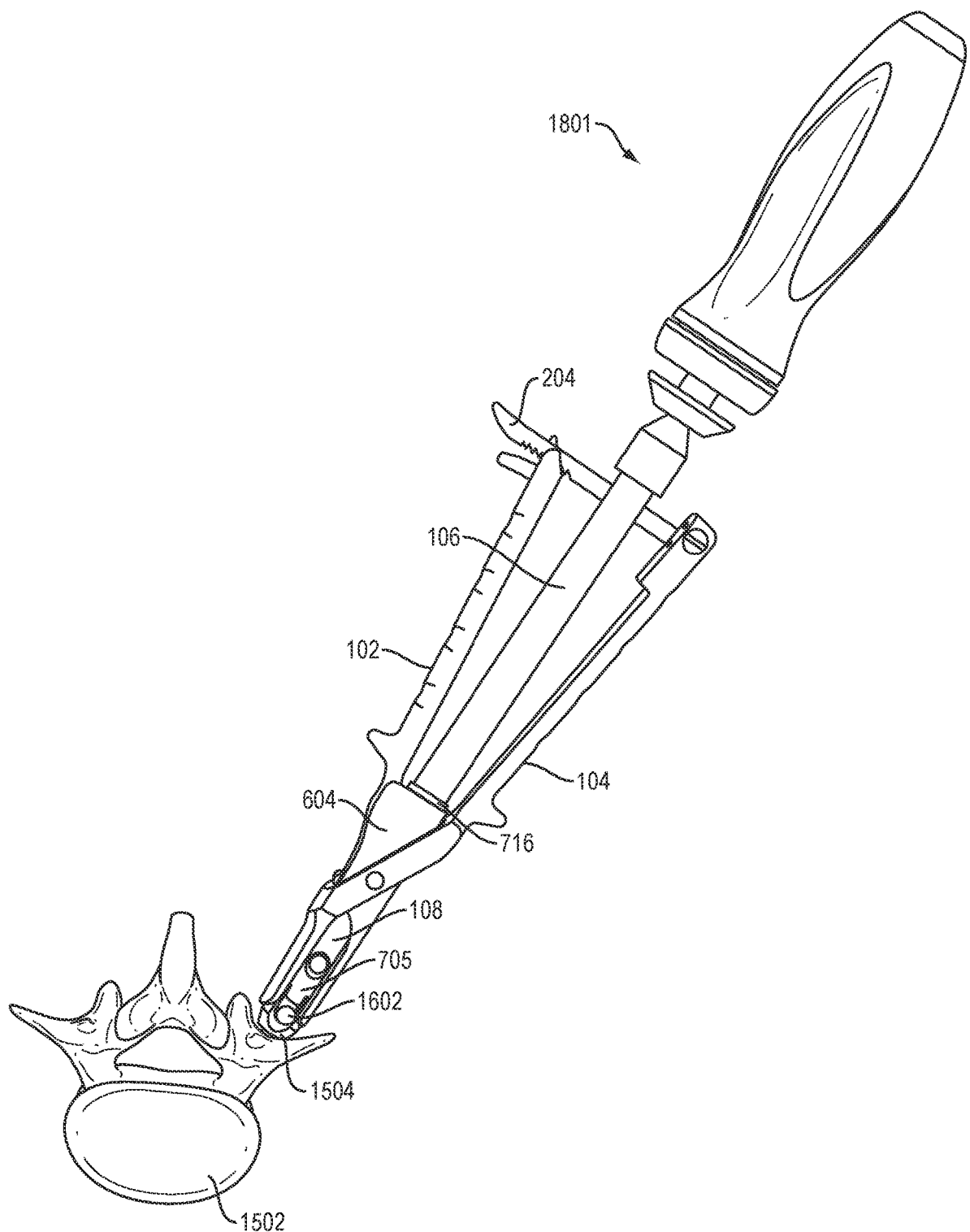
FIG. 19 is a perspective view of the instrument of FIG. 1 after axially reducing a spinal fixation rod.
Figure 20:
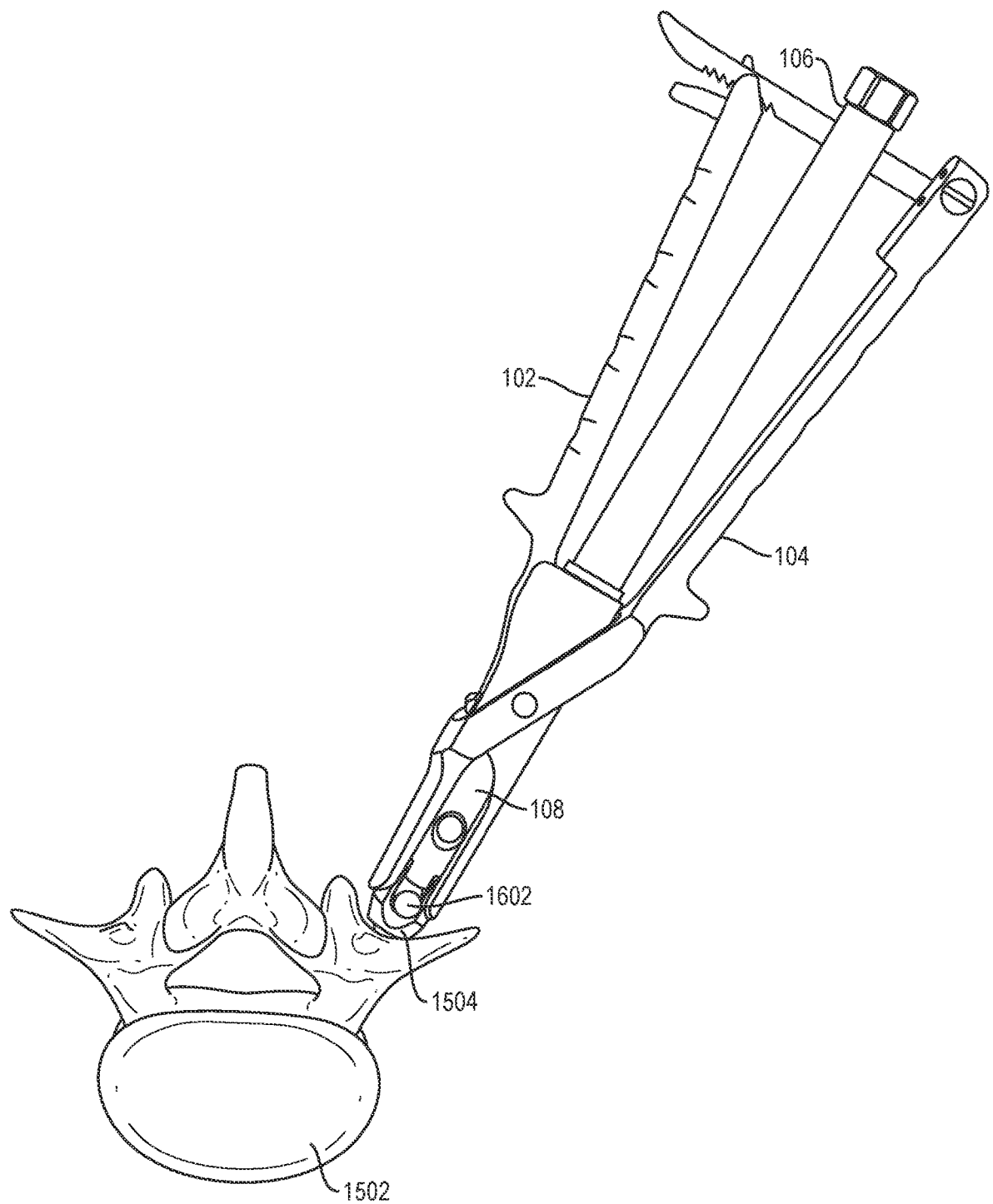
FIG. 20 is a perspective view of the instrument of FIG. 1 after removal of a driver.

FIG. 19 illustrates a fully reduced position of the rod 1602 within a seat of a receiver member of the implant 1504 when the reducer tube 106 has been advanced to a point where the depth stop 716 contacts a proximal end of the housing 604 of the first arm 102. Following reduction, the driver 1801 can be removed from the instrument 100, as shown in FIG. 20.

Figure 21:
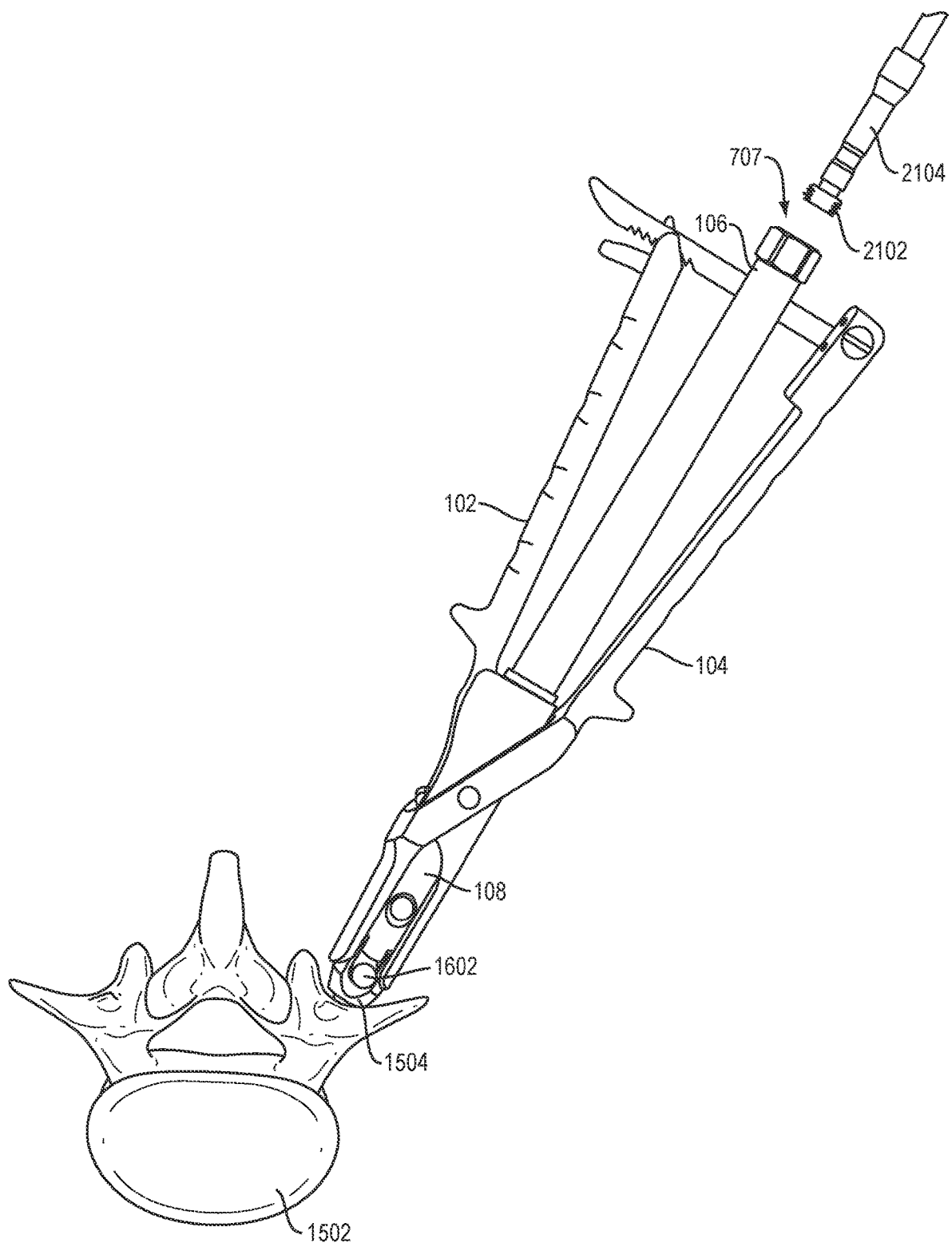
FIG. 21 is a perspective view of a set screw being inserted through the instrument of FIG. 1.
Figure 22:
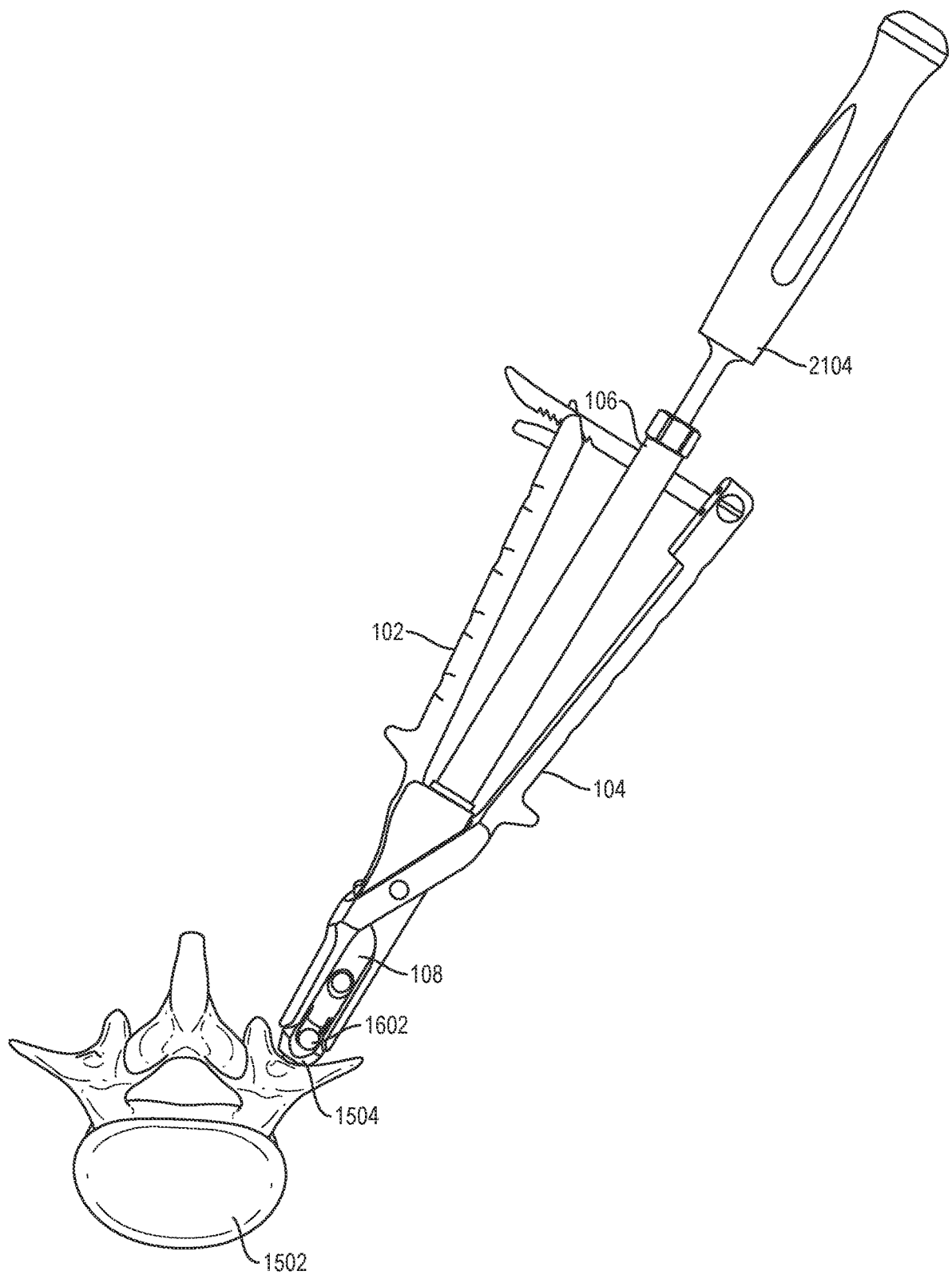
FIG. 22 is another perspective view of a set screw being inserted through the instrument of FIG. 1.

With the modular driver 1801 separated from the reducer tube 106, a set screw 2102 or other locking element can be advanced toward the implant 1504 through the inner lumen 707 of the reducer tube 106. In particular, the set screw 2102 can be coupled to a distal end of an inserter 2104 and the inserter can be utilized to advance the set screw into the lumen 707 from the proximal end of the reducer tube 106, as shown in FIG. 21. Once the set screw 2102 reaches the implant 1504, the inserter 2104 can be utilized to engage the set screw with threads formed on a proximal portion of the implant receiver member, as shown in FIG. 22. As noted above, the depth stop 716 and configuration of the instrument 100 can be such that it does not achieve a true final position of the rod 1602 (i.e., where the rod is bottomed out against a distal portion of a rod seat of the receiver member), but instead reduces the rod far enough to allow a set screw to engage threads in the receiver member. This can allow final reduction and tightening of the rod to be performed using the set screw 2102 and inserter 2104. This will also allow for easier separation of the instrument 100 by reducing tension in the coupling with the implant 1504 and rod 1602.

Figure 23A:
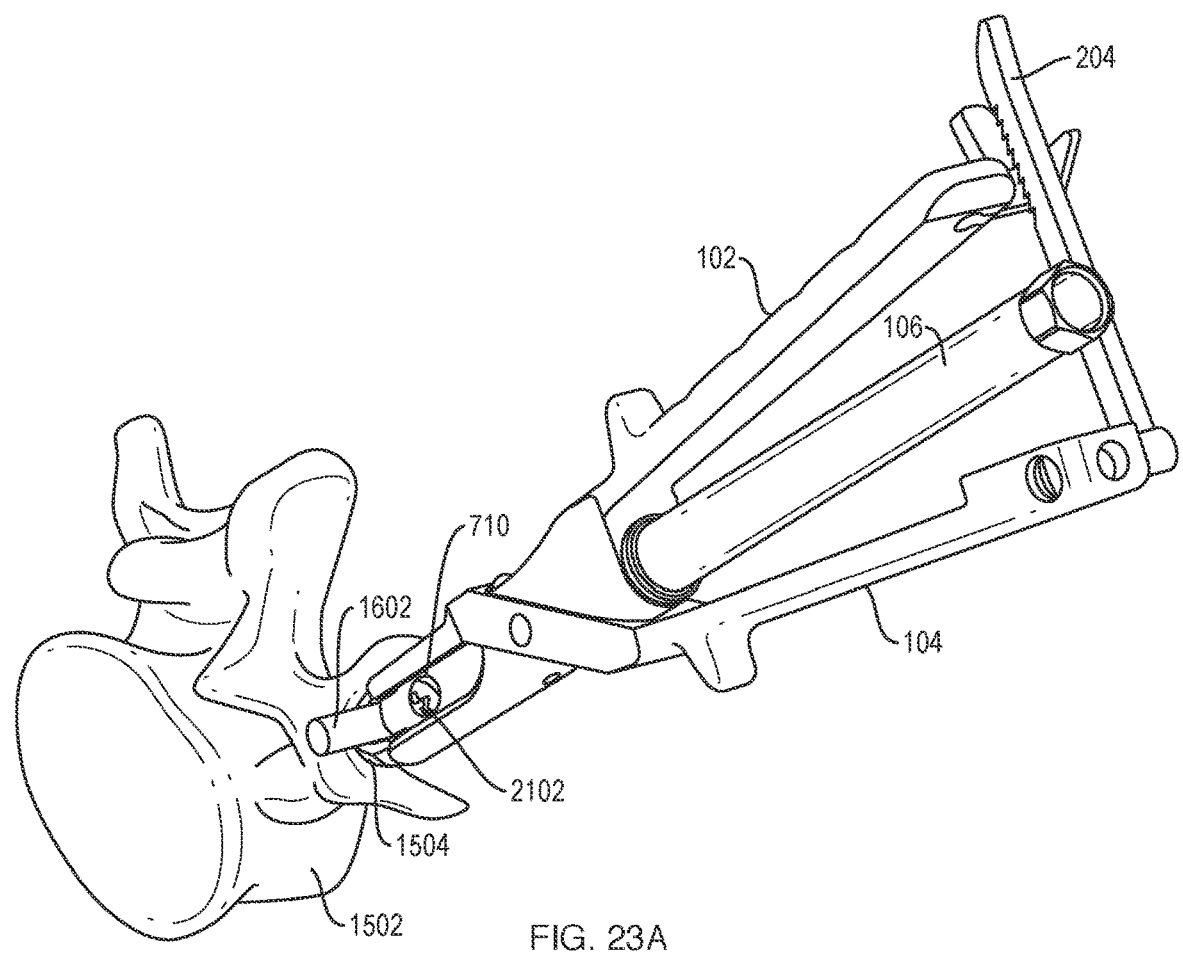
FIG. 23A is a perspective view of the instrument of FIG. 1 after insertion of a set screw.
Figure 23B:
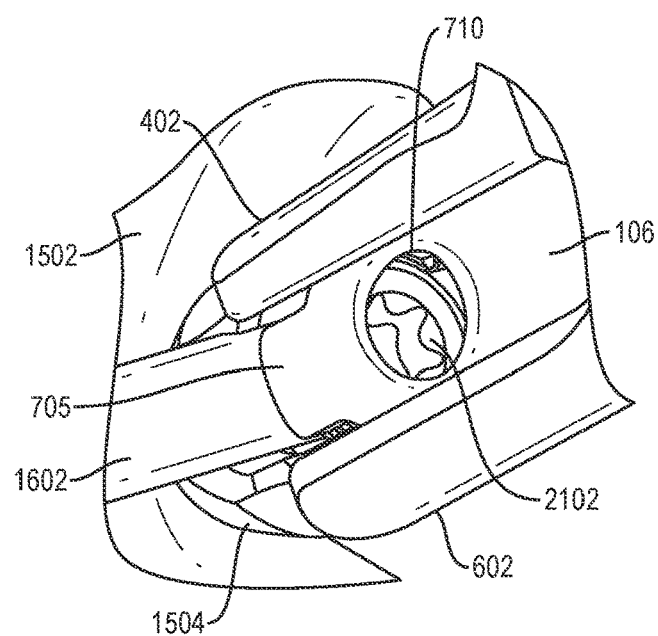
FIG. 23B is a detail view of a distal portion of FIG. 23A.

Once the inserter 2104 is utilized to tighten the set screw 2102 to a desired degree, the inserter 2104 can be removed proximally and withdrawn from the inner lumen 707 of the reducer tube 106 and rod-engaging tip 108. Placement of the set screw 2102 can be verified visually through the opening 710 formed in the sidewall of the rod-engaging tip 108, as shown in FIGS. 23A and 23B.

Figure 24:
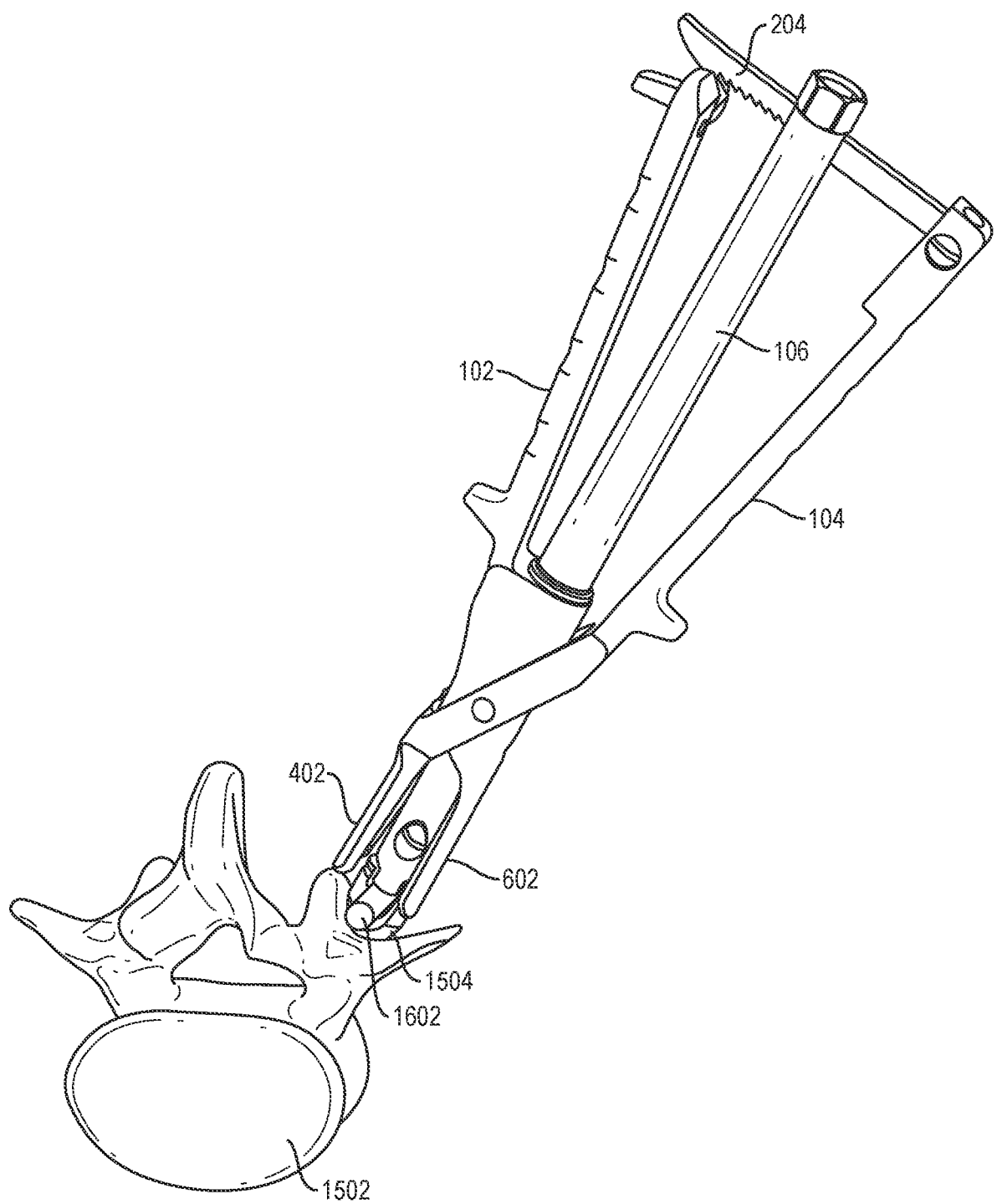
FIG. 24 is a perspective view of the instrument of FIG. 1 releasing from a bone screw.
Figure 25:
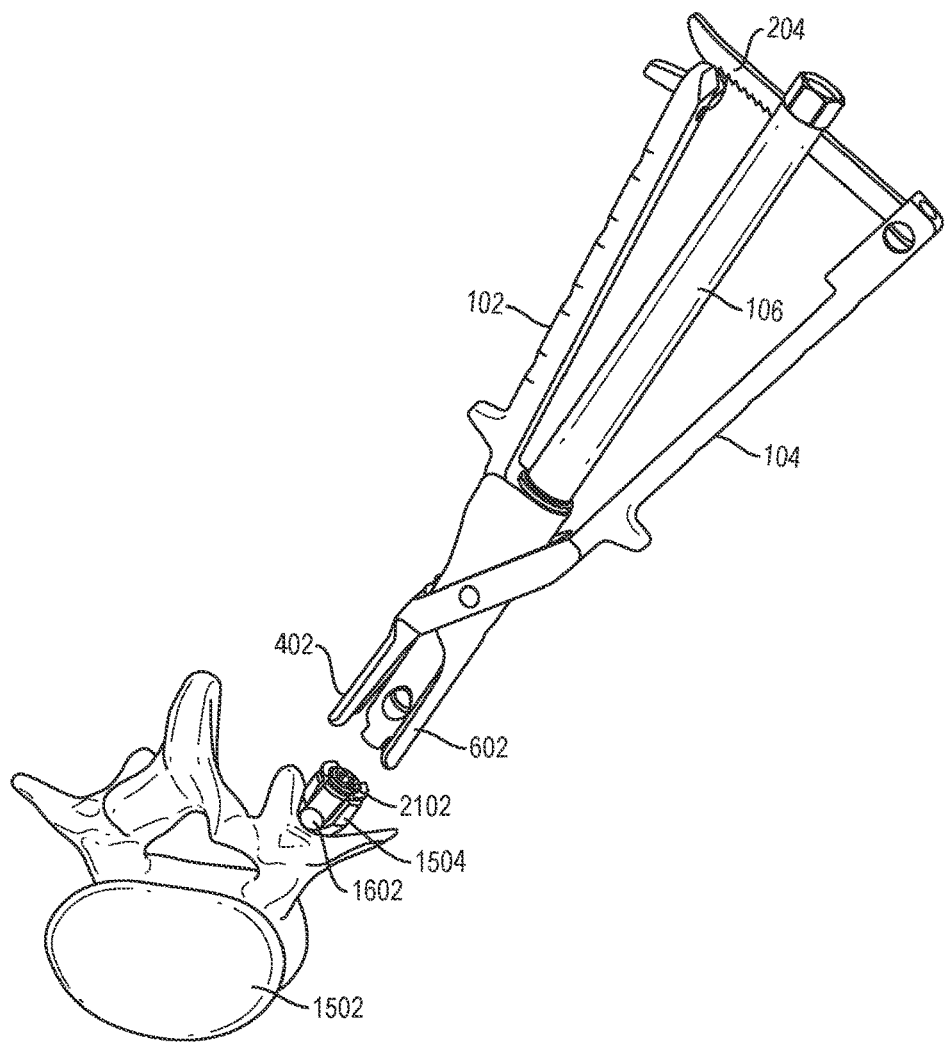
FIG. 25 is a perspective view of the instrument of FIG. 1 withdrawing from a bone screw.
Figure 26:
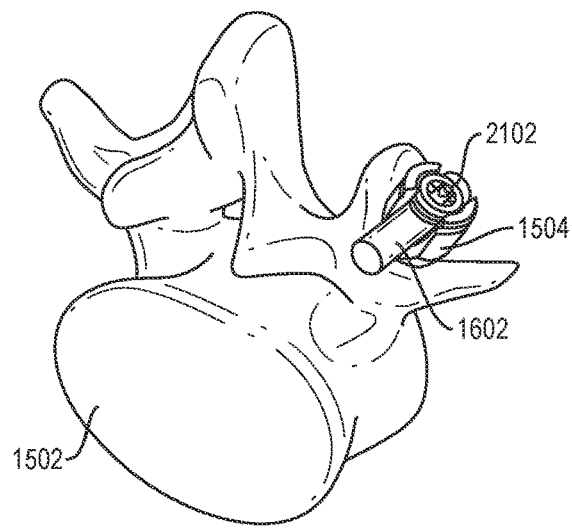
FIG. 26 is a perspective view of a bone screw and spinal fixation rod fastened to a vertebra.

FIG. 24 illustrates a next method step in which the instrument 100 is separated from the implant 1504. This can be accomplished by releasing the lock 204 (e.g., pivoting the ratchet bar 410 out of engagement with the catch 610) and allowing the first and second arms 102, 104 to pivot away from one another to separate the distal portions 402, 602 thereof from the implant 1504. The instrument 100 can then be withdrawn proximally, as shown in FIG. 25. This leaves the final implanted bone anchor 1504 with fully reduced rod 1602 secured by set screw 2102, as shown in FIG. 26.

Figure 27A:
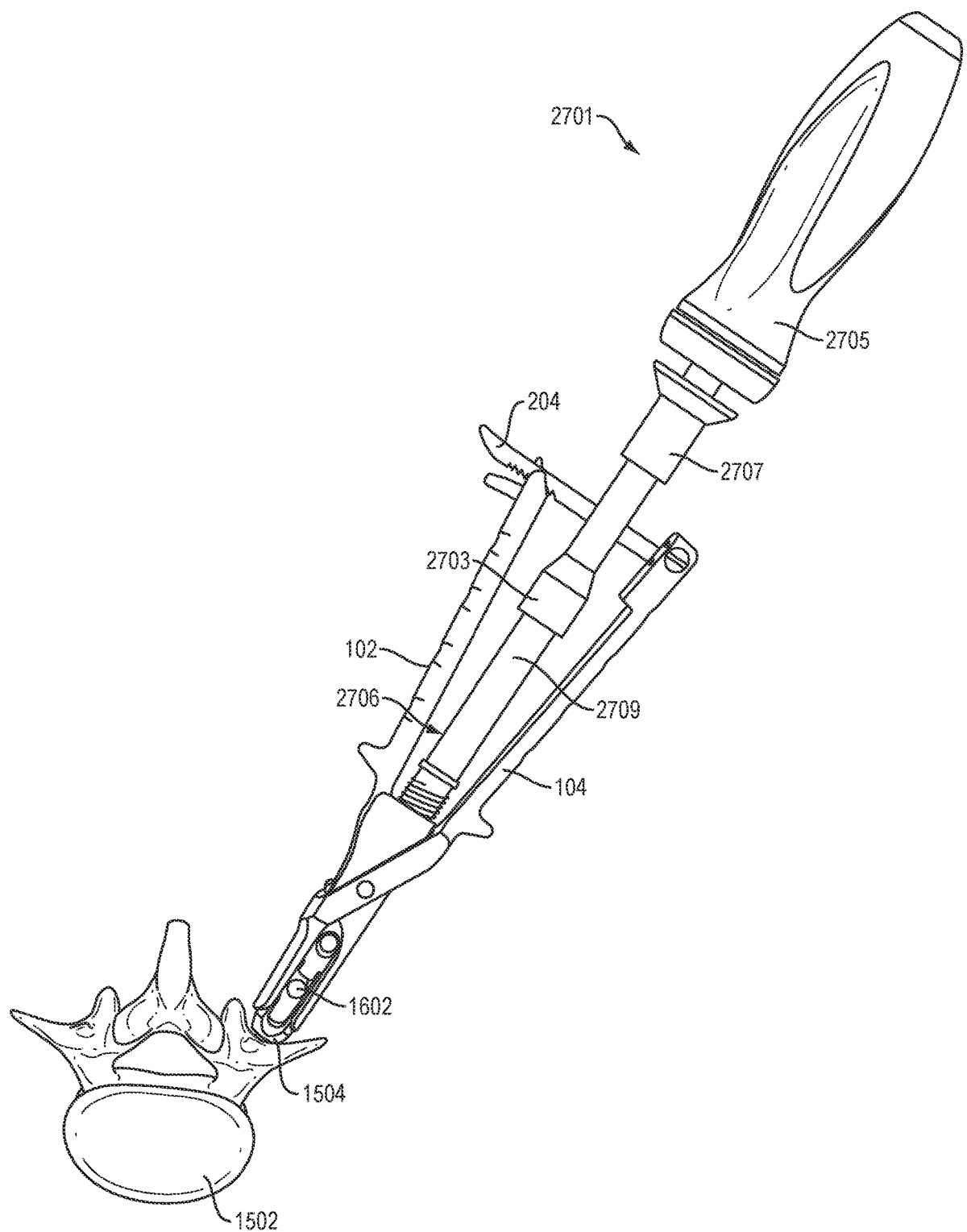
FIG. 27A is a perspective view of one embodiment of a biplanar forceps reducer and driver according to the present disclosure.
Figure 27B:
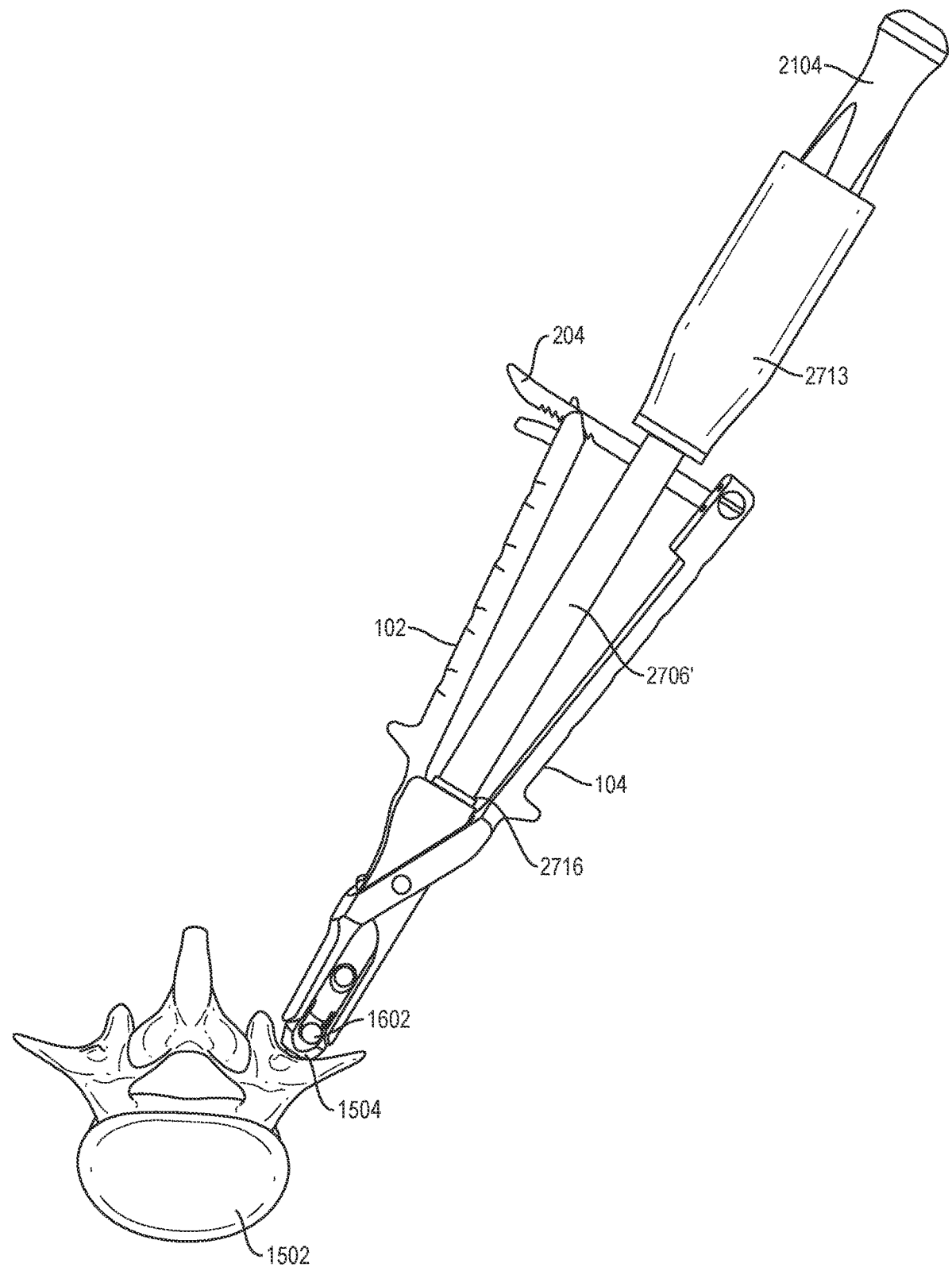
FIG. 27B is a perspective view of one embodiment of a biplanar forceps reducer with integrated driver according to the present disclosure.
Figure 28:
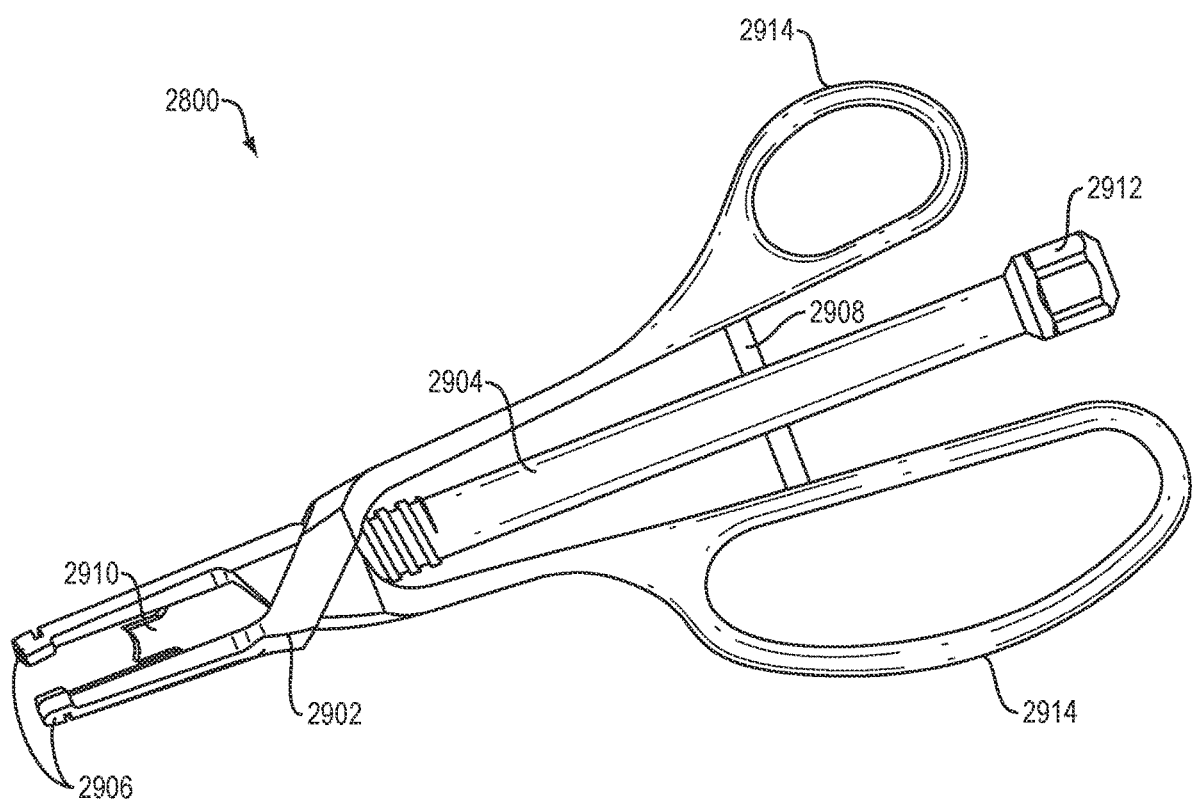
FIG. 28 is a perspective view of one embodiment of a biplanar forceps reducer according to the present disclosure.

FIGS. 27A and 27B illustrate alternative embodiments of biplanar forceps reducer instruments. FIG. 27A, for example, illustrates an embodiment in which a reducer tube 2706 having a shorter intermediate portion 2709 is utilized. In particular, the reducer tube 2706 can include an intermediate portion 2709 that is short enough in length that the proximal end drive feature of the reducer tube is disposed distal to the lock 204 and/or proximal ends of the arms 102, 104. In order to avoid interference with the proximal portions of the arms 102, 104 and lock 204 during operation, a driver 2701 can be utilized that includes an extended intermediate portion 2707 between its coupling feature 2703 and proximal handle 2705.

FIG. 27B illustrates another embodiment in which a reducer tube 2706' includes an integrated driver handle 2713 rather than the modular configuration described above. In such an embodiment, the reducer tube driver handle 2713 can still provide access to an inner lumen thereof through its proximal end, such that a set screw inserter 2104 can be utilized to deliver a set screw, as shown in FIG. 27B.

Figure 29:
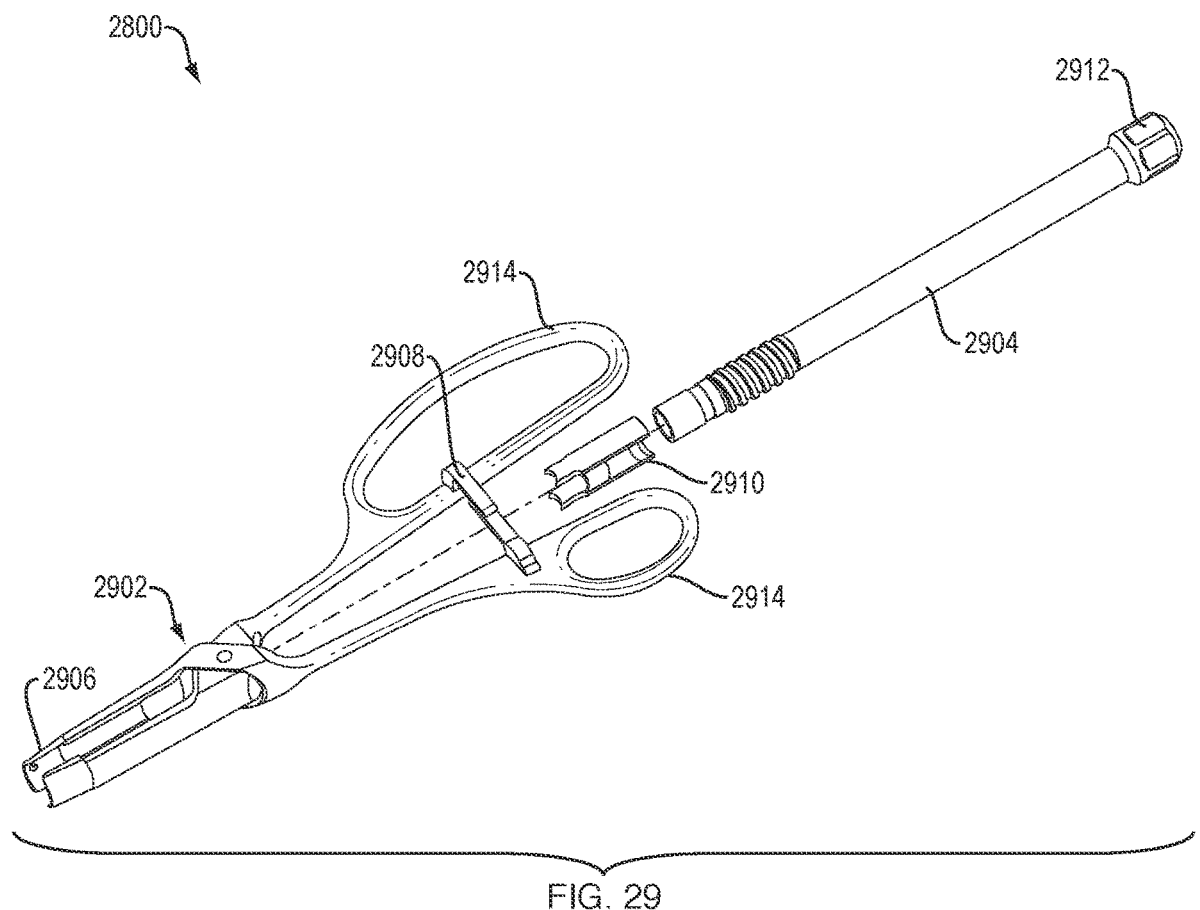
FIG. 29 is an exploded view of the instrument of FIG. 28.

Still other alternative embodiments are also contemplated and provided in the present disclosure. For example, FIGS. 28-35 illustrate views of one embodiment of a biplanar forceps reducer 2800 according to the present disclosure. The exploded view of FIG. 29 shows that the instrument 2800 includes lateral reduction forceps 2902 with internal reduction threads that interface with a hollow axial reducer tube 2904 having external reduction threads formed thereon. Opposed distal tips 2906 of the forceps 2902 include implant engagement features that can interface with portions of a bone anchor receiver head, such as opposed sides or features formed on opposed sides, e.g., notches, grooves, holes, etc. The forceps 2902 can include a ratchet lock 2908 that is offset from the longitudinal axis of the reducer tube to ensure no interference between these components. A rod-engaging reduction tip 2910 can be coupled to a distal end of the reducer tube 2904 in a manner that allows relative rotation of the tip about a longitudinal axis of the tube but prevents axial translation or separation of the components. The rod-engaging tip 2910 can be disposed between the opposed lateral reduction forceps 2902 and prevented from rotating relative thereto such that the tip remains properly oriented to engage a rod even as the axial reducer tube is rotated. Finally, a driver feature 2912 or handle can be formed on a proximal end of the axial reducer tube 2904 to facilitate rotation of the tube to effect axial reduction of a rod disposed between the opposed jaws of the lateral reduction forceps 2902.

Figure 30:
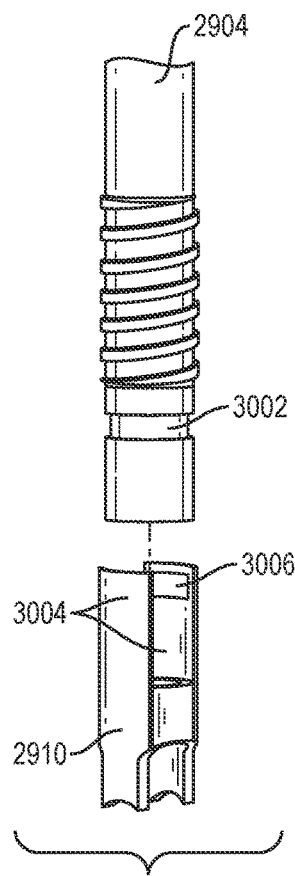
FIG. 30 is an exploded view of a rod-engaging reducer tip and a distal portion of a reducer tube of the instrument of FIG. 28.

FIG. 30 illustrates the distal end of the axial reducer tube 2904 and the rod-engaging tip 2910. The axial reducer tube 2904 and rod-engaging tip 2910 can be hollow to allow for set screw passage while minimizing tube outer diameter. This can contribute to lower instrument profile and improve the ability to use the instrument in tight spaces, e.g., on adjacent closely spaced vertebral levels, etc. The distal end of the reducer tube 2904 can include a groove 3002 and the proximal end of the rod-engaging tip 2910 can include opposed wings 3004 with a feature 3006 that snaps into the groove 3002 of the reducer tube to allow free rotation about a longitudinal axis of the tube while preventing axial translation or separation thereof.

Figure 31:
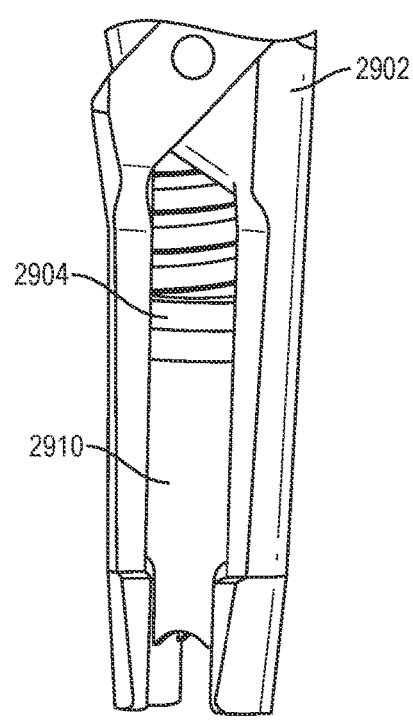
FIG. 31 is a detail side view of a distal portion of the instrument of FIG. 28.
Figure 32:
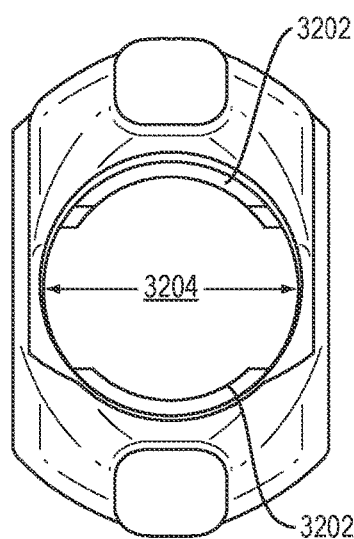
FIG. 32 is detail end view of a forceps body of the instrument of FIG. 28.

As shown in FIGS. 31 and 32, the body of the forceps 2902 can include internal threads 3202 to interface with the external threads of the reducer tube. The threads 3202 can include bilateral slots 3204 formed therein to allow the rod-engaging tip 2910 to pass through. Further, the opposed wings or arms 004 of the rod-engaging tip can articulate with the distal portion of the lateral reducer forceps jaws to prevent rotation of the rod-engaging tip 2910 as the axial reducer tube is rotated through the threads formed on the forceps body 2902.

Figure 33:
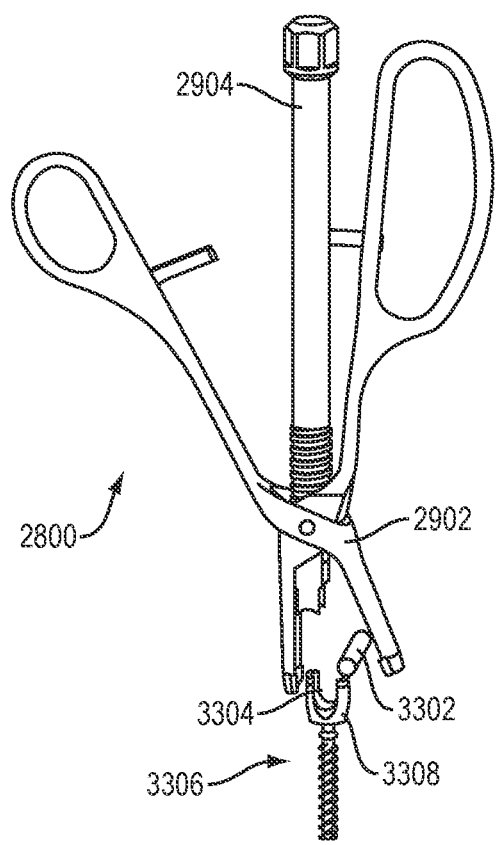
FIG. 33 is a perspective view of the instrument of FIG. 28 approaching a bone screw and spinal fixation rod.
Figure 34:
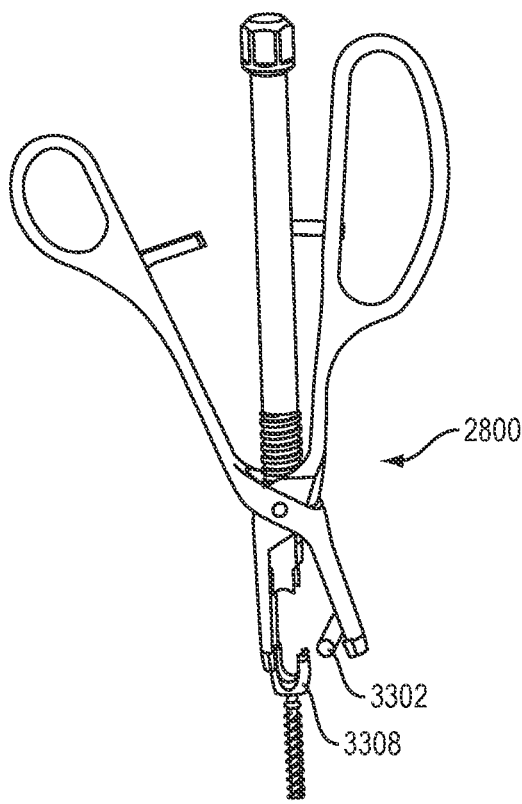
FIG. 34 is a perspective view of the instrument of FIG. 28 capturing a bone screw and spinal fixation rod.
Figure 35:
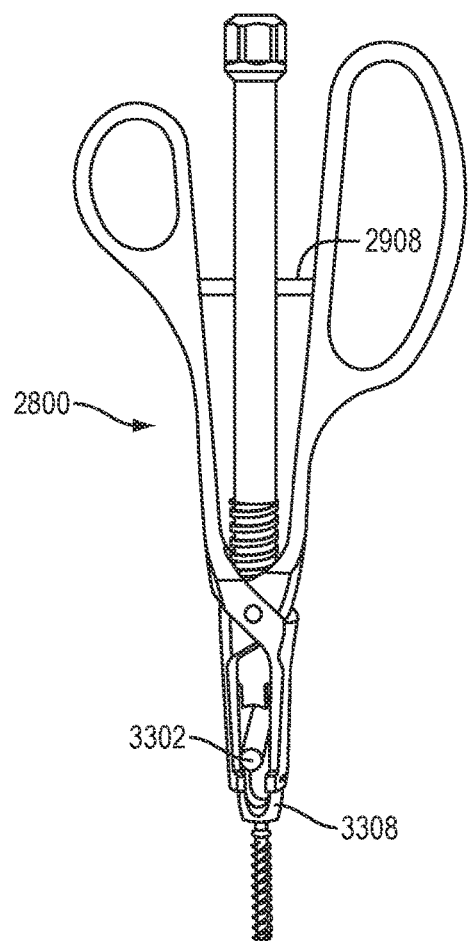
FIG. 35 is a perspective view of the instrument of FIG. 28 laterally reducing a spinal fixation rod.

FIGS. 33-38 illustrate a method of using the instrument 2800 described above. In FIG. 33, the illustrated rod 3302 is positioned both laterally and axially offset from the channel 3304 of the bone anchor 3306 receiver head 3308. The reducer forceps 2902 are moved to an open position and the reducer tube 2904 is rotated to withdraw it proximally. The reducer is positioned to capture both the rod 3302 and receiver head 3308 between distal forceps arms or jaws. In FIG. 34, the reducer instrument 2800 engages the rod 3302 and receiver head 3308 by positioning a first forceps jaw or arm against the bone anchor receiver head and a second forceps jaw or arm against the rod that is laterally and axially offset from the receiver head. FIG. 35 shows the lateral rod translation or reduction accomplished by bringing the forceps handles toward one another and causing the distal forceps jaws or arms to move toward one another. The ratchet lock 2908 of the forceps can maintain the lateral reduction and allow for step-wise, incremental reduction engaging sequential teeth of the ratchet lock. Further, closing the forceps jaws or arms toward one another can lock the forceps to the bone anchor receiver head 3308 by bringing the second forceps jaw or arm into contact with the receiver head. As noted above, the receiver head 3308 can include one or more features (e.g., notches, grooves, indentations, protrusions, etc.) that can interface with complementary features formed on inner surfaces of the distal forceps jaws or arms to facilitate more secure locking of the forceps to the receiver head.

Figure 36:
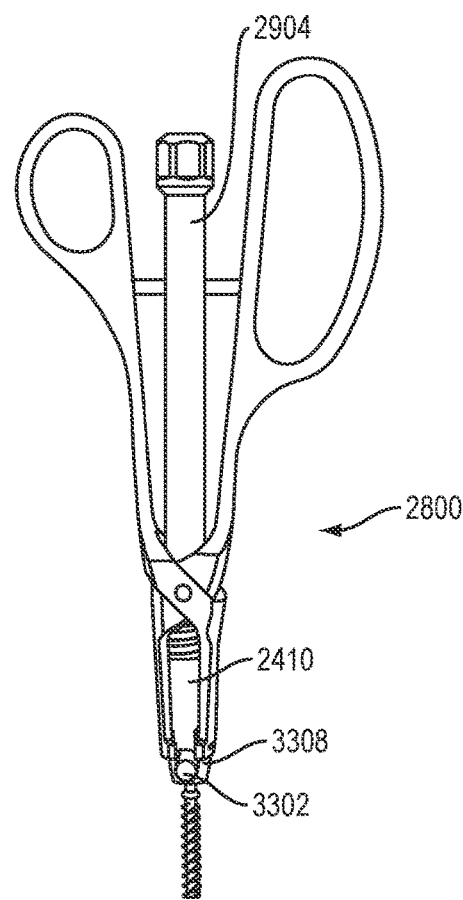
FIG. 36 is a perspective view of the instrument of FIG. 28 axially reducing a spinal fixation rod.

With lateral reduction complete, the rod can be axially reduced into the channel of the receiver head, as shown in FIG. 36. This is accomplished by rotating the reducer tube 2904 using the drive feature formed at its proximal end. Rotation of the reducer tube 2904 through the threads formed on the forceps body causes translation of the rod-engaging tip 2910 along the distal forceps arms or jaws. The rod-engaging tip translates distally and forces the rod 3302 in the same direction toward the channel 3304 of the receiver head 3308. This axial reduction can be maintained by virtue of the threaded connection between the reducer tube and forceps body.

FIG. 37 illustrates introduction of a set screw 3702 and set screw insertion instrument 3704 through the cannula of the reducer tube 2904. Using this cannula access, the set screw 3702 can be delivered to the receiver head 3308 of the bone anchor and installed to secure capture of the rod 3302 within the channel 3304 of the receiver head. FIG. 38 illustrates tightening of the set screw 3702 using the inserter 3704 positioned within the cannula of the reducer tube 2904. Introduced to the bone anchor in this manner, the set screw 3702 can be provisionally and finally tightened to complete spinal fixation construct without the need to remove the biplanar forceps reducer.

Figure 39:
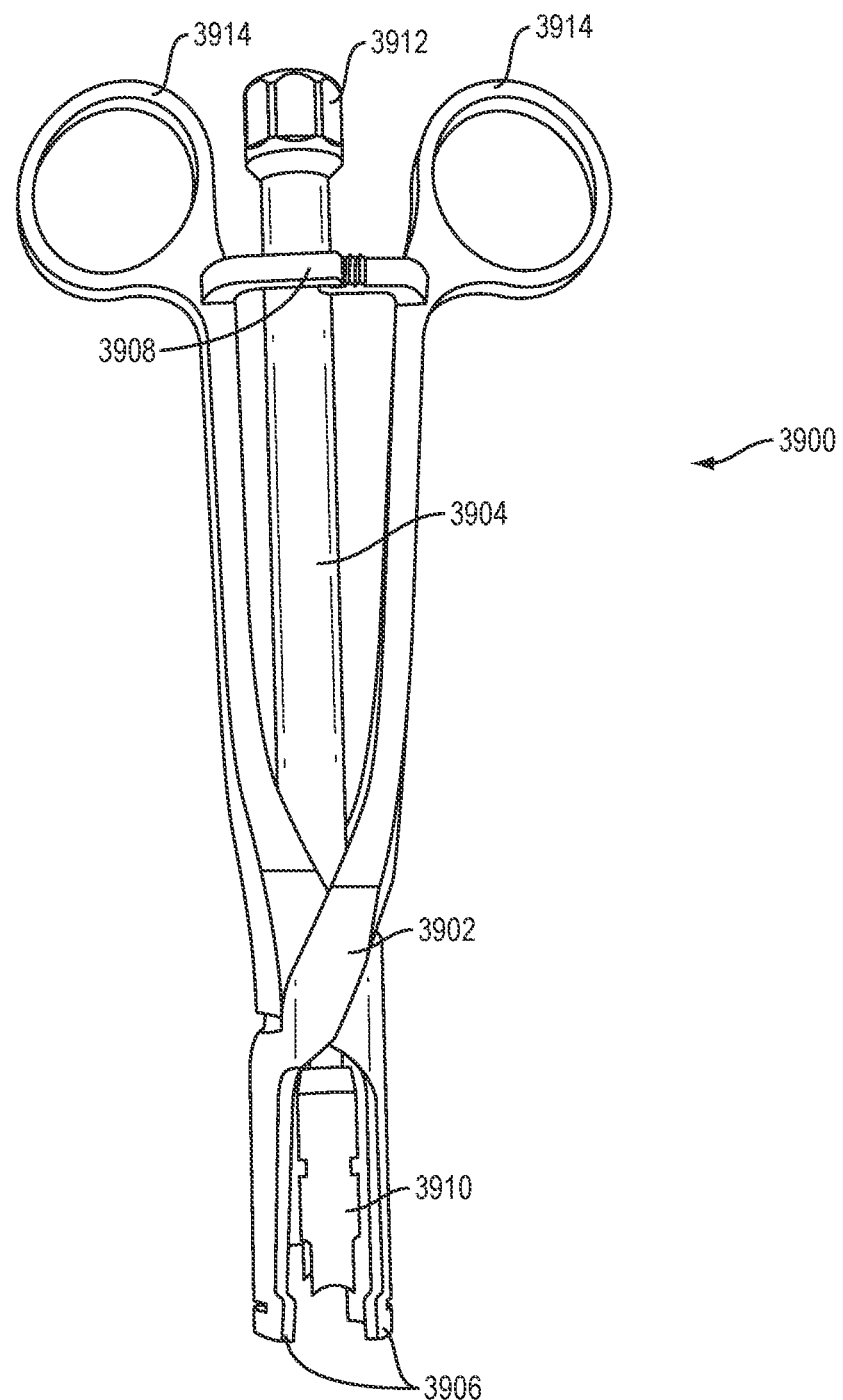
FIG. 39 is a perspective view of one embodiment of a biplanar forceps reducer according to the present disclosure.

FIG. 39 illustrates another embodiment of a biplanar forceps reducer 3900 that is similar to the reducer 2800 discussed above, including lateral reduction forceps 3902 with internal reduction threads that interface with a hollow axial reducer tube 3904 having external reduction threads formed thereon. The instrument 3900 likewise includes opposed distal tips 3906 of the forceps 3902 that can interface with portions of a bone anchor receiver head, a ratchet lock 3908 that is offset from the longitudinal axis of the reducer tube, a rod-engaging reduction tip 3910 coupled to a distal end of the reducer tube 3904 in a manner that allows relative rotation of the tip about a longitudinal axis of the tube but prevents axial translation or separation of the components, and a driver feature 3912 or handle formed on a proximal end of the axial reducer tube 3904 to facilitate rotation of the tube to effect axial reduction of a rod disposed between the opposed jaws of the lateral reduction forceps 3902. The reducer 3900, however, utilizes a different configuration of user-graspable handles/finger loops 3914 from the handles/finger loops 2914 utilized in the reducer 2800. Any of a variety of finger loops or other user-graspable handle configurations can be employed. Several examples are disclosed in the embodiments described herein, but any combination of grips is possible and contemplated by the present disclosure.

Figure 40:
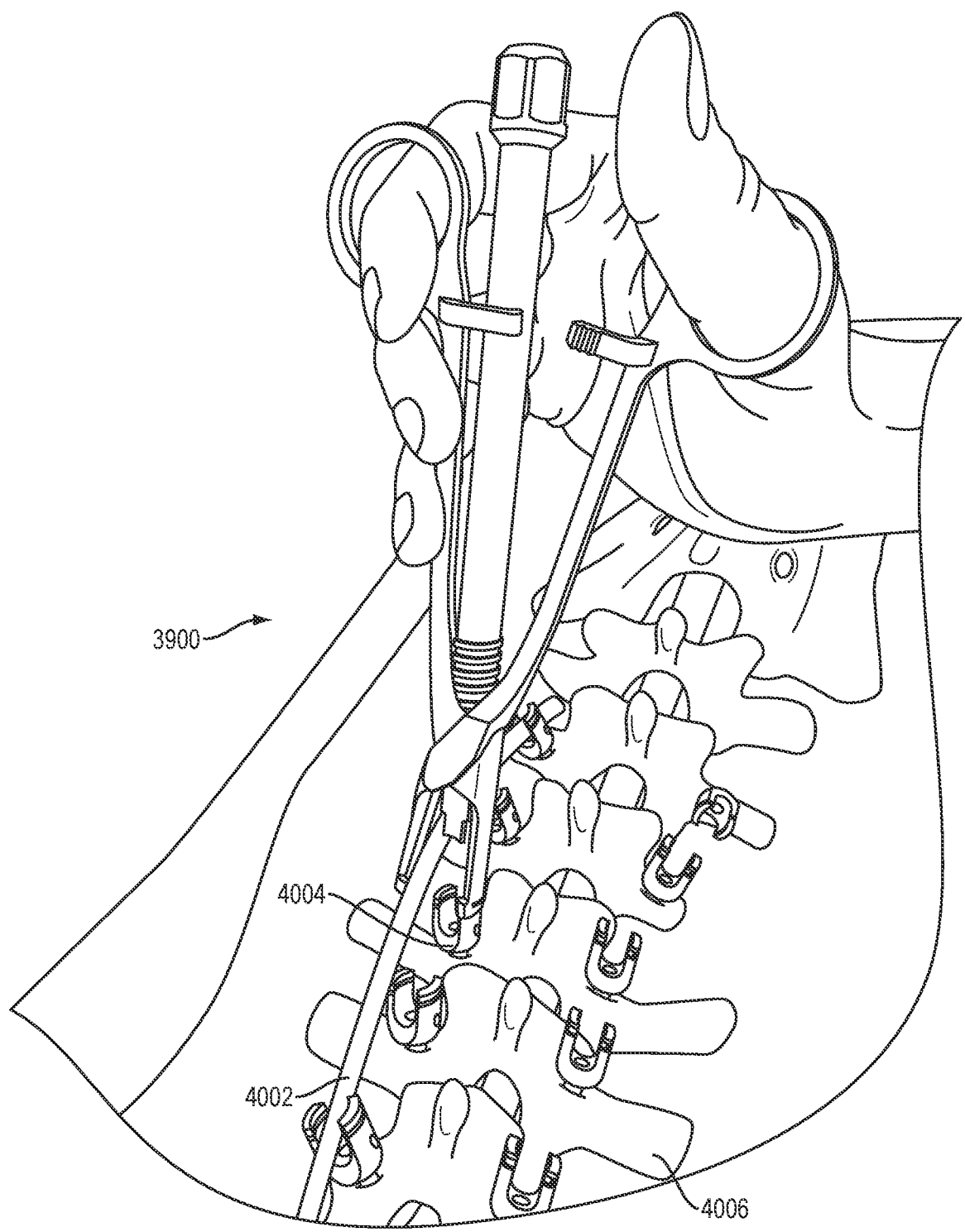
FIG. 40 is a perspective view of the instrument of FIG. 39 capturing a bone screw and spinal fixation rod.

FIG. 40 illustrates a rod 4002 that is positioned both laterally and dorsally relative to one or more bone anchors 4004 implanted in the vertebrae of a patient's spine 4006. In such a case, the rod 4002 needs to be translated in two planes to be received within the channel formed in the receiver heads of the implanted bone anchors 4004: medially in the coronal plane and anteriorly in the sagittal plane. The figure shows the biplanar forceps reducer 3900 disposed to impart lateral and axial reduction to the rod 4002 relative to a bone anchor 4004. In some procedures, additional reducer instruments can be coupled to each of the adjacent bone anchors (or all of the bone anchors) and used together to provide the required reduction forces.

Figure 41:
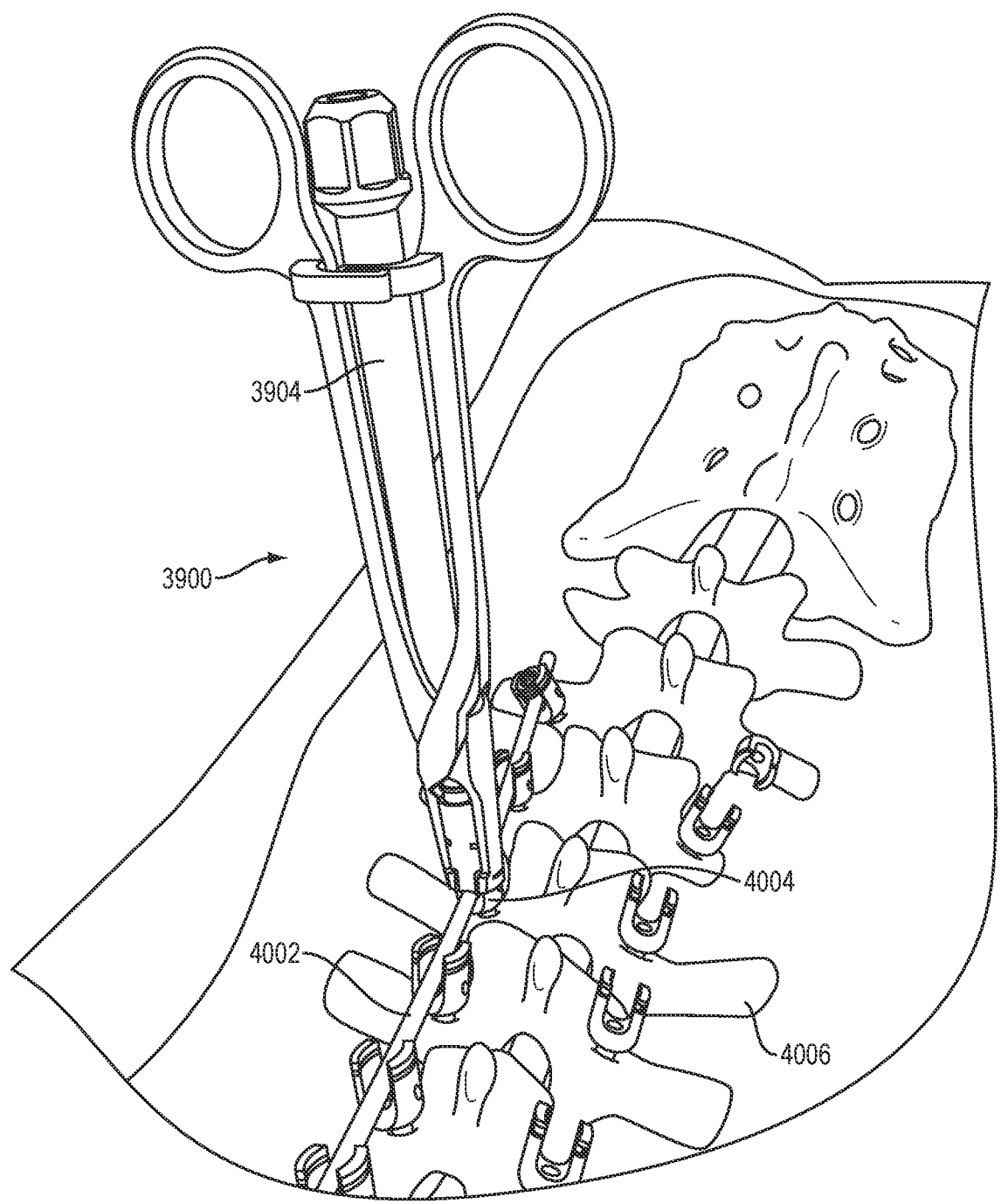
FIG. 41 is a perspective view of the instrument of FIG. 39 after laterally and axially reducing a spinal fixation rod into a bone screw.

FIG. 41 illustrates the biplanar forceps reducer 3900 after imparting lateral and axial reduction forces to move the rod 4002 into the channels of the implanted receiver heads of bone anchors 4004. The lateral reduction can be maintained by virtue of the locking forceps handles and the axial reduction can be maintained by virtue of the threaded engagement between the reducer tube and the forceps body. From the illustrated configuration, a user can introduce a set screw through the cannulated reducer tube 3904 and provisionally or finally lock the rod 4002 into position relative to the implanted bone anchor 4004.

Figure 42:
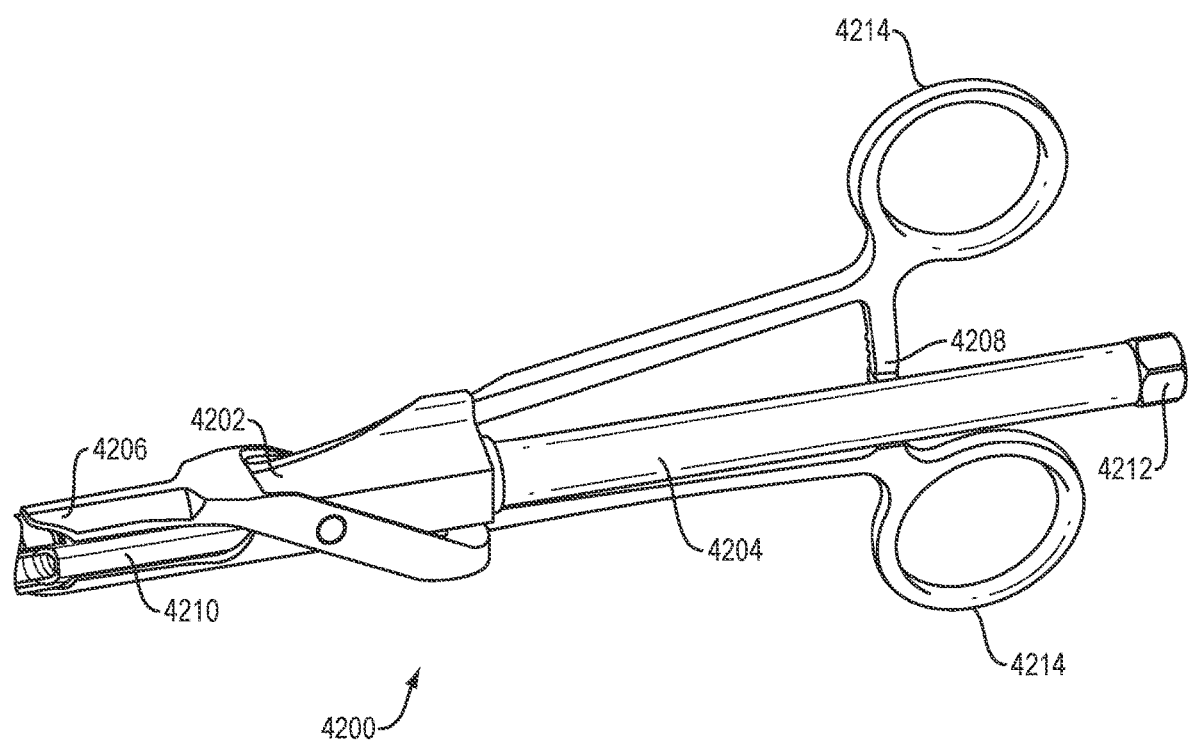
FIG. 42 is a perspective view of one embodiment of a biplanar forceps reducer according to the present disclosure.
Figure 52A:
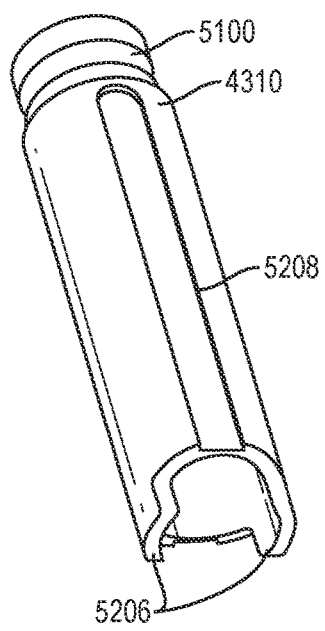
FIG. 52A is a perspective view of a rod-engaging reducer tip of the instrument of FIG. 43A.
Figure 52B:
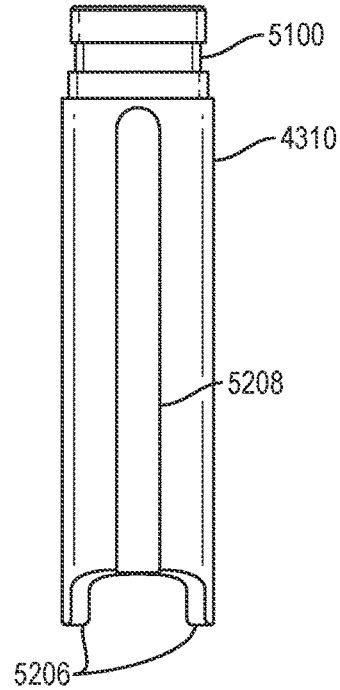
FIG. 52B is a top view of a rod-engaging reducer tip of the instrument of FIG. 43A.

FIG. 42 illustrates another embodiment of a biplanar forceps reducer 4200 that is similar to the reducers 2800, 3900 discussed above, including lateral reduction forceps 4202 with internal reduction threads that interface with a hollow axial reducer tube 4204 having external reduction threads formed thereon. The instrument 4200 likewise includes opposed distal tips 4206 of the forceps 4202 that can interface with portions of a bone anchor receiver head, a ratchet lock 4208 that is offset from the longitudinal axis of the reducer tube, a rod-engaging reduction tip 4210 coupled to a distal end of the reducer tube 4204 in a manner that allows relative rotation of the tip about a longitudinal axis of the tube but prevents axial translation or separation of the components, and a driver feature 4212 or handle formed on a proximal end of the axial reducer tube 4204 to facilitate rotation of the tube to effect axial reduction of a rod disposed between the opposed jaws of the lateral reduction forceps 4202. The reducer 4200, however, utilizes a different configuration of user-graspable handles/finger loops 4214 from those utilized in the above-described reducers. More particularly, the handles 4214 in the instrument 4200 are offset from the longitudinal axis of the reducer tube 4204, such that they lie in a plane with the ratchet lock 4208. In contrast, the user-graspable handles 2914 and 3914 are aligned with the longitudinal axis of the reducer tube and only the ratchet lock 4208 extends to a position offset from the longitudinal axis of the reducer tube.

FIGS. 43A-73B illustrate additional views of embodiments of the biplanar forceps reducer instruments disclosed herein. More particularly, FIGS. 43A-43D illustrate various views of a biplanar forceps reducer 4300 similar to the reducer 4200 described above, including forceps 4302, reducer tube 4304, ratchet lock 4308, reducing tip 4310, and drive feature 4312. FIGS. 44A and 44B illustrate cross-sectional views of the reducer 4300 showing interaction of the reducer tube 4304 with the forceps body 4302 and the shoulder 4316 formed on the tube that serves as a depth stop for distal advancement of the tube relative to the forceps body. FIG. 45 illustrates the proximal removal of the reducer tube 4304 and reducing tip 4310 from the forceps body 4302. FIG. 46 illustrates an exploded view of the two forceps handles that are coupled by pins 4320 to facilitate pivoting movement therebetween.

FIGS. 47A-47C illustrate various views of a dowel pin 4700 that can be used to couple the reducer tube and rod-engaging end in a manner that permits relative rotation and prevents relative axial translation. This component can be seen in the detail cross-sectional view of FIG. 51B that illustrates the reducer tube and rod-engaging tip assembly. The detail cross-sectional view of FIG. 51B shows the dowel pin 4700 of FIG. 47 disposed in holes formed in the distal portion of the reducer tube 4304 and extending into a groove 5100 formed in the proximal portion of the rod-engaging tip 4310 to couple these components in a manner that allows rotation and prevents axial translation. Also shown in this view is the thrust washer 4800 of FIGS. 48A-48C disposed between the reducer tube 4304 and rod-engaging tip 4310. More particularly, the thrust washer 4800 is disposed at a proximal end of the rod-engaging tip 4310 and interfaces at its proximal end with a distal-facing shoulder 5102 formed on an inner surface of the reducer tube 4304.

FIGS. 49A-49C illustrate various views of a rotation pin 4320 that can be used to couple the opposed arms of the forceps 4302, as shown in FIG. 46.

FIGS. 50A and 50B illustrate various view of the reducer tube 4304 and rod-engaging tip 4310. FIGS. 51A and 51B illustrate these components in cross-section to show their coupling, as described above.

Figure 53:
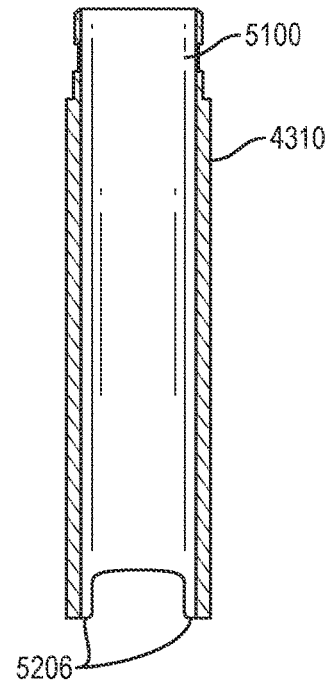
FIG. 53 is a longitudinal cross-sectional view of a rod-engaging reducer tip of the instrument of FIG. 43A.
Figure 52C:
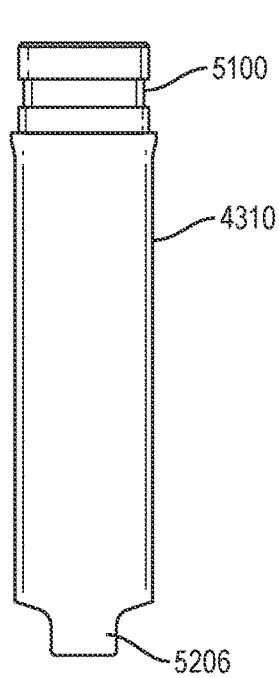
FIG. 52C is a side view a rod-engaging reducer tip of the instrument of FIG. 43A.
Figure 52D:
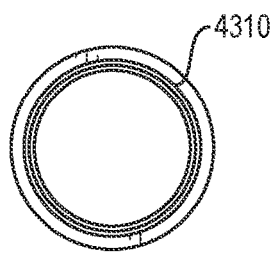
FIG. 52D is a first end view of a rod-engaging reducer tip of the instrument of FIG. 43A.
Figure 52E:
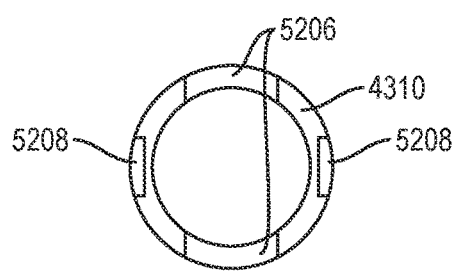
FIG. 52E is a second end view of a rod-engaging reducer tip of the instrument of FIG. 43A.
Figure 54:
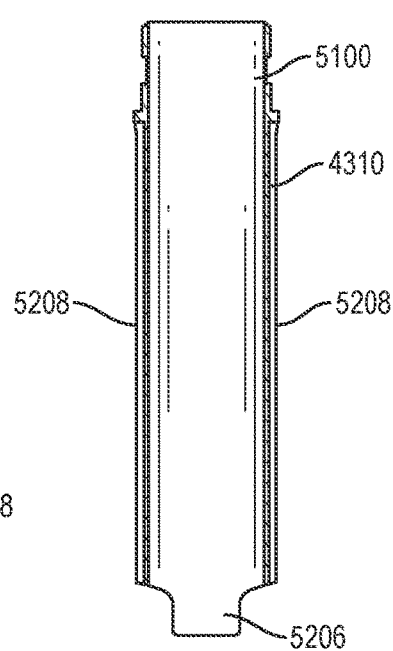
FIG. 54 is another longitudinal cross-sectional view of a rod-engaging reducer tip of the instrument of FIG. 43A.
Figure 55A:
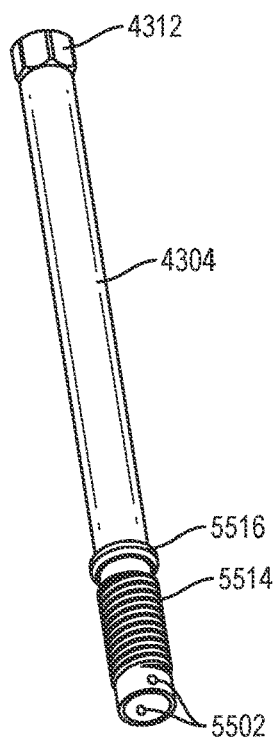
FIG. 55A is a perspective view of a reducer tube of the instrument of FIG. 43A.
Figure 55B:
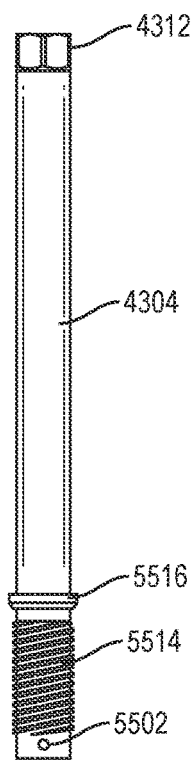
FIG. 55B is a side view of a reducer tube of the instrument of FIG. 43A.
Figure 55C:
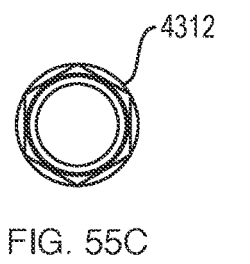
FIG. 55C is a first end view of a reducer tube of the instrument of FIG. 43A.
Figure 55D:
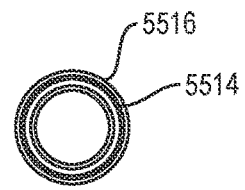
FIG. 55D is a second end view of a reducer tube of the instrument of FIG. 43A.

FIGS. 52A-52E illustrate various views of the rod-engaging tip 4310 that interfaces with the reducer tube 4304 and forceps 4302 to provide translation without rotation in connection with rotation of the reducer tube. FIGS. 53 and 54 illustrate different cross-sectional views of the rod-engaging tip 4310. In particular, these figures highlight the groove 5100 formed at a proximal end of the rod-engaging tip and configured to receive the pins 4700 to couple the tip to the reducer tube 4304 in a manner that allow for relative rotation. Also shown is the longitudinal or axial groove 5208 formed in opposing sides of the outer surface of the tip 4310 that can receive a pin or other protrusion formed on an inner surface of a lumen of the forceps 4302 to maintain a rotational position of the tip 4310 as it translates in response to rotation of the tube 4304.

Figure 56A:
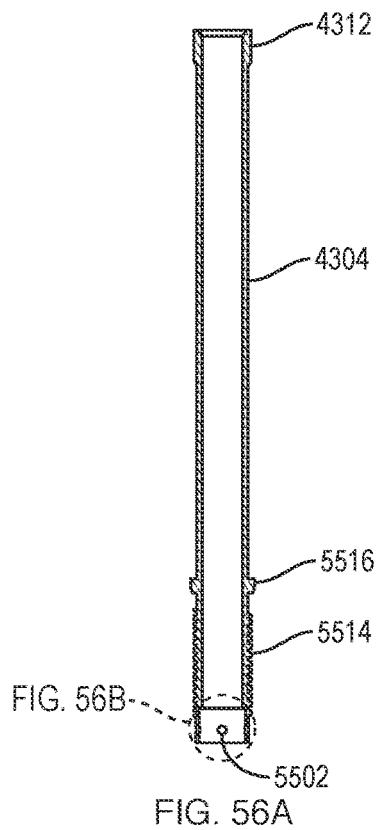
FIG. 56A is a longitudinal cross-sectional view of a reducer tube of the instrument of FIG. 43A.
Figure 56B:
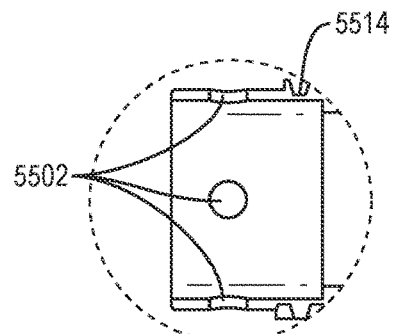
FIG. 56B is a detail view of a distal portion of FIG. 56A.

FIGS. 55A-55D illustrate various views of the reducer tube 4304, including holes 5502 near a distal end thereof that receive the dowel pins 4700 of FIG. 47. Also shown is the drive feature 4312, threads 5514 that engage with the forceps 4302, and shelf 5516 that serves as a stop against further distal advancement of the reducer tube 4304 relative to the forceps 4302. FIGS. 56A and 56B illustrate different cross-sectional views of the reducing tube 4304.

Figure 61:
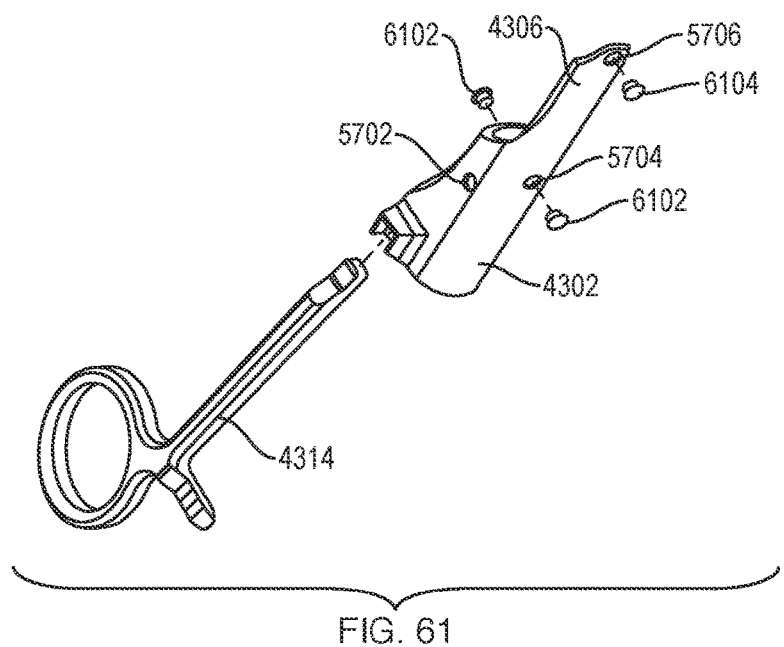
FIG. 61 is an exploded view of a first forceps arm of the instrument of FIG. 43A.
Figures 62A, 62B, 62C:
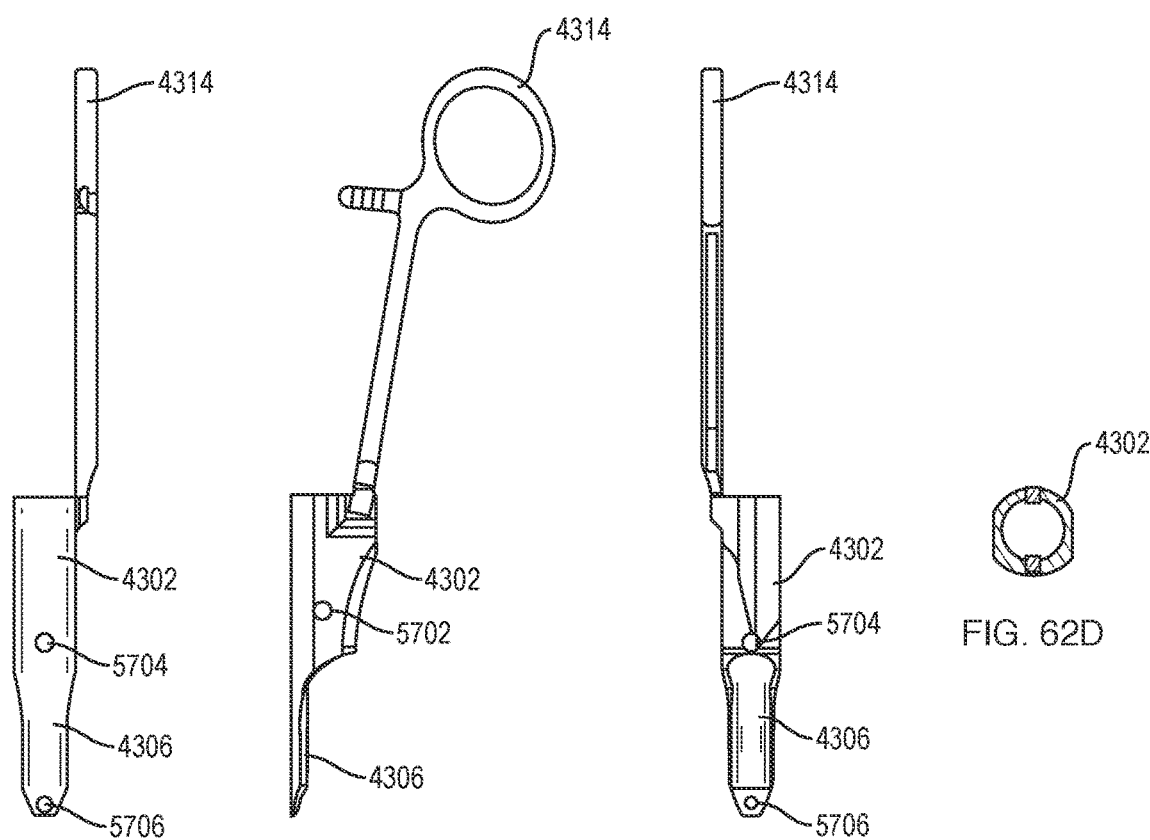
FIG. 62A is a bottom view of a first forceps arm of the instrument of FIG. 43A.
FIG. 62B is another side view of a first forceps arm of the instrument of FIG. 43A.
FIG. 62C is another top view of a first forceps arm of the instrument of FIG. 43A.
Figure 65A:
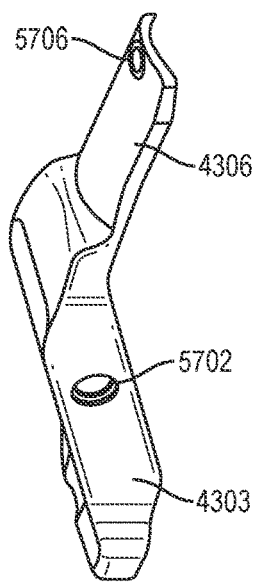
FIG. 65A is a perspective view of a pivot arm of the instrument of FIG. 43A.
Figure 65B:
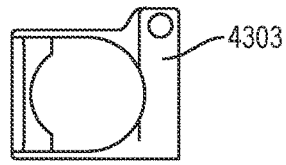
FIG. 65B is an end view of a pivot arm of the instrument of FIG. 43A.
Figure 65C:
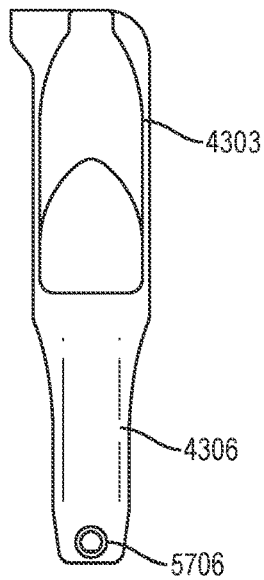
FIG. 65C is a top view of a pivot arm of the instrument of FIG. 43A.
Figure 65D:
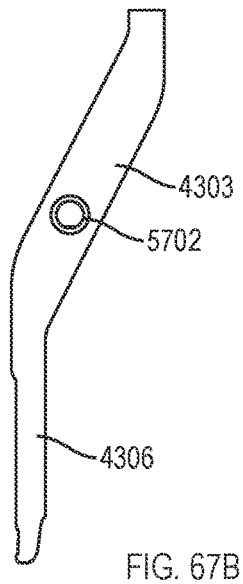
Figure 67A:
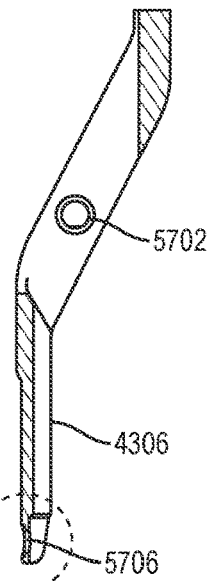
Figure 65E:
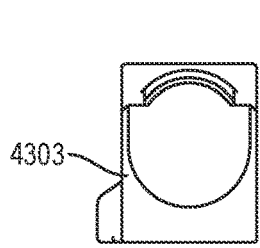
Figure 66A:
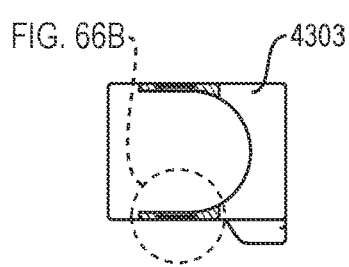
Figure 67B:
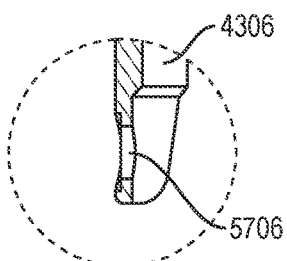
Figure 66B:
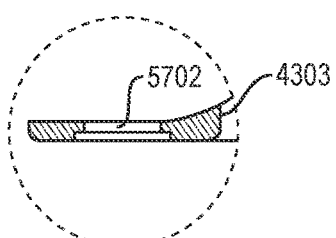

FIGS. 57A-57G illustrate various views of the forceps body 4302, including the internal threads 5714 formed thereon and holes 5702 that receive the rotation pins 4320 of FIGS. 49A-49C to join the opposed forceps arms or jaws. FIGS. 58A and 58B illustrate cross-sectional views of the forceps body 4302. Also shown in these figures is a hole 5704 that can accommodate a pin 6102 (see FIGS. 61 and 68A-68C) that extends into the inner lumen of the forceps body 4302. This pin can, for example, be received within the groove 5208 formed in the rod-engaging tip 4310 to maintain its rotational position relative to the forceps body 4302 as the reducer tube 4304 is rotated to cause translation of the rod-engaging tip 4310. One or more of these holes can be formed in the forceps body 4302 (e.g., two opposing pins 6102 are shown in FIG. 61) and the pin can be secured in a number of manners, including use of adhesives, welding, other mechanical fastening, etc. Further, in some embodiments, a protrusion or other feature can be integrally formed with the body rather than inserting a pin through a hole.

These figures also illustrate a further hole 5706 formed in a distal end of the distal tip 4306 of the forceps. This hole can accommodate a pin 6104 (see FIGS. 61 and 67A-67C) that extends radially inward from the distal tip 4306 and can be received in, for example, a hole or bore formed in a receiver head of a bone screw in order to facilitate coupling between the distal tip 4306 of the forceps and the receiver head. One or more of these holes can be formed in the forceps body 4302 and the pin can be secured in a number of manners, including use of adhesives, welding, other mechanical fastening, etc. Further, in some embodiments, a protrusion or other feature can be integrally formed with the body rather than inserting a pin through a hole. And, as described above, in other embodiments different shapes, such as a shoulder or ridge, etc., can be utilized.

Figure 59:
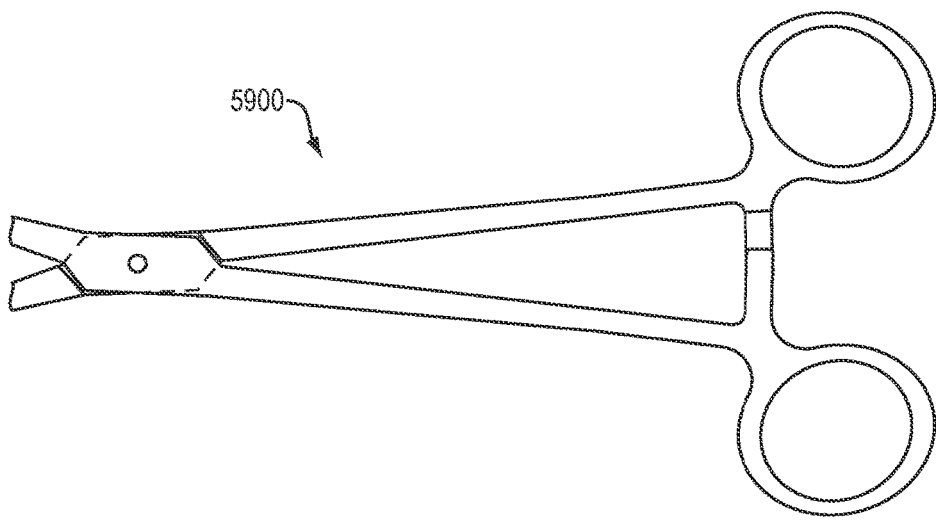
FIG. 59 is a side view of one embodiment of forceps handles according to the present disclosure.
Figures 60A, 60B, 60C, 60D:
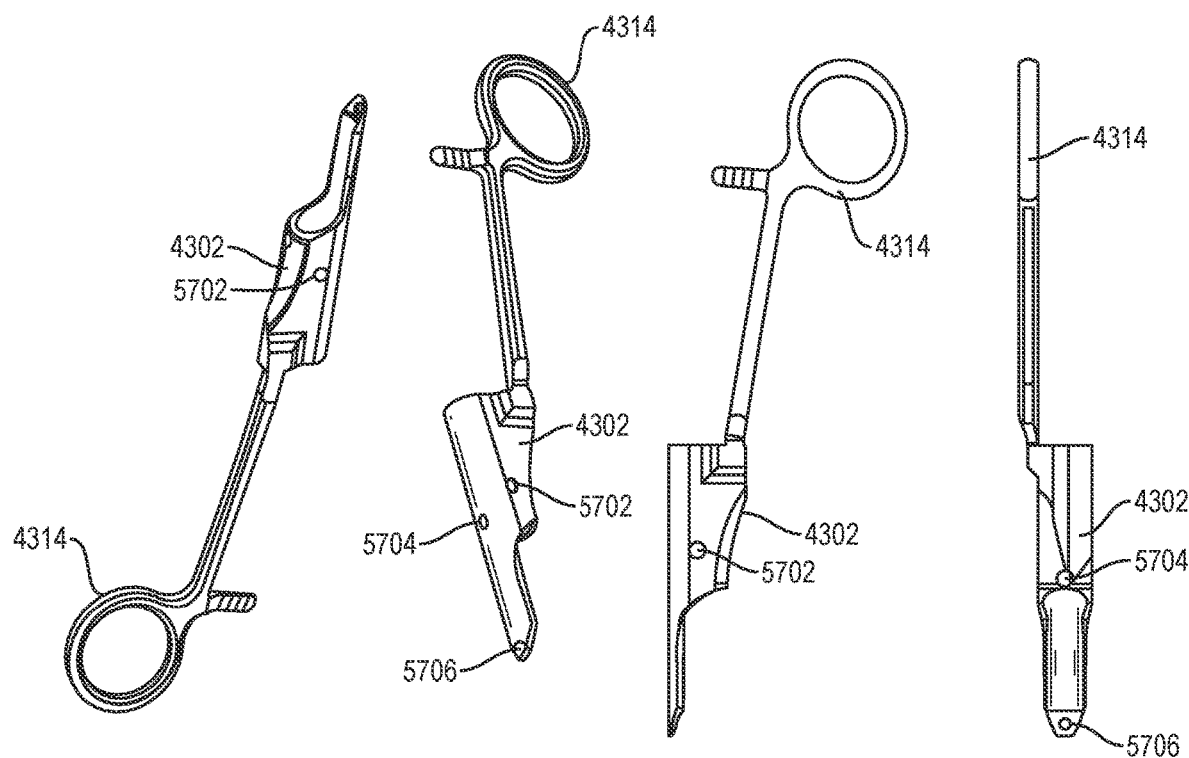
FIG. 60A is a perspective view of a first forceps arm of the instrument of FIG. 43A.
FIG. 60B is another perspective view of a first forceps arm of the instrument of FIG. 43A.
FIG. 60C is a side view of a first forceps arm of the instrument of FIG. 43A.
FIG. 60D is a top view of a first forceps arm of the instrument of FIG. 43A.

FIG. 59 illustrates one embodiment of proximal forceps handles 5900 including rings to accept user fingers and a ratchet lock. As noted above, a variety of different forceps handle shapes, whether including finger rings or not, can be utilized.

FIGS. 60A-60D, 61, and 62A-62D illustrate various views of the forceps body 4302 and proximal handles/finger rings 4314, which can be integrally formed or joined by any of a variety of techniques, including mechanical coupling with bolts, welding, adhesives, etc.

FIGS. 63A-63E and 64 illustrate various view of the forceps pivot arm 4303 that couples to the forceps body 4302 of FIGS. 60A-62D to form the opposed forceps jaws or arms. FIGS. 65A-67B illustrate various views of portions of the pivot arm 4303 of FIGS. 63A-64.

Figure 68A:
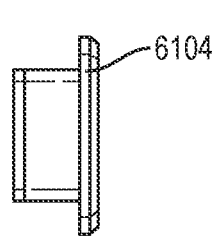
Figure 68B:
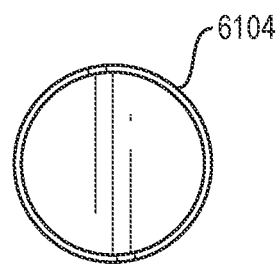
Figure 68C:
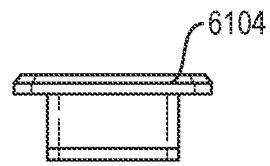

FIGS. 68A-68C illustrate various views of an implant locking pin 6104 that can be received within a bore 5706 of each distal forceps jaw or arm (e.g., as shown in FIGS. 60A-62D and 63A-67B). The locking pins 6104 can be configured to protrude from an inner surface of the forceps jaws and be received within a recess formed in a bone anchor receiver member to aid the forceps in locking to the receiver head.

Figure 69A:
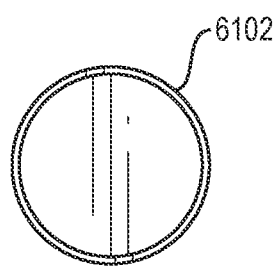
Figure 69B:
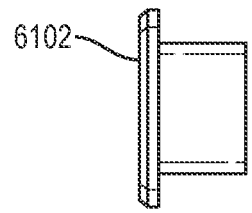
Figure 69C:
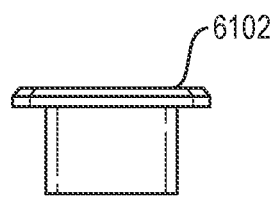

FIGS. 69A-69C illustrate various views of an alignment pin 6102 that can be received within a bore 5704 formed in the forceps body, as shown in FIGS. 60A-62D. In the illustrated embodiment, these alignment pins 6102 can extend into longitudinal grooves 5208 formed in the sides of the rod-engaging tip 4310 (as shown in FIGS. 52A-54) to prevent the rod-engaging tip 4310 from rotating relative to the forceps body 4302 as it translates relative thereto when the reducer tube 4304 is rotated through the threads 5714 formed on an inner surface of the forceps body.

FIGS. 70-73B illustrate various views of proximal handles 7014, 7114, 7214, 7314 that can be used with the forceps reducers disclosed herein, including rings to accept user fingers for actuation and ratchet locks 7008, 7108, 7208, 7308 to maintain lateral reduction.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A surgical instrument, comprising:
    a first arm having a proximal end, a distal end, and a housing disposed therebetween, the housing including a threaded lumen defining a longitudinal axis;
    a second arm having a proximal end and a distal end, the second arm pivotably coupled to the first arm;
    a tube having a threaded outer surface portion disposed within the threaded lumen, a depth stop formed proximal to the threaded portion, and a drive feature at a proximal end of the tube configured to removably couple with a driver to impart torque to the tube; and
    a rod-engaging tip rotatably coupled to a distal end of the tube;
    wherein the first and second arms are configured to translate a spinal fixation element laterally toward the longitudinal axis when pivoted toward one another and the rod-engaging tip is configured to translate the spinal fixation element axially along the longitudinal axis when the tube is rotated relative to the housing.
2. The instrument of claim 1, wherein the depth stop defines a maximum outer diameter of the tube.
3. The instrument of any of claims 1 to 2, wherein the depth stop is a shoulder formed around at least a portion of the circumference of the tube.
4. The instrument of any of claims 1 to 3, wherein the lumen includes continuous threads formed around a circumference thereof.
5. The instrument of any of claims 1 to 4, wherein an inner lumen of the tube is accessible from a proximal end of the tube through the drive feature.
6. The instrument of claim 5, wherein the rod-engaging tip includes an inner lumen coaxially disposed with the inner lumen of the tube.
7. The instrument of any of claims 1 to 6, wherein the rod-engaging tip includes an opening formed in a distal portion of a sidewall to facilitate viewing contents of an inner lumen of the rod-engaging tip.
8. The instrument of any of claims 1 to 7, wherein a distal end of at least one of the first and second arms includes a protrusion configured to extend into a recess of a bone anchor receiver member.
9. The instrument of claim 8, wherein the protrusion is a pin disposed in a bore formed in the distal end of at least one of the first and second arms.
10. The instrument of claim 8, wherein the protrusion is a ridge extending across a width of the arm.
11. The instrument of any of claims 8 to 10, wherein the protrusion is disposed proximal to a distal-most end of the arm and an inner surface of the arm distal to the protrusion has a conical tapering profile.
12. The instrument of claim 11, wherein the inner surface of the arm includes sidewalls extending outward from the inner surface at lateral ends of the arm, and opposed, inward-facing surfaces of each sidewall have a planar tapering profile.
13. The instrument of any of claims 1 to 12, further comprising a lock configured to selectively maintain a position of the first and second arms relative to one another.
14. The instrument of claim 13, wherein the lock is coupled to a proximal portion of one or more of the first and second arms, and a proximal end of the tube is disposed distal to the lock.
15. A surgical method, comprising:
    positioning a first arm of a reducer instrument against a bone anchor receiver member;
    positioning a second arm of the reducer instrument against a spinal fixation element;

positioning a threaded outer surface portion of a tube of the reducer instrument within a threaded lumen formed in a housing of the first arm of the reducer instrument;

pivoting the first and second arms of the reducer instrument toward one another to translate the spinal fixation element laterally toward a longitudinal axis defined by the threaded lumen;

coupling a driver to a drive feature formed at a proximal end of the tube;

rotating the tube of the reducer instrument to translate the spinal fixation element axially along the longitudinal axis until a depth stop formed on the tube proximal to the threaded outer surface portion contacts the housing.

16. The method of claim 15, further comprising engaging a lock to maintain a position of the first and second arms relative to one another after pivoting the first and second arms toward one another.

17. The method of any of claims 15 to 16, further comprising separating the driver from the proximal end of the tube after rotating the tube to translate the spinal fixation element axially.

18. The method of claim 17, further comprising inserting a set screw through an inner lumen of the tube and coupling the set screw with the receiver member.

19. The method of claim 18, further comprising visually inspecting the set screw while coupled to the receiver member using an opening formed in a distal portion of a sidewall of rod-engaging tip coupled to the tube.

20. A surgical instrument, comprising:
a first arm having a proximal end, a distal end, and a housing disposed therebetween, the housing including a lumen defining a longitudinal axis, the lumen having continuous threads formed around a circumference thereof;
a second arm having a proximal end and a distal end, the second arm pivotably coupled to the first arm;
a tube having a threaded outer surface portion disposed within the lumen;
a rod-engaging tip rotatably coupled to a distal end of the tube, the rod-engaging tip being constrained against rotation relative to the housing by a protrusion coupled to the housing that is received in a recess of the rod-engaging tip;
wherein the first and second arms are configured to translate a spinal fixation element laterally toward the longitudinal axis when pivoted toward one another and the rod-engaging tip is configured to translate the spinal fixation element axially along the longitudinal axis when the tube is rotated relative to the housing.

21. The instrument of claim 20, wherein the threads on the outer surface portion of the tube have a plurality of starts.

22. The instrument of claim 21, wherein the threads on the outer portion of the tube have three starts.

23. The instrument of any of claims 20 to 22, wherein an outer diameter of the threaded outer surface portion of the tube is less than or equal to about 45% larger than a diameter of an inner lumen of the tube.

24. A surgical instrument, comprising:
opposed arms pivotably coupled to one another;
a tube threadably coupled to the opposed arms; and
a rod-engaging tip rotatably coupled to the tube;
wherein the opposed arms are configured to laterally translate a spinal fixation element when pivoted toward one another and the rod-engagement tip is configured to axially translate the spinal fixation element when the tube is rotated relative to the opposed arms and the rod-engagement tip.

25. The instrument of claim 24, wherein one of the opposed arms includes a housing having a threaded lumen formed therein.

26. The instrument of claim 25, wherein the tube includes external threads formed thereon that interface with the threaded lumen of the body.

27. The instrument of claim 26, wherein the external threads formed on the tube include a plurality of starts.

28. The instrument of claim 27, wherein the external threads formed on the tube include three starts.

29. The instrument of any of claims 26 to 28, wherein an outer diameter of the external threads of the tube is less than or equal to about 45% larger than a diameter of an inner lumen of the tube.

30. The instrument of any of claims 26 to 29, wherein the tube includes a depth stop formed proximal to the external threads.

31. The instrument of claim 30, wherein the depth stop defines a maximum outer diameter of the tube.

32. The instrument of any of claims 30 to 31, wherein the depth stop is a shoulder formed around at least a portion of the circumference of the tube.

33. The instrument of any of claims 25 to 32, wherein the threaded lumen includes continuous threads formed around a circumference thereof.

34. The instrument of any of claims 25 to 33, wherein the housing includes a protrusion received within a recess of the rod-engaging tip to constrain the rod-engaging tip against rotation relative to the housing.

35. The instrument of any of claims 24 to 34, wherein the opposed arms include opposed proximally-extending handles for user actuation.

36. The instrument of any of claims 24 to 35, wherein the opposed arms include a lock to maintain their relative position.

37. The instrument of claim 36, wherein the lock includes a ratchet.

38. The instrument of claim 37, wherein the ratchet is offset from a longitudinal axis of the tube.

39. The instrument of any of claims 36 to 38, wherein the lock is coupled to a proximal portion of one or more of the opposed arms, and a proximal end of the tube is disposed distal to the lock.

40. The instrument of any of claims 24 to 39, wherein the tube includes a drive feature formed at a proximal end thereof to facilitate rotation of the tube.

41. The instrument of claim 40, wherein an inner lumen of the tube is accessible from a proximal end of the tube through the drive feature.

42. The instrument of any of claims 24 to 41, wherein the tube includes an inner lumen and the rod-engaging tip includes an inner lumen that is coaxial with the inner lumen of the tube.

43. The instrument of any of claims 24 to 42, wherein the rod-engaging tip includes an opening formed in a distal portion of a sidewall to facilitate viewing contents of an inner lumen of the rod-engaging tip.

44. The instrument of any of claims 24 to 43, wherein a distal end of at least one of the opposed arms includes an engagement feature configured to interface with a complementary feature of a bone anchor receiver member.

45. The instrument of claim 44, wherein the engagement feature includes a protrusion configured to extend into a recess of a bone anchor receiver member.
46. The instrument of claim 45, wherein the protrusion is a pin disposed in a bore formed in the distal end of the arm.
47. The instrument of claim 45, wherein the protrusion is a ridge extending across a width of the arm.
48. The instrument of any of claims 44 to 47, wherein the engagement feature is disposed proximal to a distal-most end of the arm and an inner surface of the arm distal to the protrusion has a conical tapering profile.
49. The instrument of claim 48, wherein the inner surface of the arm includes sidewalls extending outward from the inner surface at lateral ends of the arm, and opposed, inward-facing surfaces of each sidewall have a planar tapering profile.
50. A surgical method, comprising:
positioning a first arm of a reducer instrument against a bone anchor receiver member;
positioning a second arm of the reducer instrument against a spinal fixation element;
pivoting the first and second arms of the reducer instrument toward one another to laterally translate the rod toward the receiver member;
rotating a tube of the reducer instrument to axially translate the spinal fixation element toward the receiver member.
51. The method of claim 50, further comprising inserting a set screw through a lumen formed in the tube and coupling the set screw to the receiver member.
52. The method of claim 51, further comprising visually inspecting the set screw while coupled to the receiver member using an opening formed in a distal portion of a sidewall of a rod-engaging tip coupled to the tube.
53. The method of any of claims 50 to 52, further comprising locking a position of the first and second arms relative to one another.
54. The method of any of claims 50 to 53, further comprising positioning a threaded outer surface portion of the tube within a threaded lumen formed in a housing coupled to one or more of the first arm and the second arm.
55. The method of claim 54, wherein rotating the tube is continued until a depth stop formed on the tube proximal to the threaded outer surface portion contacts the housing.
56. The method of any of claims 50 to 55, further comprising coupling a driver to a drive feature formed at a proximal end of the tube prior to rotating the tube to axially translate the spinal fixation element.
57. The method of claim 56, further comprising separating the driver from the proximal end of the tube after rotating the tube to axially translate the spinal fixation element.
58. The method of any of claims 50 to 57, further comprising engaging a lock to maintain a position of the first and second arms relative to one another after pivoting the first and second arms toward one another.

What is claimed is:
1. A surgical instrument, comprising:
a first arm having a proximal end, a distal end, and a housing disposed therebetween, the housing including a threaded lumen defining a longitudinal axis;
a second arm having a proximal end and a distal end, the second arm pivotably coupled to the first arm;
a tube having a threaded outer surface portion disposed within the threaded lumen, a depth stop formed proximal to the threaded portion, and a drive feature at a proximal end of the tube configured to removably couple with a driver to impart torque to the tube; and
a rod-engaging tip rotatably coupled to a distal end of the tube;
wherein the first and second arms are configured to translate a spinal fixation element laterally toward the longitudinal axis when pivoted toward one another and the rod-engaging tip is configured to translate the spinal fixation element axially along the longitudinal axis when the tube is rotated relative to the housing, and
wherein the longitudinal axis of the lumen of the housing lies in a plane defined by longitudinal axes of the first arm and the second arm.
2. The instrument of claim 1, wherein the depth stop defines a maximum outer diameter of the tube.
3. The instrument of claim 1, wherein the depth stop is a shoulder formed around at least a portion of the circumference of the tube.
4. The instrument of claim 1, wherein the lumen includes continuous threads formed around a circumference thereof.
5. The instrument of claim 1, wherein an inner lumen of the tube is accessible from a proximal end of the tube through the drive feature.
6. The instrument of claim 5, wherein the rod-engaging tip includes an inner lumen coaxially disposed with the inner lumen of the tube.
7. The instrument of claim 1, wherein the rod-engaging tip includes an opening formed in a distal portion of a sidewall to facilitate viewing contents of an inner lumen of the rod-engaging tip.
8. The instrument of claim 1, wherein a distal end of at least one of the first and second arms includes a protrusion configured to extend into a recess of a bone anchor receiver member.
9. The instrument of claim 8, wherein the protrusion is a pin disposed in a bore formed in the distal end of at least one of the first and second arms.
10. The instrument of claim 8, wherein the protrusion is a ridge extending across a width of the arm.
11. The instrument of claim 8, wherein the protrusion is disposed proximal to a distal-most end of the arm and an inner surface of the arm distal to the protrusion has a conical tapering profile.
12. The instrument of claim 11, wherein the inner surface of the arm includes sidewalls extending outward from the inner surface at lateral ends of the arm, and opposed, inward-facing surfaces of each sidewall have a planar tapering profile.
13. The instrument of claim 1, further comprising a lock configured to selectively maintain a position of the first and second arms relative to one another.
14. The instrument of claim 13, wherein the lock is coupled to a proximal portion of one or more of the first and second arms, and a proximal end of the tube is disposed distal to the lock.
15. The instrument of claim 1, wherein the first arm, including the housing, is integrally formed.
16. The instrument of claim 1, further comprising a biasing element that extends from the housing and is located distal to a location at which the second arm is pivotally coupled to the first arm to urge the first and second arms to pivot away from one another.

17. The instrument of claim 16, wherein a proximal end of the biasing element is distal to a proximal end of the housing.

18. A surgical instrument, comprising:
   a first arm having a proximal end, a distal end, and a housing disposed therebetween, the housing including a lumen defining a longitudinal axis, the lumen having continuous threads formed around a circumference thereof;
   a second arm having a proximal end and a distal end, the second arm pivotably coupled to the first arm;
   a tube having a threaded outer surface portion disposed within the lumen;
   a rod-engaging tip rotatably coupled to a distal end of the tube, the rod-engaging tip being constrained against rotation relative to the housing by a protrusion coupled to the housing that is received in a recess of the rod-engaging tip;
   wherein the first and second arms are configured to translate a spinal fixation element laterally toward the longitudinal axis when pivoted toward one another and the rod-engaging tip is configured to translate the spinal fixation element axially along the longitudinal axis when the tube is rotated relative to the housing.

19. The instrument of claim 18, wherein the threads on the outer surface portion of the tube have a plurality of starts.

20. The instrument of claim 19, wherein the threads on the outer portion of the tube have three starts.

21. The instrument of claim 18, wherein an outer diameter of the threaded outer surface portion of the tube is less than or equal to about 45% larger than a diameter of an inner lumen of the tube.

22. The instrument of claim 18, wherein the protrusion extends from the lumen of the housing.

23. A surgical instrument, comprising:
   a first arm having a proximal end, a distal end, and a housing disposed therebetween, the housing including a threaded lumen defining a longitudinal axis;
   a second arm having a proximal end and a distal end, the second arm pivotably coupled to the first arm;
   a tube having a threaded outer surface portion disposed within the threaded lumen, a depth stop formed proximal to the threaded portion, and a drive feature at a proximal end of the tube configured to removably couple with a driver to impart torque to the tube; and
   a rod-engaging tip rotatably coupled to a distal end of the tube;
   wherein the first and second arms are configured to translate a spinal fixation element laterally toward the longitudinal axis when pivoted toward one another and the rod-engaging tip is configured to translate the spinal fixation element axially along the longitudinal axis when the tube is rotated relative to the housing, and wherein the first arm is fixed relative to the housing.

* * * * *